United States Patent
Sokolsky et al.

(10) Patent No.: US 10,752,635 B2
(45) Date of Patent: Aug. 25, 2020

(54) INDAZOLE COMPOUNDS AND USES THEREOF

(71) Applicant: Incyte Corporation, Wilmington, DE (US)

(72) Inventors: Alexander Sokolsky, Philadelphia, PA (US); Oleg Vechorkin, Wilmington, DE (US); Anlai Wang, Wilmington, DE (US); Qinda Ye, Claymont, DE (US); Wenqing Yao, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 16/278,796

(22) Filed: Feb. 19, 2019

(65) Prior Publication Data

US 2019/0256520 A1 Aug. 22, 2019

Related U.S. Application Data

(60) Provisional application No. 62/775,989, filed on Dec. 6, 2018, provisional application No. 62/659,342, filed on Apr. 18, 2018, provisional application No. 62/632,688, filed on Feb. 20, 2018.

(51) Int. Cl.
| | | |
|---|---|---|
| C07D 403/12 | (2006.01) | |
| C07D 403/14 | (2006.01) | |
| C07D 471/08 | (2006.01) | |
| C07D 487/08 | (2006.01) | |
| C07D 401/14 | (2006.01) | |
| C07D 487/10 | (2006.01) | |

(52) U.S. Cl.
CPC ......... C07D 487/08 (2013.01); C07D 401/14 (2013.01); C07D 403/12 (2013.01); C07D 403/14 (2013.01); C07D 471/08 (2013.01); C07D 487/10 (2013.01)

(58) Field of Classification Search
CPC ... C07D 403/12; C07D 403/14; C07D 471/08
See application file for complete search history.

(56) References Cited

U.S. PATENT DOCUMENTS

| | | | |
|---|---|---|---|
| 5,250,534 A | 10/1993 | Bell et al. | |
| 6,200,980 B1 | 3/2001 | Piazza et al. | |
| 6,333,330 B1 | 12/2001 | Bunnage et al. | |
| 6,458,951 B1 | 10/2002 | Bunnage et al. | |
| 6,512,002 B2 | 1/2003 | Lee et al. | |
| 6,670,366 B1 | 12/2003 | Bunnage et al. | |
| 6,743,799 B2 | 6/2004 | Westbrook et al. | |
| 6,756,373 B1 | 6/2004 | Allerton et al. | |
| 6,770,645 B2 | 8/2004 | Denton et al. | |
| 6,784,185 B2 | 8/2004 | Allerton et al. | |
| 6,916,927 B2 | 7/2005 | Bunnage et al. | |
| 7,105,532 B2 | 9/2006 | Rawlings | |
| 7,166,293 B2 | 1/2007 | Teng et al. | |
| 7,259,165 B2 | 8/2007 | Bernotas et al. | |
| 7,345,178 B2 | 3/2008 | Nunes et al. | |
| 7,576,087 B2 | 8/2009 | Bernotas et al. | |
| 7,919,487 B2 | 4/2011 | Sun et al. | |
| 7,968,719 B2 | 6/2011 | Zoller et al. | |
| 8,106,190 B2 | 1/2012 | Kuramochi et al. | |
| 8,450,335 B2 | 5/2013 | Singh et al. | |
| 8,546,403 B2 | 10/2013 | Whitten et al. | |
| 8,637,507 B2 | 1/2014 | Zhou et al. | |
| 8,722,691 B2 | 3/2014 | He et al. | |
| 8,987,273 B2 | 3/2015 | Rehwinkel et al. | |
| 9,090,593 B2 | 7/2015 | Wang et al. | |
| 9,260,425 B2 | 2/2016 | Do et al. | |
| 9,284,319 B2 | 3/2016 | Eis et al. | |
| 9,320,737 B2 | 4/2016 | Eis et al. | |
| 9,718,818 B2 | 8/2017 | DeMong et al. | |
| 9,730,929 B2 | 8/2017 | Eis et al. | |

(Continued)

FOREIGN PATENT DOCUMENTS

| | | |
|---|---|---|
| CN | 102206172 | 10/2011 |
| CN | 102503959 | 6/2012 |

(Continued)

OTHER PUBLICATIONS

Alzabin et al., "Hematopoietic progenitor kinase 1 is a critical component of prostaglandin E2-mediated suppression of the anti-tumor immune response," Cancer Immunol Immunother, 2010, 59(3):419-429.

Alzabin et al., "Hematopoietic progenitor kinase 1 is a negative regulator of dendritic cell activation," J Immunol, 2009, 182(10):6187-6194.

Antoine et al., "Efficient synthesis of novel disubstituted pyrido[3,4-b]pymzines for the design of protein kinase inhibitors," Med Chem Common., 2016, 6:224-229.

Antunes et al., "In silico prediction of novel phosphodiesterase type-5 inhibitors derived from Sildenafil, Vardenafil and Tadalafil," Bioorg Med Chem., Aug. 15, 2008, 16(16):7599-7606.

Atzrodt et al., "The Renaissance of H/D Exchange," Angew. Chem. Int. Ed., 2007, 7744-7765.

(Continued)

Primary Examiner — Brian E McDowell

(74) Attorney, Agent, or Firm — Fish & Richardson P.C.

(57) ABSTRACT

Disclosed are compounds of Formula (I), methods of using the compounds for inhibiting HPK1 activity and pharmaceutical compositions comprising such compounds. The compounds are useful in treating, preventing or ameliorating diseases or disorders associated with HPK1 activity such as cancer.

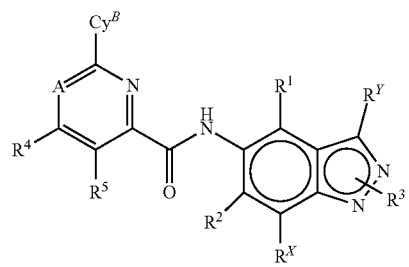

67 Claims, No Drawings

(56) References Cited

U.S. PATENT DOCUMENTS

| | | | |
|---|---|---|---|
| 10,266,530 | B2 | 4/2019 | Vechorkin et al. |
| 10,280,164 | B2 | 5/2019 | Ye et al. |
| 10,435,405 | B2 | 10/2019 | Vechorkin et al. |
| 2002/0013327 | A1 | 1/2002 | Lee et al. |
| 2003/0162782 | A1 | 8/2003 | Grossman et al. |
| 2003/0186996 | A1 | 10/2003 | Teng et al. |
| 2004/0063730 | A1 | 4/2004 | Eggenweiler et al. |
| 2004/0077681 | A1 | 4/2004 | Rawlings et al. |
| 2004/0147546 | A1 | 7/2004 | Tanaka et al. |
| 2004/0157866 | A1 | 8/2004 | Takasugi et al. |
| 2004/0167030 | A1 | 8/2004 | Bernotas et al. |
| 2004/0204417 | A1 | 10/2004 | Perez et al. |
| 2005/0070557 | A1 | 3/2005 | Fryburg et al. |
| 2005/0075795 | A1 | 4/2005 | Pandit |
| 2005/0119278 | A1 | 6/2005 | Teng et al. |
| 2005/0137226 | A1 | 6/2005 | Ji et al. |
| 2005/0208582 | A1 | 9/2005 | Ohi et al. |
| 2005/0261339 | A1 | 11/2005 | Ohi et al. |
| 2006/0106032 | A1 | 5/2006 | Kuo et al. |
| 2007/0087988 | A1 | 4/2007 | Sawasdikosol et al. |
| 2007/0161673 | A1 | 7/2007 | Barker et al. |
| 2007/0185152 | A1 | 8/2007 | Yamashita et al. |
| 2007/0270412 | A1 | 11/2007 | Bell et al. |
| 2008/0280891 | A1 | 11/2008 | Kelly et al. |
| 2010/0035891 | A1 | 2/2010 | Bunnage et al. |
| 2010/0087464 | A1 | 4/2010 | Mi et al. |
| 2010/0216798 | A1 | 8/2010 | Nakai et al. |
| 2012/0129852 | A1 | 5/2012 | Duan et al. |
| 2012/0225869 | A1 | 9/2012 | Liu et al. |
| 2012/0295884 | A1 | 11/2012 | Altmann et al. |
| 2013/0039906 | A1 | 2/2013 | Do et al. |
| 2013/0040949 | A1 | 2/2013 | Gray et al. |
| 2013/0281433 | A1 | 10/2013 | Babaoglu et al. |
| 2014/0225073 | A1 | 8/2014 | Lee et al. |
| 2014/0288045 | A1 | 9/2014 | Ren et al. |
| 2014/0288069 | A1 | 9/2014 | Eis et al. |
| 2014/0350017 | A1 | 11/2014 | Williams et al. |
| 2014/0364605 | A1 | 12/2014 | Li et al. |
| 2015/0038485 | A1 | 2/2015 | Eis et al. |
| 2015/0191462 | A1 | 7/2015 | Hommel et al. |
| 2015/0239868 | A1 | 8/2015 | Pais et al. |
| 2015/0239889 | A1 | 8/2015 | Nakajima et al. |
| 2015/0243908 | A1 | 8/2015 | Lee et al. |
| 2015/0274639 | A1 | 10/2015 | Williams et al. |
| 2015/0328188 | A1 | 11/2015 | Orlemans et al. |
| 2016/0013427 | A1 | 1/2016 | Kim et al. |
| 2016/0046648 | A1 | 2/2016 | Petrukhin et al. |
| 2016/0068529 | A1 | 3/2016 | Kc et al. |
| 2016/0068547 | A1 | 3/2016 | Kc et al. |
| 2016/0068548 | A1 | 3/2016 | Kc et al. |
| 2016/0068551 | A1 | 3/2016 | Kc et al. |
| 2016/0200722 | A1 | 7/2016 | DeMong et al. |
| 2018/0072718 | A1 | 3/2018 | Liu et al. |
| 2018/0072719 | A1 | 3/2018 | Ye et al. |
| 2018/0072720 | A1 | 3/2018 | Vechorkin et al. |
| 2018/0072741 | A1 | 3/2018 | Vechorkin et al. |
| 2018/0228786 | A1 | 8/2018 | Sokolsky |
| 2019/0076401 | A1 | 3/2019 | Vechorkin et al. |
| 2019/0106419 | A1 | 4/2019 | Vechorkin et al. |
| 2019/0256500 | A1 | 8/2019 | Vechorkin et al. |
| 2019/0315717 | A1 | 10/2019 | Hummel et al. |
| 2019/0315743 | A1 | 10/2019 | Liu et al. |
| 2019/0343814 | A1 | 11/2019 | Sokolsky |
| 2019/0382380 | A1 | 12/2019 | Vechorkin et al. |
| 2020/0048241 | A1 | 2/2020 | Hummel et al. |

FOREIGN PATENT DOCUMENTS

| | | |
|---|---|---|
| CN | 102516263 | 6/2012 |
| CN | 103570709 | 2/2014 |
| DE | 10 2004 054 666 | 5/2006 |
| EP | 2543372 | 1/2013 |
| EP | 2824099 | 1/2015 |
| IN | 187433 | 4/2002 |
| JP | H03287584 | 12/1991 |
| JP | 2000-038350 | 2/2000 |
| JP | 2007-055940 | 3/2007 |
| JP | 2010-111624 | 5/2010 |
| JP | 2011-246389 | 12/2011 |
| KR | 963644 | 2/1996 |
| KR | 10 2014 0019055 | 2/2014 |
| MX | 9910322 | 7/2003 |
| MY | 146643 | 9/2012 |
| WO | WO 1989/008263 | 9/1989 |
| WO | WO 2000/043394 | 7/2000 |
| WO | WO 2001/019827 | 3/2001 |
| WO | WO 2001/019828 | 3/2001 |
| WO | WO 2001/021576 | 3/2001 |
| WO | WO 2001/046124 | 6/2001 |
| WO | WO 2002/000196 | 1/2002 |
| WO | WO 2002/016348 | 2/2002 |
| WO | WO 2002/019975 | 3/2002 |
| WO | WO 2002/050073 | 6/2002 |
| WO | WO 2002/090347 | 11/2002 |
| WO | WO 2003/037432 | 5/2003 |
| WO | WO 2003/049681 | 6/2003 |
| WO | WO 2004/072069 | 8/2004 |
| WO | WO 2004/096810 | 11/2004 |
| WO | WO 2004/108133 | 12/2004 |
| WO | WO 2005/004799 | 1/2005 |
| WO | WO 2005/011681 | 2/2005 |
| WO | WO 2005/028475 | 3/2005 |
| WO | WO 2005/051906 | 6/2005 |
| WO | WO 2005/066167 | 7/2005 |
| WO | WO 2005/073199 | 8/2005 |
| WO | WO 2005/073232 | 8/2005 |
| WO | WO 2003/101968 | 9/2005 |
| WO | WO 2005/085227 | 9/2005 |
| WO | WO 2005/085248 | 9/2005 |
| WO | WO 2005/085249 | 9/2005 |
| WO | WO 2006/013095 | 2/2006 |
| WO | WO 2006/028958 | 3/2006 |
| WO | WO 2006/038001 | 4/2006 |
| WO | WO 2006/045010 | 4/2006 |
| WO | WO 2006/050097 | 5/2006 |
| WO | WO 2006/053109 | 5/2006 |
| WO | WO 2006/053121 | 5/2006 |
| WO | WO 2006/053227 | 5/2006 |
| WO | WO 2006/074428 | 7/2006 |
| WO | WO 2006/105289 | 10/2006 |
| WO | WO 2006/128172 | 11/2006 |
| WO | WO 2007/019344 | 2/2007 |
| WO | WO 2007/019345 | 2/2007 |
| WO | WO 2007/019346 | 2/2007 |
| WO | WO 2007/019417 | 2/2007 |
| WO | WO 2007/020050 | 2/2007 |
| WO | WO 2007/023110 | 3/2007 |
| WO | WO 2007/023111 | 3/2007 |
| WO | WO 2007/023114 | 3/2007 |
| WO | WO 2007/030582 | 3/2007 |
| WO | WO 2007/056280 | 5/2007 |
| WO | WO 2007/063925 | 6/2007 |
| WO | WO 2007/065924 | 6/2007 |
| WO | WO 2007/080382 | 7/2007 |
| WO | WO 2007/093402 | 8/2007 |
| WO | WO 2007/112093 | 10/2007 |
| WO | WO 2007/114848 | 10/2007 |
| WO | WO 2007/137030 | 11/2007 |
| WO | WO 2008/008059 | 1/2008 |
| WO | WO 2008/008539 | 1/2008 |
| WO | WO 2008/012027 | 1/2008 |
| WO | WO 2008/045627 | 4/2008 |
| WO | WO 2008/070313 | 6/2008 |
| WO | WO 2008/089307 | 7/2008 |
| WO | WO 2008/089310 | 7/2008 |
| WO | WO 2008/113856 | 9/2008 |
| WO | WO 2009/019167 | 2/2009 |
| WO | WO 2009/024341 | 2/2009 |
| WO | WO 2009/032651 | 3/2009 |
| WO | WO 2009/038784 | 3/2009 |
| WO | WO 2009/100130 | 8/2009 |
| WO | WO 2009/139834 | 11/2009 |
| WO | WO 2009/152356 | 12/2009 |
| WO | WO 2010/029300 | 3/2010 |

(56) References Cited

FOREIGN PATENT DOCUMENTS

| | | |
|---|---|---|
| WO | WO 2010/035217 | 4/2010 |
| WO | WO 2010/035219 | 4/2010 |
| WO | WO 2010/035221 | 4/2010 |
| WO | WO 2010/046780 | 4/2010 |
| WO | WO 2010/080503 | 7/2010 |
| WO | WO 2010/104306 | 9/2010 |
| WO | WO 2010/107765 | 9/2010 |
| WO | WO 2010/107768 | 9/2010 |
| WO | WO 2010/111624 | 9/2010 |
| WO | WO 2010/118367 | 10/2010 |
| WO | WO 2011/019780 | 2/2011 |
| WO | WO 2011/031628 | 3/2011 |
| WO | WO 2011/050245 | 4/2011 |
| WO | WO 2011/051535 | 5/2011 |
| WO | WO 2011/062253 | 5/2011 |
| WO | WO 2011/078143 | 6/2011 |
| WO | WO 2011/082400 | 7/2011 |
| WO | WO 2011/082488 | 7/2011 |
| WO | WO 2011/107186 | 9/2011 |
| WO | WO 2011/133920 | 10/2011 |
| WO | WO 2011/139489 | 11/2011 |
| WO | WO 2011/141756 | 11/2011 |
| WO | WO 2011/147765 | 12/2011 |
| WO | WO 2011/153553 | 12/2011 |
| WO | WO 2011/157653 | 12/2011 |
| WO | WO 2011/158108 | 12/2011 |
| WO | WO 2012/048058 | 4/2012 |
| WO | WO 2012/049277 | 4/2012 |
| WO | WO 2012/078777 | 6/2012 |
| WO | WO 2012/080376 | 6/2012 |
| WO | WO 2012/109263 | 8/2012 |
| WO | WO 2012/130780 | 10/2012 |
| WO | WO 2012/141487 | 10/2012 |
| WO | WO 2012/143144 | 10/2012 |
| WO | WO 2012/158810 | 11/2012 |
| WO | WO 2012/163959 | 12/2012 |
| WO | WO 2013/007708 | 1/2013 |
| WO | WO 2013/021276 | 2/2013 |
| WO | WO 2013/024002 | 2/2013 |
| WO | WO 2013/024011 | 2/2013 |
| WO | WO 2013/042137 | 3/2013 |
| WO | WO 2013/064445 | 5/2013 |
| WO | WO 2013/123215 | 8/2013 |
| WO | WO 2013/130890 | 9/2013 |
| WO | WO 2013/146942 | 10/2013 |
| WO | WO 2014/003405 | 1/2014 |
| WO | WO 2014/024125 | 2/2014 |
| WO | WO 2014/047616 | 3/2014 |
| WO | WO 2014/055955 | 4/2014 |
| WO | WO 2014/151616 | 9/2014 |
| WO | WO 2015/026683 | 2/2015 |
| WO | WO 2015/037965 | 3/2015 |
| WO | WO 2015/038503 | 3/2015 |
| WO | WO 2015/058163 | 4/2015 |
| WO | WO 2015/061247 | 4/2015 |
| WO | WO 2015/089327 | 6/2015 |
| WO | WO 2015/089479 | 6/2015 |
| WO | WO 2015/090235 | 6/2015 |
| WO | WO 2015/091426 | 6/2015 |
| WO | WO 2015/104662 | 7/2015 |
| WO | WO 2015/117718 | 8/2015 |
| WO | WO 2015/164956 | 11/2015 |
| WO | WO 2015/192939 | 12/2015 |
| WO | WO 2015/193506 | 12/2015 |
| WO | WO 2015/193846 | 12/2015 |
| WO | WO 2015/200682 | 12/2015 |
| WO | WO 2016/040180 | 3/2016 |
| WO | WO 2016/040181 | 3/2016 |
| WO | WO 2016/041618 | 3/2016 |
| WO | WO 2016/057500 | 4/2016 |
| WO | WO 2016/083433 | 6/2016 |
| WO | WO 2016/090300 | 6/2016 |
| WO | WO 2016/124304 | 8/2016 |
| WO | WO 2016/144351 | 9/2016 |
| WO | WO 2016/144702 | 9/2016 |
| WO | WO 2016/164285 | 10/2016 |
| WO | WO 2016/174183 | 11/2016 |
| WO | WO 2016/205942 | 12/2016 |
| WO | WO 2017/009798 | 1/2017 |
| WO | WO 2017/009806 | 1/2017 |
| WO | WO 2017/023894 | 2/2017 |
| WO | WO 2017/023972 | 2/2017 |
| WO | WO 2017/027400 | 2/2017 |
| WO | WO 2017/045955 | 3/2017 |
| WO | WO 2017/058915 | 4/2017 |
| WO | WO 2017/108744 | 6/2017 |
| ZA | 2003005330 | 7/2003 |

OTHER PUBLICATIONS

Balog et al., "The synthesis and evaluation of [2.2.1]-bicycloazahydantoins as androgen receptor antagonists," Bioorg. Med. Chem. Lett., Dec. 20, 2004, 14(24):6107-6111.

Batliwalla et al., "Microarray analyses of peripheral blood cells identifies unique gene expression signature in psoriatic arthritis," Mol Med, 2005, 11(1-12):21-29.

Berge et al., "Pharmaceutical Salsts," J. Pharm. Sci., 1977, 66(1):1-19.

Blom et al., "Optimizing Preparative LC-MS Configurations and Methods for Parallel Synthesis Purification," J. Combi. Chem., 2003, 5:670.

Blom et al., "Preparative LC-MS Purification: Improved Compound Specific Method Optimization," J. Combi. Chem., 2004, 6:874-883.

Blom et al., "Two-Pump at Column Dilution Configuration for Preparative LC-MS," J. Combi. Chem., 2002, 4: 295.

Chessari et al., "Fragment-Based Drug Discovery Targeting Inhibitor of Apoptosis Proteins: Discovery of a Non-Alanine Lead Series with Dual Activity Against cIAP1 and XIAP," J. Med. Chem., Jul. 18, 2015, 58(16):6574-6588.

Chinchilla and Najera, "Recent advances in Sonogashira reactions," Chem. Soc. Rev., 2011, 40:5084-5121.

Choi et al., "In vitro metabolism of a novel phosphodiesterase-5 inhibitor DA-8159 in rat liver preparations using liquid chromatography/electrospray mass spectrometry," Biomed Chromatogr., Sep. 2002, 16(6):395-399.

Cordovilla et al., "The Stille Reaction, 38 Years Later," ACS Catalysis, 2015, 5: 3040-3053.

Devegowda et al., "Novel 6-N-arylcarboxamidopyrazolo[4,3-d]pyrimidin-7-one derivatives as potential anti-cancer agents," Bioorg Med Chem Lett., Mar. 1, 2010, 20(5):1630-1633.

Di Bartolo et al., "A novel pathway down-modulating T cell activation involves HPK-1-dependent recruitment of 14-3-3 proteins on SLP-76," J. Exp. Med., Mar. 2007, 204(3): 681-691.

Dumestre-Toulet et al., "Last performance with VIAGRA: post-mortem identification of sildenafil and its metabolites in biological specimens including hair sample," Forensic Sci Int., Mar. 28, 2002, 126(1):71-76.

Edmondson et al., "Aminopiperidine-fused imidazoles as dipeptidyl peptidase-IV inhibitors," Bioorg Med Chem Lett., Aug. 2009, 19(15):4097-4101.

Elgemeie et al., "Novel Nucleoside Analogues: First Synthesis of Pyridine-4-Thioglycosides and Their Cytotoxic Evaluation," Nucleosides, Nucleotides and Nucleic Acids, Jun. 27, 2015, 34:659-673.

Elgemeie et al., "Synthesis of Novel Derivatives of 4-Methylthio-N-Aryl-2-Pyridone and Deazapurine Analogues: The Reaction of Ketene Dithioacetals with Substituted Acetanilides," Phosphorus, Sulfur and Silicon, 2000, 164:189-197.

Erian, "2-Aryl-1,1-dicyano-3-phenylsulfonylpropenes in heterocyclic synthesis. A synthetic strategy towards heterocyclic sulfone," Monatshefte fuer Chemie, Oct. 1998, 129(10):1049-1056.

Figueiredo et al., "A chemometric study of phosphodiesterase 5 inhibitors," J Mol Graph Model., Jan. 2006, 24(4):227-232.

Gao, "Slidenafil" Handbook of Metabolic Pathways of Xenobiotics, 2014, 5:2151-2154.

Goodarzi et al., "Feature Selection and Linear/Nonlinear Regression Methods for the Accurate Prediction of Glycogen Synthase Kinase-3β Inhibitory Activities," J. Chem. Inf. Model, 2009, 49(4):824-832.

(56) References Cited

OTHER PUBLICATIONS

Haas et al., "Recent Developments in Negishi Cross-Coupling Reactions," ACS Catalysis, 2016, 6:1540-1552.
Haning et al., "Comparison of different heterocyclic scaffolds as substrate analog PDE5 inhibitors," Sep. 1, 2005, 15(17):3900-3907.
Hanson, "Diterpenoids of Terrestrial Origin", National Product Reports, 2016, 33:1227-1238.
Hu et al., "Human HPK1, a novel human hematopoietic progenitor kinase that activates the JNK/SAPK kinase cascade," Genes Dev, 1996, 10(18): p. 2251-2264.
Ho et al., "Discovery of 4-phenyl-2-phenylaminopyridine based TNIK inhibitors," Boorg Med Chem Lett, 2013, 23(2):569-573.
Howard et al., "Identification of potent phosphodiesterase inhibitors that demonstrate cyclic nucleotide-dependent functions in apicomplexan parasites," ACS Chem Biol., Apr. 17, 2015, 10(4):1145-1154.
Ikegami et al., "The expression of prostaglandin E receptors EP2 and EP4 and their different regulation by lipopolysaccharide in C3H/HeN peritoneal macrophages," J. Immunol., Apr. 2001, 166(7): 4689-4696.
International Search Report and Written Opinion in International Application No. PCT/US2017/048880, dated Nov. 2, 2017, 15 pages.
International Search Report and Written Opinion in International Application No. PCT/US2017/050669, dated Nov. 6, 2017, 16 pages.
International Search Report and Written Opinion in International Application No. PCT/US2017/050727, dated Nov. 2, 2017, 16 pages.
International Search Report and Written Opinion in International Application No. PCT/US2017/050737, dated Nov. 2, 2017, 16 pages.
International Search Report and Written Opinion in International Application No. PCT/US2017/050757, dated Nov. 10, 2017, 20 pages.
International Search Report and Written Opinion in International Application No. PCT/US2018/018205, dated Apr. 30, 2018, 16 pages.
International Search Report and Written Opinion in International Application No. PCT/US2018/049908, dated Nov. 7, 2018.
International Search Report and Written Opinion in International Application No. PCT/US2019/018609, dated May 13, 2019, 12 pages.
International Search Report and Written Opinion in International Application No. PCT/US2019/018608, dated Apr. 16, 2019, 14 pages.
International Preliminary Report on Patentability in International Application No. PCT/US2017/050669, dated Mar. 12, 2019, 8 pages.
International Preliminary Report on Patentability in International Application No. PCT/US2017/050737, dated Mar. 12, 2019, 8 pages.
International Preliminary Report on Patentability in International Application No. PCT/US2017/050727, dated Mar. 12, 2019, 8 pages.
International Preliminary Report on Patentability in International Application No. PCT/US2017/050757, dated Mar. 12, 2019, 10 pages.
International Preliminary Report on Patentability in International Application No. PCT/US2018/018205, dated Aug. 20, 2019, 10 pages.
Ivon et al., "Synthesis of a 2,5-Diazabicyclo[2.2.1]heptane-Derived α,β-Diamino Acid," Synthesis, 2015, 47(8):1123-1130.
Karaman "Analyzing the efficiency in intramolecular amide hydrolysis of Kirby's N-alkylmaleamic acids—A computational approach," Computational and Theoretical Chemistry, 2011, 974(1-3):133-142.
Katritzky et al., "QSAR modeling of the inhibition of Glycogen Synthase Kinase-3," Bioorganic & Medicinal Chemistry, 2006, 14(14):4987-5002.

Kerekes et al., "Aurora kinase inhibitors based on the imidazo[1,2-a]pyrazine core: fluorine and deuterium incorporation improve oral absorption and exposure," J. Med. Chem., Jan. 2011, 54(1): 201-210.
Kiefer et al., "HPK1, a hematopoietic protein kinase activating the SAPK/JNK pathway," EMBO. J., Dec. 1996, 15(24): 7013-7025.
Kim et al., "Reliable screening and confirmation of 156 multi-class illegal adulterants in dietary supplements based on extracted common ion chromatograms by ultra-high-performance liquid chromatography-quadrupole/time of flight-mass spectrometry," J Chromatogr A., Mar. 31, 2017, 1491:43-56.
Kotha et al., "Recent applications of the Suzuki—Miyaura cross-coupling reaction in organic synthesis," Tetrahedron, 2002, 58: 9633-9695.
Kumar et al., "3-(1H-Indol-2-yl)-1H-pyrazolo[4,3-b]pyridines as Wnt pathway modulators and their preparation," retrieved from STN Database Accession No. 2017: 232331, Feb. 9, 2017, Chemical Abstracts Service, Columbus, Ohio, US, XP002775032.
Kumar et al., "3-(1H-Indol-2-yl)-1H-pyrazolo[4,3-b]pyridines as Wnt pathway modulators and their preparation," retrieved from STN Database Accession No. 2017: 232415, Feb. 9, 2017, Chemical Abstracts Service, Columbus, Ohio, US, XP002775031.
Kumar et al., "3-(1H-Indol-2-yl)-1H-pyrazolo[4,3-b]pyridines as Wnt pathway modulators and their preparation," retrieved from STN Database Accession No. 2017: 232564, Feb. 9, 2017, Chemical Abstracts Service, Columbus, Ohio, US, XP002775030.
Kumar et al., "3-(1H-Indol-2-yl)-1H-pyrazolo[4,3-b]pyridines as Wnt pathway modulators and their preparation," retrieved from STN Database Accession No. 2017: 233013, Feb. 9, 2017, Chemical Abstracts Service, Columbus, Ohio, US, XP002775029.
Kumar et al., "3-(1H-Indol-2-yl)-1H-pyrazolo[4,3-b]pyridines as Wnt pathway modulators and their preparation," retrieved from STN Database Accession No. 2017: 233418, Feb. 9, 2017, Chemical Abstracts Service, Columbus, Ohio, US, XP002775028.
Kumar et al., "3-(1H-Indol-2-yl)-1H-pyrazolo[4,3-b]pyridines as Wnt pathway modulators and their preparation," retrieved from STN Database Accession No. 2017: 233427, Feb. 9, 2017, Chemical Abstracts Service, Columbus, Ohio, US, XP002775027.
Kumar et al., "3-(1H-Indol-2-yl)-1H-pyrazolo[4,3-b]pyridines as Wnt pathway modulators and their preparation," retrieved from STN Database Accession No. 2017: 233436, Feb. 9, 2017, Chemical Abstracts Service, Columbus, Ohio, US, XP002775026.
Lebel et al., "A rapid, quantitative liquid chromatography-mass spectrometry screening method for 71 active and 11 natural erectile dysfunction ingredients present in potentially adulterated or counterfeit products," J Chromatogr A., May 23, 2014, 1343:143-151.
Lee et al., "Comparative metabolism of sildenafil in liver microsomes of different species by using LC/MS-based multivariate analysis," J of Chromato., Oct. 15, 2011, 879(28):3005-3011.
Li et al., "Metabolism of aildenafil in vivo in rats and in vitro in mouse, rat, dog, and human liver microsomes," Drug Test Anal., Jun. 2014., 6(6):552-562.
Lim et al., "Discovery of 1-(1 H-Pyrazolo [4,3-c]pyridin-6-yl)urea Inhibitors of Extracellular Signal-Regulated Kinase (ERK) for the Treatment of Cancers," Journal of Medicinal Chemistry, Jul. 2016, 59(13): 6501-6511.
Lin et al., "2,3,4-Trisbustituted pyridines as selective AKT inhibitors. Part II: Improved drug-like properties and kinase selectivity from azaindazoles," Bioorganic & Medicinal Chemistry Letters, 2010, 20: 679-683.
Liou et al., "HPK1 is activated by lymphocyte antigen receptors and negatively regulates AP-1," Immunity, Apr. 2000, 12(4): 399-408.
Liu et al., "Synthesis and SAR of 1,9-dihydro-9-hydroxypyrazolo[3,4-b]quinolin-4-ones as novel, selective c-Jun N-terminal kinase inhibitors," Bioorg Med Chem Lett., May 15, 2006, 16(10):2590-2594.
Michelotti et al., "Two Classes of p38a MAP kinase inhibitors having a common core but exhibiting devergent binding modes," 2005, 15:5274-5279.
Miyazaki et al., "Design and effective synthesis of novel templates, 3,7-diphenyl-4-amino-thieno and furo-[3,2-c]pyridines as protein kinase inhibitors and in vitro evaluation targeting angiogenetic kinases," Bioorg Med Chem Lett., Jan. 1, 2007, 17(1):250-254.

(56) References Cited

OTHER PUBLICATIONS

Mulvihill et al., "Novel 2-phenylquinolin-7-yl-derived imidazo[1,5-a]pyrazines as potent insulin-like growth factor-I receptor (IGF-IR) inhibitors," Bioorg Med Chem Lett, Feb. 2008, 16(3):1359-1375.
Patel et al., "Selectivity criterion for pyrazolo[3,4-b]pyrid[az]ine derivatives as GSK-3 inhibitors: CoMFA and molecular docking studies," European Journal of Medicinal Chemistry, 2008, 43: 949-957.
Peturssion et al., "Protecting Groups in Carbohydrate Chemistry," J. Chem. Educ., 1997, 74(11), 1297.
Piersanti et al., "Synthesis of Benzo[1,2-d;3,4-d']diimidazole and 1H-Pyrazolo[4,3-b]pyridine as Putative A2A Receptor Antagonists," Organic a& Biomolecular Chemistry, Jul. 13, 2007, 5:2567-2571.
Pitt et al., "Heteroaromatic rings of the future," J Med Chem., May 14, 2009, 52(9):2952-2963.
Pozharskii et al., Heterocycles in Life and Society Wiley, 1997, pp. 1-6.
Remington's Pharmaceutical Sciences, 17th Ed., (Mack Publishing Company, Easton, 1985), p. 1418.
Sawasdikosol et al., "HPK1 as a novel target for cancer immunotherapy," Immunologic Research, Apr. 4, 2012, 54(1-3): 262-265.
Sawasdikosol, S. et al., The journal of immunology, 2012. 188(supplement 1): p. 163.
Shaughnessy et al., "Copper-Catalyzed Amination of Aryl and Alkenyl Electrophiles," Organic Reactions, Chapter 1, 2014, 85: 1-668.
Shou et al., "Simple means to alleviate sensitivity loss by trifluoroacetic acid (TFA) mobile phases in the hydrophilic interaction chromatography-electrospray tandem mass spectrometric (HILIC-ESI/MS/MS) bioanalysis of basic compounds," J Chromatogr B Analyt Technol Biomed Life Sci., Oct. 25, 2008, 825:186-192.
Shui et al., "Hematopoietic progenitor kinase 1 negatively regulates T cell receptor signaling and T cell-mediated immune responses," Nat. Immunol., Jan. 2007, 8(1): 84-91.
Smyth et al., "Synthesis and reactivity of 3-amino-1H-pyrazolo[4,3-c]pyridin-4(5H)-ones: development of a novel kinase-focussed library," Tetrahedron, Apr. 2010, 66(15): 2843-2854.
Subramanyam et al., "6-(4-Pyridinyl)-1H-1,2,3-triazolo[4,5-d]-pyrimidin-4(5H)-one: A Structurally Novel Competitive AMPA Receptor Antagonist," J Med Chem., 1995, 38(4):587-589.
Surry and Buchwald, "Dialkylbiaryl Phosphines in Pd-Catalyzed Amination: A User's Guide," Chem. Sci, 2011, 2(1): 27-50.
Taha et al., "Pharmacophore Modeling, Quantitative Structure-Activity Relationship Analysis, and in Silico Screening Reveal Potent Glycogen Synthase Kinase-3β Inhibitory Activities for Cimetidine, Hydroxychloroquine, and Gemifloxacin," J. Med. Chem., 2008, 51(7):2062-2077.
Terrett et al., "Sildenafil (VIAGRATM), a potent and selective inhibitor of type 5 cGMP phosphodiesterase with utility for the treatment of male erectile dysfunction," Bioorg & Med Chem Lett., Aug. 6, 1996, 6(15):1819-1824.
Vaclavik et al., "Single-Laboratory Validation Study of a Method for Screening and Identification of Phosphodiesterase Type 5 Inhibitors in Dietary Ingredients and Supplements Using Liquid Chromatography/Quadrupole-Orbital Ion Trap Mass Spectrometry: First Action 2015.12," J AOAC Int., Jan.-Feb. 2016, 99(1):55-72.
Vymetalova et al., "5-Substituted 3-isopropyl-7-[4-(2-pyridyl)benzyl]amino-1(2)H-pyrazolo [4,3-d]pyrimidines with antiproliferative activity as potent and selective inhibitors of cyclin-dependent kinases," Eur J Med Chem., Mar. 3, 2016, 110:391-301.
Wang et al., "Activation of the hematopoietic progenitor kinase-1 (HPK1)-dependent, stress-activated c-Jun N-terminal kinase (JNK) pathway by transforming growth factor beta (TGF-beta)-activated kinase (TAK1), a kinase mediator of TGF beta signal transduction," J. Biol. Chem., Sep. 1997, 272(36): 22771-22775.
Wang et al., "Down-regulation of B cell receptor signaling by hematopoietic progenitor kinase 1 (HPK-1)-mediated phosphorylation and ubiquitination of activated B cell linker protein (BLNK)," J. Biol. Chem., Mar. 2012, 297(14): 11037-11048.
Wang et al., "Synthesis and evaluation of human phosphodiesterases (PDE) 5 inhibitor analogs as trypanosomal PDE inhibitors. Part 1. Sildenafil analogs," Bioorg Med Chem Lett., Apr. 1, 2012, 22(7):2579-2581.
Weinmann et al., "Identification of lorazepam and sildenafil as examples for the application of LC/ionspray-MS and MS-MS with mass spectra library searching in forensic toxicology," Forensic Sci Int., Sep. 11, 2000, 113(1-3):339-344.
Witherington et al., "5-Aryl-pyrazolo[3,4-b]pyridazines: Potent Inhibitors of Glycogen Synthase Kinase-3 (GSK-3)," Bioorganic & Medicinal Letters, 2003, 13: 1577-1580.
Witherington et al., "5-Aryl-pyrazolo[3,4-b]pyridazines: Potent Inhibitors of Glycogen Synthase Kinase-3 (GSK-3)," Bioorganic & Medicinal Letters, 2003, 13: 1581-1584.
Wislicenus "Adolph Strecker's Short Textbook of Organic Chemistry," 1881, Spottiswood, London, pp. 38-39.
Xu et al., "Design, synthesis and biological evaluation of euterated nintedanib for improving pharmacokinetic properties," J. Labelled Comp. Radiopharm., Jun. 2015, 58(7): 308-312.
Yang et al., "Highly efficient synthesis of fused bicyclic 2,3-diaryl-pyrimidin-4(3H)-ones via Lewis acid assisted cyclization reaction," Tetrahedron Letters, Mar. 10, 2008, 49(11):1725-1728.
Yeo et al., "New metabolites of hongdenafil, homosildenafil and hydroxyhomosildenafil," J Pharm Biomed Anal., Feb. 5, 2018, 149:586-590.
Zhang et al., "Anti-angiogenic effects of novel cyclin-dependent kinase inhibitors with a pyrazolo[4,3-d]pyrimidine scaffold," Br J Pharmacol., Sep. 2016, 173(17):2645-2656.
Zhou et al., "Hematopoietic progenitor kinase 1 is a component of transforming growth factor beta-induced c-Jun N-terminal kinase signaling cascade," J. Biol. Chem., May 1999, 274(19): 13133-13138.
Zhu et al., "Design and Synthesis of Pyridine-pyrazolopyridine based inhibitors of protein kinase B/Akt," Bioorganic and Medicinal Chemistry, Jan. 17, 2007, 15: 2441-2452.
Zhu et al., "Characterization of TPN729 metabolites in humans using ultra-performance liquid chromatography/quadrupole time-of-flight mass spectrometry," J Pharm Biomed Anal., Jan. 5, 2016, 117:217-226.
Literature and Patent Chemical Structure Search, Science IP, The CAS Search Service, Jul. 1, 2016, 441 pages.
Literature and Patent Chemical Structure Search, Science IP, The CAS Search Service, Jun. 30, 2016, 200 pages.
Structure 4: Substance Search Patent and Non-Patent Databases, Science IP, The CAS Search Service, Jun. 8, 2016, 820 pages.
Structure 3: Substance Search Patent and Non-Patent Databases, Science IP, The CAS Search Service, Jun. 7, 2016, 512 pages.
Structure 2: Substance Search Patent and Non-Patent Databases, Science IP, The CAS Search Service, Jun. 7, 2016, 833 pages.
Structure 1: Substance Search Patent and Non-Patent Databases, Science IP, The CAS Search Service, Jun. 6, 2016, 583 pages.
STN Search Report dated Aug. 17, 2016, 157 pages.
STN Search Report dated Aug. 25, 2016, 25 pages.
STN Search Report dated Aug. 30, 2016, 31 pages.
STN Search Report dated Aug. 31, 2016, 32 pages.
STN Search Report dated Jan. 27, 2017, 94 pages.
STN Search Report dated on Jan. 23, 2018, 26 pages.
STN Search Report dated on Apr. 25, 2018, 19 pages.
STN Search Report dated on May 9, 2018, 16 pages.
Anonymous, "Crystalline ethyl 1-(4-methoxyphenyl)-6-(4-nitrophenyl)-7-oxo-,5,6,7-tetrahydro-1H-pyrazolo[3,4-c]pyridine-3-carboxylate," IP.com #IPCOM000233229D, Dec. 3, 2019, 4 pages.
Anonymous, "Crystalline APX," IP.com #IPCOM000233879, Dec. 25, 2013, 3 pages.
Ballell et al., "Fueling Open-Source Drug Discovery: 177 Small-Molecule Leads against Tuberculosis," ChemMedChem., 2013, 8(2):313-321.
Brioche et al., "Chiral Phosphoric Acid-Catalyzed Enantioselective Three-Component Aza-Diels-Alder Reactions of Aminopyrroles and Aminopyrazoles," Advanced Synthesis & Catalysis, 2014, 356(8):1719-1724.
Cheung et al., "A Parallel Synthesis Approach to the Identification of Novel Diheteroarylamide-Based Compounds Blocking HIV Rep-

(56) References Cited

OTHER PUBLICATIONS lication: Potential Inhibitors of HIV-1 Pre-mRNA Alternative Splicing," J Med Chem., Mar. 10, 2016, 59(5):1869-1879.
Dong et al., "Pharmacophore identification, virtual screening and biological evaluation of prenylated flavonoids derivatives as PKB/Akt1 inhibitors," Eur J Med Chem., Dec. 2011, 46(12):5949-5958.
Dong et al., "QSAR study of Akt/protein kinase B (PKB) inhibitors using support vector machine," Eur J Med Chem., Oct. 2009, 44(10):4090-4097.
Dornow et al., "Syntheses of nitrogen-containing heterocycles. XXXVIII. Preparation and reaction of several substituted 3-nitropyridines," Chemische Berichte, 1966, 99(1):244-253 (Machine Translation).
El-Aziz et al., "Synthesis and in vitro anti-breast cancer activity of some novel 1,4-dihydropyridine derivatives," Int J of Pharm Pharma. Sci., 2013, 5(Suppl. 3):183-189.
El Sayed et al., "New route for the preparation of pyrazolo[4,3-c]pyridines," Bulletin of the Chemical Society of Japan (1973), 46(6), 1801-1803.
Elgemeie et al., "A new general method for substituted 4-alkylthio-N-arylsulfonylamino-2-pyridones: Reaction of ketene-S,S-acetals with arylsulfonylhydrazides," Phosphorus, Sulfur and Silicon and the Related Elements, 2001, 170:171-179.
Elgemeie et al., "Novel N-Substituted Amino-4-methylsulfanyl-2-pyridones and Deazapurine Analogues from Ketene Dithioacetals," J Chem Res., 1998, 3:164-165.
Elgemeie et al., "Novel synthesis of N-aroylaminated pyridones via reaction of ketene dithioacetals with cyanoaceto-N-aroylhydrazides," Synth Comm., 2003, 33(2):253-258.
He et al., "Predicting the Genotoxicity of Polycyclic Aromatic Compounds from Molecular Structure with Different Classifiers," Chemical Research in Toxicology (2003), 16(12):1567-1580.
Hu et al., "Discovery of 3,5-substituted 6-azaindazoles as potent pan-Pim inhibitors," Bioorg Med Chem Lett., 2015, 25(22):5258-5264.
Li et al., "A highly effective one-pot synthesis of quinolines from o-nitroarylcarbaldehydes," Organic & Biomolecular Chemistry, 2007, 5(1):61-64.
Li et al., "One-pot Friedlander quinoline synthesis: scope and limitations," Synthesis, 2010, 10:1678-1686.
Lin et al., "Tetrasubstituted pyridines as potent and selective AKT inhibitors: Reduced CYP450 and hERG inhibition of aminopyridines," Bioorg Med Chem Lett. Jan. 15, 2010;20(2):684-688.
Muddassar et al., "Elucidation of binding mode and three dimensional quantitative structure-activity relationship studies of a novel series of protein kinase B/Akt inhibitors," J Mol Model., Feb. 2009, 15(2):183-192.
Waddell et al., "Benzothiazolylthio Carbapenems: Potent Anti-MRSA Agents," Biorg & Med Chem Lett., 1995, 5(13):1427-1432.
Wang et al., "Fragment-based identification and optimization of a class of potent pyrrolo [2,1-f][1,2,4]triazine MAP4K4 inhibitors," Boorg Med Chem Lett., 2014, 24(18):4546-4552.
Zhu et al., "Syntheses of potent, selective, and orally bioavailable indazole-pyridine series of protein kinase B/Akt inhibitors with reduced hypotension," J Med Chem., Jun. 28, 2007, 50(13):2990-3003.
STN Search Report dated Sep. 5, 2017, 26 pages.
STN Search Report dated Sep. 5, 2017, 5 pages.
STN Search Report dated Apr. 9, 2018, 7 pages.

INDAZOLE COMPOUNDS AND USES THEREOF

CROSS REFERENCE TO RELATED APPLICATIONS

This application claims the benefit of U.S. Provisional Application No. 62/775,989 filed Dec. 6, 2018; U.S. Provisional Application No. 62/659,342 filed Apr. 18, 2018; and U.S. Provisional Application No. 62/632,688 filed Feb. 20, 2018; each of which is incorporated by reference in its entirety.

FIELD OF THE INVENTION

The disclosure provides compounds as well as their compositions and methods of use. The compounds modulate hematopoietic progenitor kinase 1 (HPK1) activity and are useful in the treatment of various diseases including cancer.

BACKGROUND OF THE INVENTION

Hematopoietic progenitor kinase 1 (HPK1) originally cloned from hematopoietic progenitor cells is a member of MAP kinase kinase kinase kinases (MAP4Ks) family, which includes MAP4K1/HPK1, MAP4K2/GCK, MAP4K3/GLK, MAP4K4/HGK, MAP4K5/KHS, and MAP4K6/MINK (Hu, M. C., et al., Genes Dev, 1996. 10(18): p. 2251-64). HPK1 is of particular interest because it is predominantly expressed in hematopoietic cells such as T cells, B cells, macrophages, dendritic cells, neutrophils, and mast cells (Hu, M. C., et al., Genes Dev, 1996. 10(18): p. 2251-64; Kiefer, F., et al., EMBO J, 1996. 15(24): p. 7013-25). HPK1 kinase activity has been shown to be induced upon activation of T cell receptors (TCR) (Liou, J., et al., Immunity, 2000. 12(4): p. 399-408), B cell receptors (BCR) (Liou, J., et al., Immunity, 2000. 12(4): p. 399-408), transforming growth factor receptor (TGF-βR) (Wang, W., et al., J Biol Chem, 1997. 272(36): p. 22771-5; Zhou, G., et al., J Biol Chem, 1999. 274(19): p. 13133-8), or $G_s$-coupled $PGE_2$ receptors (EP2 and EP4) (Ikegami, R., et al., J Immunol, 2001. 166(7): p. 4689-96). As such, HPK1 regulates diverse functions of various immune cells.

HPK1 is important in regulating the functions of various immune cells and it has been implicated in autoimmune diseases and anti-tumor immunity (Shui, J. W., et al., Nat Immunol, 2007. 8(1): p. 84-91; Wang, X., et al., J Biol Chem, 2012. 287(14): p. 11037-48). HPK1 knockout mice were more susceptible to the induction of experimental autoimmune encephalomyelitis (EAE) (Shui, J. W., et al., Nat Immunol, 2007. 8(1): p. 84-91). In human, HPK1 was downregulated in peripheral blood mononuclear cells of psoriatic arthritis patients or T cells of systemic lupus erythematosus (SLE) patients (Batliwalla, F. M., et al., Mol Med, 2005. 11(1-12): p. 21-9). Those observations suggested that attenuation of HPK1 activity may contribute to autoimmunity in patients. Furthermore, HPK1 may also control anti-tumor immunity via T cell-dependent mechanisms. In the PGE2-producing Lewis lung carcinoma tumor model, the tumors developed more slowly in HPK1 knockout mice as compared to wild-type mice (see US 2007/0087988). In addition, it was shown that adoptive transfer of HPK1 deficient T cells was more effective in controlling tumor growth and metastasis than wild-type T cells (Alzabin, S., et al., Cancer Immunol Immunother, 2010. 59(3): p. 419-29). Similarly, BMDCs from HPK1 knockout mice were more efficient to mount a T cell response to eradicate Lewis lung carcinoma as compared to wild-type BMDCs (Alzabin, S., et al., J Immunol, 2009. 182(10): p. 6187-94). These data, in conjunction with the restricted expression of HPK1 in hematopoietic cells and lack of effect on the normal development of immune cells, suggest that HPK1 is a drug target for enhancing antitumor immunity. Accordingly, there is a need for new compounds that modulate HPK1 activity.

SUMMARY

The present disclosure provides, inter alia, a compound of Formula (I):

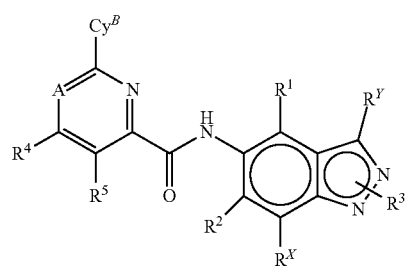

or a pharmaceutically acceptable salt thereof, wherein constituent variables are defined herein.

The present disclosure further provides a pharmaceutical composition comprising a compound of the disclosure, or a pharmaceutically acceptable salt thereof, and at least one pharmaceutically acceptable carrier or excipient.

The present disclosure further provides methods of inhibiting HPK1 activity, which comprises administering to an individual a compound of the disclosure, or a pharmaceutically acceptable salt thereof. The present disclosure also provides uses of the compounds described herein in the manufacture of a medicament for use in therapy. The present disclosure also provides the compounds described herein for use in therapy.

The present disclosure further provides methods of treating a disease or disorder in a patient comprising administering to the patient a therapeutically effective amount of a compound of the disclosure, or a pharmaceutically acceptable salt thereof.

DETAILED DESCRIPTION

Compounds

The present disclosure provides a compound of Formula (I):

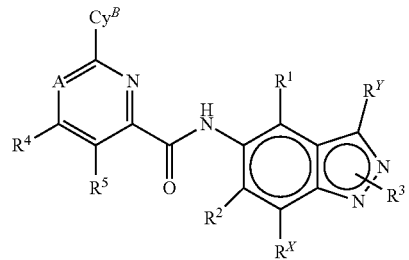

or a pharmaceutically acceptable salt thereof, wherein:

$R^1$ is selected from $Cy^1$, $C_{2-6}$ alkenyl, $C_{2-6}$ alkynyl, $C_{1-6}$ haloalkyl, CN, $NO_2$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NOR^a)R^b$, $C(=NR^e)NR^cR^d$, $-NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, $S(O)_2NR^cR^d$ and $BR^{h}R^{i}$; wherein said $C_{2-6}$ alkenyl and $C_{2-6}$ alkynyl are each optionally substituted with 1, 2, 3, or 4 substituents independently selected from $R^{10}$;

$Cy^1$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

$R^2$ is selected from H, D, $C_{1-6}$ alkyl, $C_{2-6}$ alkenyl, $C_{2-6}$ alkynyl, $C_{1-6}$ haloalkyl, CN, $NO_2$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl and $C_{2-6}$ alkynyl are each optionally substituted with 1, 2, 3, or 4 substituents independently selected from $R^{g2}$;

$R^3$ is selected from $Cy^3$, $C_{1-6}$ alkyl, $C_{2-6}$ alkenyl, $C_{2-6}$ alkynyl, $C_{1-6}$ haloalkyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NOR^{a3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and $BR^{h3}R^{13}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$;

$R^X$ is selected from H, D, $Cy^4$, $C_{1-6}$ alkyl, $C_{2-6}$ alkenyl, $C_{2-6}$ alkynyl, $C_{1-6}$ haloalkyl, halo, CN, $NO_2$, $OR^{v1}$, $SR^{v1}$, $C(O)R^{w1}$, $C(O)NR^{x1}R^{y1}$, $C(O)OR^{x1}$, $OC(O)R^{w1}$, $OC(O)NR^{x1}R^{y1}$, $NR^{x1}R^{y1}$, $NR^{x1}C(O)R^{w1}$, $NR^{x1}C(O)OR^{v1}$, $NR^{x1}C(O)NR^{x1}R^{y1}$, $C(=NR^{z1})R^{w1}$, $C(=NOR^{v1})R^{w1}$, $C(=NR^{z1})NR^{x1}R^{y1}$, $NR^{x1}C(=NR^{z1})NR^{x1}R^{y1}$, $NR^{x1}S(O)R^{w1}$, $NR^{x1}S(O)_2R^{w1}$, $NR^{x1}S(O)_2NR^{x1}R^{y1}$, $S(O)R^{w1}$, $S(O)NR^{x1}R^{y1}$, $S(O)_2R^{w1}$, $S(O)_2NR^{x1}R^{y1}$ and $BR^{t1}R^{u1}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$;

$R^Y$ is selected from H, D, $Cy^5$, $C_{1-6}$ alkyl, $C_{2-6}$ alkenyl, $C_{2-6}$ alkynyl, $C_{1-6}$ haloalkyl, halo, CN, $NO_2$, $OR^{v2}$, $SR^{v2}$, $C(O)R^{w2}$, $C(O)NR^{x2}R^{y2}$, $C(O)OR^{x2}$, $OC(O)R^{w2}$, $OC(O)NR^{x2}R^{y2}$, $NR^{x2}R^{y2}$, $NR^{x2}C(O)R^{w2}$, $NR^{x2}C(O)OR^{v2}$, $NR^{x2}C(O)NR^{x2}R^{y2}$, $C(=NR^{z2})R^{w2}$, $C(=NOR^{v2})R^{w2}$, $C(=NR^{z2})NR^{x2}R^{y2}$, $NR^{x2}C(=NR^{z2})NR^{x2}R^{y2}$, $NR^{x2}S(O)R^{w2}$, $NR^{x2}S(O)_2R^{w2}$, $NR^{x2}S(O)_2NR^{x2}R^{y2}$, $S(O)R^{w2}$, $S(O)NR^{x2}R^{y2}$, $S(O)_2R^{w2}$, $S(O)_2NR^{x2}R^{y2}$ and $BR^{t2}R^{u2}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$;

wherein at least one of $R^X$ and $R^Y$ is other than H or D;

$Cy^3$, $Cy^4$, and $Cy^5$ are each independently selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

$Cy^B$ is selected from $C_{3-10}$ cycloalkyl, 4-10 membered heterocycloalkyl, $C_{6-10}$ aryl and 5-6 membered heteroaryl; wherein the 4-10 membered heterocycloalkyl and 5-6 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of the 5-6 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-6 membered heteroaryl are each optionally substituted with 1, 2, 3, or 4 substituents independently selected from $R^7$;

A is N or $CR^4$;

$R^A$ is selected from H, D, $C_{1-6}$ alkyl, $C_{2-6}$ alkenyl, $C_{2-6}$ alkynyl, $C_{1-6}$ haloalkyl, halo, CN, $NO_2$, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)OR^{a6}$, $NR^{c6}C(O)NR^{c6}R^{d6}$, $NR^{c6}S(O)R^{b6}$, $NR^{c6}S(O)_2R^{b6}$, $NR^{c6}S(O)_2NR^{c6}R^{d6}$ $S(O)R^{b6}$, $S(O)NR^{c6}R^{d6}$, $S(O)_2R^{b6}$, and $S(O)_2NR^{c6}R^{d6}$; wherein said $C_{1-6}$ alkyl, $C_{2-6}$ alkenyl and $C_{2-6}$ alkynyl are each optionally substituted with 1, 2, 3, or 4 substituents independently selected from $R^g$;

$R^4$ is selected from H, D, $C_{1-6}$ alkyl, $C_{2-6}$ alkenyl, $C_{2-6}$ alkynyl, $C_{1-6}$ haloalkyl, CN, $NO_2$, $OR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl and $C_{2-6}$ alkynyl are each optionally substituted with 1, 2, 3, or 4 substituents independently selected from $R^{g4}$;

$R^5$ is selected from H, D, $C_{1-6}$ alkyl, $C_{2-6}$ alkenyl, $C_{2-6}$ alkynyl, $C_{1-6}$ haloalkyl, halo, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $-NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^7$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $C(=NR^{e7})R^{b7}$, $C(=NOR^{a7})R^{b7}$, $C(=NR^{e7})NR^{c7}R^{d7}$, $NR^{c7}C(=NR^{e7})NR^{c7}R^{d7}$, $-NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$ and $BR^{h7}R^{17}$;

wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^8$;

each $R^8$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a8}$, $SR^{a8}$, $C(O)R^{b8}$, $C(O)NR^{c8}R^{d8}$, $C(O)OR^{a8}$, $NR^{c8}R^{d8}$, $NR^{c8}C(O)R^{b8}$, $NR^{c8}C(O)OR^{a8}$, $NR^{c8}S(O)R^{b8}$, $NR^{c8}S(O)_2R^{b8}$, $NR^{c8}S(O)_2NR^{c8}R^{d8}$, $S(O)R^{b8}$, $S(O)NR^{c8}R^{d8}$, $S(O)_2R^{b8}$, $S(O)_2NR^{c8}R^{d8}$ and $BR^{h8}R^{i8}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^9$;

each $R^9$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a9}$, $SR^{a9}$, $C(O)R^{b9}$, $C(O)NR^{c9}R^{d9}$, $C(O)OR^{a9}$, $NR^{c9}R^{d9}$, $NR^{c9}C(O)R^{b9}$, $NR^{c9}C(O)OR^{a9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, and $S(O)_2NR^{c9}R^{d9}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$ and $BR^{h1}R^{i1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a11}$, $SR^{a11}$, $C(O)R^{b11}$, $C(O)NR^{c11}R^{d11}$, $C(O)OR^{a11}$, $NR^{c11}R^{d11}$, $NR^{11}C(O)R^{b11}$, $NR^{c11}C(O)OR^{a11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$ and $BR^{h11}R^{i11}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-10 membered heteroaryl, 4-7 membered heterocycloalkyl, halo, D, CN, $OR^{a12}$, $SR^{a12}$, $C(O)R^{b12}$, $C(O)NR^{c12}R^{d12}$, $C(O)OR^{a12}$, $NR^{c12}R^{d12}$, $NR^{c12}C(O)R^{b12}$, $NR^{c12}C(O)OR^{a12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$ and $BR^{h12}R^{i12}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl are each optionally substituted with 1, 2, 3, or 4 substituents independently selected from $R^g$;

each $R^{13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a13}$, $SR^{a13}$, $C(O)R^{b13}$, $C(O)NR^{c13}R^{d13}$, $C(O)OR^{a13}$, $OC(O)R^{b13}$, $OC(O)NR^{c13}R^{d13}$, $NR^{c13}R^{d13}$, $NR^{c13}C(O)R^{b13}$, $NR^{c13}C(O)OR^{a13}$, $NR^{c13}C(O)NR^{c13}R^{d13}$, $C(=NR^{e13})R^{b13}$, $C(=NOR^{a13})R^{b13}$, $C(=NR^{e13})NR^{c13}R^{d13}$, $NR^{c13}C(=NR^{e13})NR^{c13}R^{d13}$, $NR^{c13}S(O)R^{b13}$, $NR^{c13}S(O)_2R^{b13}$, $NR^{c13}S(O)_2NR^{c13}R^{d13}$, $-S(O)R^{b13}$, $S(O)NR^{c13}R^{d13}$, $S(O)_2R^{b13}$, $S(O)_2NR^{c13}R^{d13}$ and $BR^{h13}R^{i13}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{14}$;

each $R^{14}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a14}$, $SR^{a14}$, $C(O)R^{b14}$, $C(O)NR^{c14}R^{d14}$, $C(O)OR^{a14}$, $NR^{c14}R^{d14}$, $NR^{c14}C(O)R^{b14}$, $NR^{c14}C(O)OR^{a14}$, $NR^{c14}S(O)R^{b14}$, $NR^{c14}S(O)_2R^{b14}$, $NR^{c14}S(O)_2NR^{c14}R^{d14}$, $S(O)R^{b14}$, $S(O)NR^{c14}R^{d14}$, $S(O)_2R^{b14}$, $S(O)_2NR^{c14}R^{d14}$ and $BR^{h14}R^{i14}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{15}$;

each $R^{15}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a15}$, $SR^{a15}$, $C(O)R^{b15}$, $C(O)NR^{c15}R^{d15}$, $C(O)OR^{a15}$, $NR^{c15}R^{d15}$, $NR^{c15}C(O)R^{b15}$, $NR^{c15}C(O)OR^{a15}$, $NR^{c15}S(O)R^{b15}$, $NR^{c15}S(O)_2R^{b15}$, $NR^{c15}S(O)_2NR^{c15}R^{d15}$, $S(O)R^{b15}$, $S(O)NR^{c15}R^{d15}$, $S(O)_2R^{b15}$, and $S(O)_2NR^{c15}R^{d15}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^a$, $R^c$, and $R^d$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3, or 4 substituents independently selected from $R^{10}$;

each $R^b$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^h$ and $R^i$ is independently selected from OH and $C_{1-6}$ alkoxy;

or any $R^h$ and $R^i$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h1}$ and $R^{i1}$ is independently selected from OH and $C_{1-6}$ alkoxy;

or any $R^{h1}$ and $R^{i1}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a2}$, $R^{c2}$ and $R^{d2}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b2}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

or any $R^{c3}$ and $R^{d3}$ attached to the same N atom, together with the N atom to which they are attached, form a 4-, 5-, 6- or 7-membered heterocycloalkyl group optionally substituted with 1, 2, 3, or 4 substituents independently selected from $R^{13}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^{e3}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h3}$ and $R^{i3}$ is independently selected from OH and $C_{1-6}$ alkoxy;

or any $R^{h3}$ and $R^{i3}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a4}$, $R^{c4}$ and $R^{d4}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b4}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a5}$, $R^{c5}$ and $R^{d5}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b5}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a6}$, $R^{c6}$ and $R^{d6}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b6}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a7}$, $R^{c7}$ and $R^{d7}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

or any $R^{c7}$ and $R^{d7}$ attached to the same N atom, together with the N atom to which they are attached, form a 4-, 5-, 6- or 7-membered heterocycloalkyl group optionally substituted with 1, 2, 3, or 4 substituents independently selected from $R^8$;

each $R^{b7}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

each $R^{e7}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h7}$ and $R^{i7}$ is independently selected from OH and $C_{1-6}$ alkoxy;

or any $R^{h7}$ and $R^{i7}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a8}$, $R^{c8}$ and $R^{d8}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^9$;

or any $R^{c8}$ and $R^{d8}$ attached to the same N atom, together with the N atom to which they are attached, form a 4-, 5-, 6- or 7-membered heterocycloalkyl group optionally substituted with 1, 2, 3, or 4 substituents independently selected from $R^9$;

each $R^{b8}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^9$;

each $R^{h8}$ and $R^{i8}$ is independently selected from OH and $C_{1-6}$ alkoxy;

or any $R^{h8}$ and $R^{i8}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a9}$, $R^{c9}$ and $R^{d9}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b9}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a11}$, $R^{c11}$ and $R^{d11}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c11}$ and $R^{d11}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b11}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

each $R^{h11}$ and $R^{i11}$ is independently selected from OH and $C_{1-6}$ alkoxy;

or any $R^{h11}$ and $R^{i11}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a12}$, $R^{c12}$ and $R^{d12}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b12}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl $C_{2-6}$ alkenyl and $C_{2-6}$ alkynyl are each optionally substituted with 1, 2, 3, or 4 substituents independently selected from $R^g$;

each $R^{h12}$ and $R^{i12}$ is independently selected from OH and $C_{1-6}$ alkoxy;

or any $R^{h12}$ and $R^{i12}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a13}$, $R^{c13}$ and $R^{d13}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{14}$;

or any $R^{c13}$ and $R^{d13}$ attached to the same N atom, together with the N atom to which they are attached, form a 4-, 5-, 6- or 7-membered heterocycloalkyl group optionally substituted with 1, 2, 3, or 4 substituents independently selected from $R^{14}$;

each $R^{b13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{14}$;

each $R^{e13}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h13}$ and $R^{i13}$ is independently selected from OH and $C_{1-6}$ alkoxy;

or any $R^{h13}$ and $R^{i13}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a14}$, $R^{c14}$ and $R^{d14}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{15}$;

or any $R^{c14}$ and $R^{d14}$ attached to the same N atom, together with the N atom to which they are attached, form a 4-, 5-, 6- or 7-membered heterocycloalkyl group optionally substituted with 1, 2, 3, or 4 substituents independently selected from $R^{15}$;

each $R^{b14}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{15}$;

each $R^{h14}$ and $R^{i14}$ is independently selected from OH and $C_{1-6}$ alkoxy;

or any $R^{h14}$ and $R^{i14}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a15}$, $R^{c15}$ and $R^{d15}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b15}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{v1}$, $R^{x1}$, and $R^{y1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

or any $R^{x1}$ and $R^{y1}$ attached to the same N atom, together with the N atom to which they are attached, form a 4-10 membered heterocycloalkyl group optionally substituted with 1, 2, 3, or 4 substituents independently selected from $R^{13}$;

each $R^{w1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^{z1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{t1}$ and $R^{u1}$ is independently selected from OH and $C_{1-6}$ alkoxy;

or any $R^{t1}$ and $R^{u1}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{v2}$, $R^{x2}$, and $R^{y2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

or any $R^{x2}$ and $R^{y2}$ attached to the same N atom, together with the N atom to which they are attached, form a 4-10 membered heterocycloalkyl group optionally substituted with 1, 2, 3, or 4 substituents independently selected from $R^{13}$;

each $R^{w2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^{z2}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{t2}$ and $R^{u2}$ is independently selected from OH and $C_{1-6}$ alkoxy;

or any $R^{t2}$ and $R^{u2}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^{g2}$ is independently selected from $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and each $R^{g4}$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, provided herein is a compound of Formula (I), or a pharmaceutically acceptable salt thereof, wherein $R^1$ is selected from $Cy^1$ and $NR^cR^d$;

$Cy^1$ is selected from 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of the 5-10 membered heteroaryl and 4-10 membered heterocycloalkyl is optionally substituted by oxo to form a carbonyl group; and wherein the 4-10 membered heterocycloalkyl, $C_{6-10}$ aryl and 5-10 membered heteroaryl are each optionally substituted with 1, 2, 3, or 4 substituents independently selected from $R^{10}$;

$R^2$ is H;

$R^3$ is selected from $Cy^3$, $C_{1-6}$ alkyl, $C_{2-6}$ alkenyl, $C_{2-6}$ alkynyl, $C_{1-6}$ haloalkyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$;

$R^X$ is selected from H, D, $C_{1-6}$ alkyl, CN, halo, $C(O)NR^{x1}R^{y1}$, and $Cy^4$; wherein said $C_{1-6}$ alkyl is optionally substituted with 1, 2, 3, or 4 substituents independently selected from $R^{13}$;

$R^Y$ is selected from H, D, $C_{1-6}$ alkyl, CN, halo, $C(O)NR^{x2}R^{y2}$, and $Cy^5$; wherein said $C_{1-6}$ alkyl is optionally substituted with 1, 2, 3, or 4 substituents independently selected from $R^{13}$;

wherein at least one of $R^X$ and $R^Y$ is other than H or D;

$Cy^3$, $Cy^4$, and $Cy^5$ are each independently is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of the 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

$Cy^B$ is phenyl optionally substituted with 1, 2, 3, or 4 substituents independently selected from $R^7$;

A is N or $CR^A$;

$R^A$ is H or $C_{1-3}$ alkyl;

$R^4$ is H;

$R^5$ is H;

each $R^7$ is independently selected from $C_{1-6}$ alkyl, $C_{2-6}$ alkenyl, $C_{2-6}$ alkynyl, $C_{1-6}$ haloalkyl, 5-10 membered heteroaryl, halo, D, CN, $NO_2$, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^a$, $NR^{c7}C(O)NR^{c7}R^{d7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$ and $S(O)_2NR^{c7}R^{d7}$; wherein said $C_{1-6}$ alkyl, $C_{2-6}$ alkenyl, $C_{2-6}$ alkynyl, are each optionally substituted with 1, 2, 3, or 4 substituents independently selected from $R^8$;

each $R^8$ is independently selected from $C_{1-6}$ alkyl, $C_{1-6}$ haloalkyl, halo, D, CN, $OR^{a8}$, $SR^{a8}$, $C(O)R^{b8}$, $C(O)NR^{c8}R^{d8}$, $C(O)OR^{a8}$, $NR^{c8}R^{d8}$, $NR^{c8}C(O)R^{b8}$, $S(O)_2R^{b8}$ and $S(O)_2NR^{c8}R^{d8}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a11}$, $SR^{a11}$, $C(O)R^{b11}$, $C(O)NR^{c11}R^{d11}$, $C(O)OR^{a11}$, $NR^{c11}R^{d11}$, $NR^{c11}C(O)R^{b11}$, $NR^{c11}C(O)OR^{a11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$ and $S(O)_2NR^{c11}R^{d11}$;

each $R^{13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a13}$, $SR^{a13}$, $C(O)R^{b13}$, $C(O)NR^{c3}R^{d13}$, $C(O)OR^{a13}$, $OC(O)R^{b13}$, $OC(O)NR^{c13}R^{d13}$, $NR^{c13}R^{d13}$, $NR^{c13}C(O)R^{b13}$, $NR^{c13}C(O)OR^{a13}$, $NR^{c13}C(O)NR^{c13}R^{d13}$, $NR^{c13}S(O)R^{b13}$, $NR^{c13}S(O)_2R^{b13}$, $NR^{c13}S(O)_2NR^{c13}R^{d13}$, $S(O)R^{b13}$, $S(O)NR^{c3}R^{d13}$, $S(O)_2R^{b13}$ and $S(O)_2NR^{c13}R^{d13}$;

each $R^a$, $R^c$, and $R^d$ is independently selected from H, $C_{1-6}$ alkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

each $R^{a3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^{a7}$, $R^{c7}$ and $R^{d7}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

or any $R^{c7}$ and $R^{d7}$ attached to the same N atom, together with the N atom to which they are attached, form a 4-, 5-, 6- or 7-membered heterocycloalkyl group optionally substituted with 1, 2, 3, or 4 substituents independently selected from $R^8$;

each $R^{b7}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

each $R^{a8}$, $R^{c8}$ and $R^{d8}$ is independently selected from H, $C_{1-6}$ alkyl and $C_{1-6}$ haloalkyl;

each $R^{b8}$ is independently selected from $C_{1-6}$ alkyl and $C_{1-6}$ haloalkyl;

each $R^{a11}$, $R^{c11}$ and $R^{d11}$ is independently selected from H, $C_{1-6}$ alkyl and $C_{1-6}$ haloalkyl;

each $R^{b11}$ is independently selected from $C_{1-6}$ alkyl and $C_{1-6}$ haloalkyl;

each $R^{a13}$, $R^{c13}$ and $R^{d13}$ is independently selected from H, $C_{1-6}$ alkyl and $C_{1-6}$ haloalkyl;

each $R^{b13}$ is independently selected from $C_{1-6}$ alkyl and $C_{1-6}$ haloalkyl; and each $R^{x1}$, $R^{y1}$, $R^{x2}$, and $R^{y2}$ is independently selected from H and $C_{1-6}$ alkyl.

In some embodiments, provided herein is a compound of Formula (I), or a pharmaceutically acceptable salt thereof, wherein $R^1$ is $Cy^1$;

$Cy^1$ is selected from 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of the 5-10 membered heteroaryl and 4-10 membered heterocycloalkyl is optionally substituted by oxo to form a carbonyl group; and wherein the 4-10 membered heterocycloalkyl, $C_{6-10}$ aryl and 5-10 membered heteroaryl are each optionally substituted with 1, 2, 3, or 4 substituents independently selected from $R^{10}$;

$R^2$ is H;

$R^3$ is selected from $Cy^3$, $C_{1-6}$ alkyl, $C_{2-6}$ alkenyl, $C_{2-6}$ alkynyl, $C_{1-6}$ haloalkyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$;

$R^X$ is selected from H, D, $C_{1-6}$ alkyl, CN, halo, $C(O)NR^{x1}R^{y1}$, and $Cy^4$; wherein said $C_{1-6}$ alkyl is optionally substituted with 1, 2, 3, or 4 substituents independently selected from $R^{13}$;

$R^Y$ is selected from H, D, $C_{1-6}$ alkyl, CN, halo, $C(O)NR^{x2}R^{y2}$, and $Cy^5$; wherein said $C_{1-6}$ alkyl is optionally substituted with 1, 2, 3, or 4 substituents independently selected from $R^{13}$;

wherein at least one of $R^X$ and $R^Y$ is other than H or D;

$Cy^3$, $Cy^4$, and $Cy^5$ are each independently is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of the 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

$Cy^B$ is phenyl optionally substituted with 1, 2, 3, or 4 substituents independently selected from $R^7$;

A is N;

$R^4$ is H;

$R^5$ is H;

each $R^7$ is independently selected from $C_{1-6}$ alkyl, $C_{2-6}$ alkenyl, $C_{2-6}$ alkynyl, $C_{1-6}$ haloalkyl, halo, D, CN, $NO_2$, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$ and $S(O)_2NR^{c7}R^{d7}$; wherein said $C_{1-6}$ alkyl, $C_{2-6}$ alkenyl, $C_{2-6}$ alkynyl, are each optionally substituted with 1, 2, 3, or 4 substituents independently selected from $R^8$;

each $R^8$ is independently selected from $C_{1-6}$ alkyl, $C_{1-6}$ haloalkyl, halo, D, CN, $OR^{a8}$, $SR^{a8}$, $C(O)R^{b8}$, $C(O)NR^{c8}R^{d8}$, $C(O)OR^{a8}$, $NR^{c8}R^{d8}$, $NR^{c8}C(O)R^{b8}$, $S(O)_2R^{b8}$ and $S(O)_2NR^{c8}R^{d8}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$ and S(O)$_2$NR$^{c1}$R$^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, OR$^{a11}$, SR$^{a11}$, C(O)R$^{b11}$, C(O)NR$^{c11}$R$^{d11}$, C(O)OR$^{a11}$, NR$^{c11}$R$^{d11}$, NR$^{11}$C(O)R$^{b11}$, NR$^{11}$C(O)OR$^{a11}$, NR$^{c11}$S(O)R$^{b11}$, NR$^{c11}$S(O)$_2$R$^{b11}$, NR$^{c11}$S(O)$_2$NR$^{c11}$R$^{d11}$, S(O)R$^{b11}$, S(O)NR$^{c11}$R$^{d11}$, S(O)$_2$R$^{b11}$ and S(O)$_2$NR$^{c11}$R$^{d11}$;

each $R^{13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, NO$_2$, OR$^{a13}$, SR$^{a13}$, C(O)R$^{b13}$, C(O)NR$^{c13}$R$^{d13}$, C(O)OR$^{a13}$, OC(O)R$^{b13}$, OC(O)NR$^{c13}$R$^{d13}$, NR$^{c13}$R$^{d13}$, NR$^{c13}$C(O)R$^{b13}$, NR$^{c13}$C(O)OR$^{a13}$, NR$^{c13}$C(O)NR$^{c13}$R$^{d13}$, NR$^{c13}$S(O)R$^{b13}$, NR$^{c13}$S(O)$_2$R$^{b13}$, NR$^{c13}$S(O)$_2$NR$^{c13}$R$^{d13}$, —S(O)R$^{b13}$, S(O)NR$^{c13}$R$^{d13}$, S(O)$_2$R$^{b13}$ and S(O)$_2$NR$^{c13}$R$^{d13}$;

each R$^{a1}$, R$^{c1}$ and R$^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

each R$^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;

each R$^{a3}$, R$^{c3}$ and R$^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each R$^{b3}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each R$^{a7}$, R$^{c7}$ and R$^{d7}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

or any R$^{c7}$ and R$^{d7}$ attached to the same N atom, together with the N atom to which they are attached, form a 4-, 5-, 6- or 7-membered heterocycloalkyl group optionally substituted with 1, 2, 3, or 4 substituents independently selected from $R^8$;

each R$^{b7}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

each R$^{a8}$, R$^{c8}$ and R$^{d8}$ is independently selected from H, $C_{1-6}$ alkyl and $C_{1-6}$ haloalkyl;

each R$^{b8}$ is independently selected from $C_{1-6}$ alkyl and $C_{1-6}$ haloalkyl;

each R$^{a11}$, R$^{c11}$ and R$^{d11}$ is independently selected from H, $C_{1-6}$ alkyl and $C_{1-6}$ haloalkyl;

each R$^{b11}$ is independently selected from $C_{1-6}$ alkyl and $C_{1-6}$ haloalkyl;

each R$^{a13}$, R$^{c13}$ and R$^{d13}$ is independently selected from H, $C_{1-6}$ alkyl and $C_{1-6}$ haloalkyl;

each R$^{b13}$ is independently selected from $C_{1-6}$ alkyl and $C_{1-6}$ haloalkyl; and each R$^{x1}$, R$^{y1}$, R$^{x2}$, and R$^{y2}$ is independently selected from H and $C_{1-6}$ alkyl.

In some embodiments, provided herein is a compound of Formula (I), or a pharmaceutically acceptable salt thereof, wherein $R^1$ is Cy$^1$;

Cy$^1$ is selected from 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl and 4-10 membered heterocycloalkyl is optionally substituted by oxo to form a carbonyl group; and wherein the 4-10 membered heterocycloalkyl, $C_{6-10}$ aryl and 5-10 membered heteroaryl are each optionally substituted with 1, 2, 3, or 4 substituents independently selected from $R^{10}$;

$R^2$ is H;

$R^3$ is selected from Cy$^3$, $C_{1-6}$ alkyl, halo, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$ and S(O)$_2$NR$^{c3}$R$^{d3}$; wherein said $C_{1-6}$ alkyl is optionally substituted with 1, 2, 3, or 4 substituents independently selected from $R^{13}$;

$R^X$ is selected from H, D, $C_{1-6}$ alkyl, CN, halo, C(O)NR$^{x1}$R$^{y1}$, and Cy$^4$; wherein said $C_{1-6}$ alkyl is optionally substituted with 1, 2, 3, or 4 substituents independently selected from $R^{13}$;

$R^Y$ is selected from H, D, $C_{1-6}$ alkyl, CN, halo, C(O)NR$^{x2}$R$^{y2}$, and Cy$^5$; wherein said $C_{1-6}$ alkyl is optionally substituted with 1, 2, 3, or 4 substituents independently selected from $R^{13}$;

wherein at least one of $R^X$ and $R^Y$ is other than H or D;

Cy$^3$, Cy$^4$, and Cy$^5$ are each independently is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

$Cy^B$ is phenyl optionally substituted with 1, 2, 3, or 4 substituents independently selected from $R^7$;

A is N;

$R^4$ is H;

$R^5$ is H;

each $R^7$ is independently selected from $C_{1-6}$ alkyl, halo, D, CN, $NO_2$, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2 R^{b7}$ and $S(O)_2NR^{c7}R^{d7}$; wherein said $C_{1-6}$ alkyl is optionally substituted with 1, 2, 3, or 4 substituents independently selected from $R^8$;

each $R^8$ is independently selected from $C_{1-6}$ alkyl, $C_{1-6}$ haloalkyl, halo, D, CN, $OR^{a8}$, $SR^{a8}$, $C(O)R^{b8}$, $C(O)NR^{c8}R^{d8}$, $C(O)OR^{a8}$, $NR^{c8}R^{d8}$, $NR^{c8}C(O)R^{b8}$, $S(O)_2R^{b8}$ and $S(O)_2NR^{c8}R^{d8}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a11}$, $SR^{a11}$, $C(O)R^{b11}$, $C(O)NR^{c11}R^{d11}$, $C(O)OR^{a11}$, $NR^{c11}R^{d11}$, $NR^{11}C(O)R^{b11}$, $NR^{11}C(O)OR^{a11}$, $NR^{c11}S(O)R^{b11}$, $NR^{c11}S(O)_2R^{b11}$, $NR^{c11}S(O)_2NR^{c11}R^{d11}$, $S(O)R^{b1}$, $S(O)NR^{c11}R^{d11}$, $S(O)_2R^{b11}$ and $S(O)_2NR^{c11}R^{d11}$;

each $R^{13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a13}$, $SR^{a13}$, $C(O)R^{b13}$, $C(O)NR^{c13}R^{d13}$, $C(O)OR^{a13}$, $OC(O)R^{b13}$, $OC(O)NR^{c13}R^{d13}$, $NR^{c13}R^{d13}$, $NR^{c13}C(O)R^{b13}$, $NR^{c13}C(O)OR^{a13}$, $NR^{c13}C(O)NR^{c13}R^{d13}$, $NR^{c13}S(O)R^{b13}$, $—NR^{c13}S(O)_2R^{b13}$, $NR^{c13}S(O)_2NR^{c13}R^{d13}$, $—S(O)R^{b13}$, $S(O)NR^{c13}R^{d13}$, $S(O)_2R^{b13}$ and $S(O)_2NR^{c13}R^{d13}$;

each $R^{a1}$, $R^{c1}$ and $R^{d1}$ is independently selected from H, and $C_{1-6}$ alkyl.

each $R^{b1}$ is independently selected from $C_{1-6}$ alkyl;

each $R^{a3}$, $R^{c3}$ and $R^{d3}$ is independently selected from H, and $C_{1-6}$ alkyl;

each $R^{b3}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^{a7}$, $R^{c7}$ and $R^{d7}$ is independently selected from H and $C_{1-6}$ alkyl;

or any $R^{c7}$ and $R^{d7}$ attached to the same N atom, together with the N atom to which they are attached, form a 4-, 5-, 6- or 7-membered heterocycloalkyl group optionally substituted with 1, 2, 3, or 4 substituents independently selected from $R^8$;

each $R^{b7}$ is independently selected from $C_{1-6}$ alkyl;

each $R^{a8}$, $R^{c8}$ and $R^{d8}$ is independently selected from H, and $C_{1-6}$ alkyl;

each $R^{b8}$ is independently selected from $C_{1-6}$ alkyl and $C_{1-6}$ haloalkyl;

each $R^{a11}$, $R^{c11}$ and $R^{d11}$ is independently selected from H, and $C_{1-6}$ alkyl;

each $R^{b11}$ is independently selected from $C_{1-6}$ alkyl;

each $R^{a13}$, $R^{c13}$ and $R^{d13}$ is independently selected from H, and $C_{1-6}$ alkyl;

each $R^{b13}$ is independently selected from $C_{1-6}$ alkyl; and each $R^{x1}$, $R^{y1}$, $R^{x2}$, and $R^{y2}$ is independently selected from H and $C_{1-6}$ alkyl.

In some embodiments, provided herein is a compound of Formula (I), or a pharmaceutically acceptable salt thereof, wherein $R^1$ is $Cy^1$;

$Cy^1$ is selected from 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl and 4-10 membered heterocycloalkyl is optionally substituted by oxo to form a carbonyl group; and wherein the 4-10 membered heterocycloalkyl, $C_{6-10}$ aryl and 5-10 membered heteroaryl are each optionally substituted with 1, 2, 3, or 4 substituents independently selected from $R^{10}$;

$R^2$ is H;

$R^3$ is selected from $Cy^3$, $C_{1-6}$ alkyl, halo, CN, and $C(O)NR^{c3}R^{d3}$; wherein said $C_{1-6}$ alkyl is optionally substituted with 1, 2, 3, or 4 substituents independently selected from $R^{13}$;

$R^X$ is selected from H, D, $C_{1-6}$ alkyl, CN, halo, $C(O)NR^{x1}R^{y1}$, and $Cy^4$; wherein said $C_{1-6}$ alkyl is optionally substituted with 1, 2, 3, or 4 substituents independently selected from $R^{13}$;

$R^Y$ is selected from H, D, $C_{1-6}$ alkyl, CN, halo, $C(O)NR^{x2}R^{y2}$, and $Cy^5$; wherein said $C_{1-6}$ alkyl is optionally substituted with 1, 2, 3, or 4 substituents independently selected from $R^{13}$;

wherein at least one of $R^X$ and $R^Y$ is other than H or D;

$Cy^3$, $Cy^4$, and $Cy^5$ are each independently is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

$Cy^B$ is phenyl optionally substituted with 1, 2, 3, or 4 substituents independently selected from $R^7$;

A is N;

$R^4$ is H;

$R^5$ is H;

each $R^7$ is independently selected from halo and $OR^{a7}$;

each $R^8$ is independently selected from $C_{1-6}$ alkyl, $C_{1-6}$ haloalkyl, halo, D, CN, $OR^{a8}$, $SR^{a8}$, $C(O)R^{b8}$, $C(O)NR^{c8}R^{d8}$, $C(O)OR^{a8}$, $NR^{c8}R^{d8}$, $NR^{c8}C(O)R^{b8}$, $S(O)_2R^{b8}$ and $S(O)_2NR^{c8}R^{d8}$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a11}$, $SR^{a11}$, $C(O)R^{b11}$, $C(O)NR^{c11}R^{d11}$, $C(O)OR^{a11}$, $NR^{c11}R^{d11}$, $NR^{c11}C(O)R^{b11}$, $NR^{11}C(O)OR^{a11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$ and $S(O)_2NR^{c11}R^{d11}$;

each $R^{13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a13}$, $SR^{a13}$, $C(O)R^{b13}$, $C(O)NR^{c13}R^{d13}$, $C(O)OR^{a13}$, $OC(O)R^{b13}$, $OC(O)NR^{c13}R^{d13}$, $NR^{c13}R^{d13}$, $NR^{c13}C(O)R^{b13}$, $NR^{c13}C(O)OR^{a13}$, $NR^{c13}C(O)NR^{c13}R^{d13}$, $NR^{c13}S(O)R^{b13}$, $NR^{c13}S(O)_2R^{b13}$, $NR^{c13}S(O)_2NR^{c13}R^{d13}$, $S(O)R^{b13}$, $S(O)NR^{c13}R^{d13}$, $S(O)_2R^{b13}$ and $S(O)_2 NR^{c13}R^{d13}$;

each $R^{a1}$, $R^{c1}$ and $R^{d1}$ is independently selected from H, and $C_{1-6}$ alkyl.

each $R^{b1}$ is independently selected from $C_{1-6}$ alkyl;

each $R^{a3}$, $R^{c3}$ and $R^{d3}$ is independently selected from H, and $C_{1-6}$ alkyl;

each $R^{b3}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^{a7}$, $R^{c7}$ and $R^{d7}$ is independently selected from H and $C_{1-6}$ alkyl;

or any $R^{c7}$ and $R^{d7}$ attached to the same N atom, together with the N atom to which they are attached, form a 4-, 5-, 6- or 7-membered heterocycloalkyl group optionally substituted with 1, 2, 3, or 4 substituents independently selected from $R^8$;

each $R^{b7}$ is independently selected from $C_{1-6}$ alkyl;

each $R^{a8}$, $R^{c8}$ and $R^{d8}$ is independently selected from H, and $C_{1-6}$ alkyl;

each $R^{b8}$ is independently selected from $C_{1-6}$ alkyl and $C_{1-6}$ haloalkyl;

each $R^{a11}$, $R^{c11}$ and $R^{d11}$ is independently selected from H, and $C_{1-6}$ alkyl;

each $R^{b11}$ is independently selected from $C_{1-6}$ alkyl;

each $R^{a13}$, $R^{c13}$ and $R^{d13}$ is independently selected from H, and $C_{1-6}$ alkyl;

each $R^{b13}$ is independently selected from $C_{1-6}$ alkyl; and each $R^{x1}$, $R^{y1}$, $R^{x2}$, and $R^{y2}$ is independently selected from H and $C_{1-6}$ alkyl.

In some embodiments, provided herein is a compound of Formula (I), or a pharmaceutically acceptable salt thereof, wherein $R^1$ is $Cy^1$;

$Cy^1$ is selected from 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl and 4-10 membered heterocycloalkyl is optionally substituted by oxo to form a carbonyl group; and wherein the 4-10 membered heterocycloalkyl, $C_{6-10}$ aryl and 5-10 membered heteroaryl are each optionally substituted with 1, 2, 3, or 4 substituents independently selected from $R^{10}$;

$R^2$ is H;

$R^3$ is selected from $Cy^3$, $C_{1-6}$ alkyl, $C_{1-6}$ haloalkyl, halo, CN, and $C(O)NR^{c3}R^{d3}$; wherein said $C_{1-6}$ alkyl is optionally substituted with 1, 2, 3, or 4 substituents independently selected from $R^{13}$;

$R^X$ is selected from H, D, $C_{1-6}$ alkyl, CN, halo, and $C(O)NR^{x1}R^{y1}$;

$R^Y$ is selected from H, D, $C_{1-6}$ alkyl, CN, halo, and $Cy^5$; wherein at least one of $R^X$ and $R^Y$ is other than H or D;

$Cy^3$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

$Cy^5$ is selected from $C_{6-10}$ aryl and 5-10 membered heteroaryl; wherein 5-10 membered heteroaryl each has at least one ring-forming carbon atom and 1, 2, 3, or 4 ring-forming heteroatoms independently selected from N, O, and S;

$Cy^B$ is phenyl optionally substituted with 1, 2, 3, or 4 substituents independently selected from $R^7$;

A is N;

$R^4$ is H;

$R^5$ is H;

each $R^7$ is independently selected from halo and $OR^{a7}$;

each $R^{10}$ is independently selected from $C_{1-6}$ alkyl, $OR^{a1}$, $C(O)NR^{c1}R^{d1}$, $NR^{c1}R^{d1}$, and $NR^{c1}C(O)OR^{a1}$; wherein said $C_{1-6}$ alkyl is optionally substituted with 1, 2, 3, or 4 substituents independently selected from $R^{11}$;

each $R^{11}$ is independently selected from $OR^{a11}$ and $NR^{c11}R^{d11}$;

each $R^{13}$ is independently selected from $C_{1-6}$ alkyl, halo, D, CN, and $OR^{a13}$;

each $R^{a1}$, $R^{c1}$ and $R^{d1}$ is independently selected from H and $C_{1-6}$ alkyl.

each $R^{a7}$ is independently selected from H and $C_{1-6}$ alkyl;

each $R^{a11}$, $R^{c11}$ and $R^{d11}$ is independently selected from H, and $C_{1-6}$ alkyl;

each $R^{a13}$ is independently selected from H, and $C_{1-6}$ alkyl; and each $R^{x1}$ and $R^{y1}$ is independently selected from H and $C_{1-6}$ alkyl.

In some embodiments, $R^1$ is $Cy^1$.

In some embodiments, $Cy^1$ is selected from 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of the 5-10 membered heteroaryl and 4-10 membered heterocycloalkyl is optionally substituted by oxo; and wherein the 4-10 membered heterocycloalkyl, $C_{6-10}$ aryl and 5-10 membered heteroaryl are each optionally substituted with 1, 2, 3, or 4 substituents independently selected from $R^{10}$.

In some embodiments, $Cy^1$ is selected from 4-10 membered heterocycloalkyl and 5-10 membered heteroaryl; wherein the 5-10 membered heteroaryl and 4-10 membered heterocycloalkyl is optionally substituted by oxo; and wherein the 4-10 membered heterocycloalkyl and 5-10 membered heteroaryl are each optionally substituted with 1, 2, 3, or 4 substituents independently selected from $R^{10}$.

In some embodiments, $Cy^1$ is selected from (1S,4S)-2,5-diazabicyclo[2.2.1]heptan-2-yl; 2,5-diazabicyclo[2.2.1]heptan-2yl; diazabicycloheptanyl; (1S,4S)-2,5-diazabicyclo[2.2.2]octan-2-yl; 2,5-diazabicyclo[2.2.1]octan-2-yl; diazabicyclooctanyl; pyrrolidinyl; morpholinyl; 2,7-diazaspiro[4.4]nonan-2-yl; diazaspirononanyl; azetidinyl; pyrazolyl; piperidinyl; piperazinyl; and pyridinyl; wherein each $Cy^1$ is optionally substituted by oxo; and wherein each $Cy^1$ is optionally substituted with 1, 2, 3, or 4 substituents independently selected from $R^{10}$.

In some embodiments, $Cy^1$ is selected from 2,5-diazabicyclo[2.2.1]heptan-2-yl; 5-(ethylcarbamoyl)-2,5-diazabicyclo[2.2.1]heptan-2-yl; 4-amino-2-(hydroxymethyl)pyrrolidin-1-yl; 3-aminopyrrolidin-1-yl; 2,5-diazabicyclo[2.2.1]octan-2-yl; 2-(hydroxymethyl)pyrrolidin-1-yl; morpholino; 6-oxo-2,7-diazaspiro[4.4]nonan-2-yl; 3-aminoazetidin-1-yl; 2-(aminomethyl)pyrrolidin-1-yl; pyrrolidin-3-yl; 2-oxopyrrolidin-1-yl; 1H-pyrazol-1-yl; o-tolyl; 3-aminopiperidin-1-yl; piperazin-1-yl; pyridin-3-yl; 1-methyl-1H-pyrazol-4-yl; 3-(hydroxymethyl)phenyl; 2-(hydroxymethyl)phenyl; 3-((dimethylamino)methyl)phenyl; and 4-(dimethylamino)piperidin-1-yl.

In some embodiments, $Cy^1$ is $C_{6-10}$ aryl optionally substituted with 1, 2, 3, or 4 substituents independently selected from $R^{10}$.

In some embodiments, $Cy^1$ is phenyl optionally substituted with 1, 2, 3, or 4 substituents independently selected from $R^{10}$.

In some embodiments, $Cy^1$ is selected from 4-hydroxy-2-(aminomethyl)pyrrolidin-1-yl and 3-(hydroxymethyl)piperazin-1-yl.

In some embodiments, $Cy^1$ is selected from 2,5-diazabicyclo[2.2.1]heptan-2-yl; 5-(ethylcarbamoyl)-2,5-diazabicyclo[2.2.1]heptan-2-yl; 4-amino-2-(hydroxymethyl)pyrrolidin-1-yl; 3-aminopyrrolidin-1-yl; 2,5-diazabicyclo[2.2.1]octan-2-yl; 2-(hydroxymethyl)pyrrolidin-1-yl; morpholino; 6-oxo-2,7-diazaspiro[4.4]nonan-2-yl; 3-aminoazetidin-1-yl; 2-(aminomethyl)pyrrolidin-1-yl; pyrrolidin-3-yl; 2-oxopyrrolidin-1-yl; 1H-pyrazol-1-yl; o-tolyl; 3-aminopiperidin-1-yl; piperazin-1-yl; pyridin-3-yl; 1-methyl-1H-pyrazol-4-yl; 3-(hydroxymethyl)phenyl; 2-(hydroxymethyl)phenyl; 3-((dimethylamino)methyl)phenyl; 4-(dimethylamino)piperidin-1-yl; 4-hydroxy-2-(aminomethyl)pyrrolidin-1-yl and 3-(hydroxymethyl)piperazin-1-yl.

In some embodiments, $R^1$ is $NR^cR^d$.

In some embodiments, each $R^c$ and $R^d$ is independently selected from H, $C_{1-6}$ alkyl, and 4-7 membered heterocycloalkyl, wherein said $C_{1-6}$ alkyl and 4-7 membered heterocycloalkyl are each optionally substituted with 1, 2, or 3 substituents independently selected from $R^{10}$.

In some embodiments, $R^2$ is H.

In some embodiments, $R^3$ is selected from $Cy^3$, $C_{1-6}$ alkyl, $C_{2-6}$ alkenyl, $C_{2-6}$ alkynyl, $C_{1-6}$ haloalkyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$.

In some embodiments, $R^3$ is selected from $Cy^3$, $C_{1-6}$ alkyl, $C_{2-6}$ alkenyl, $C_{2-6}$ alkynyl, $C_{1-6}$ haloalkyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$.

In some embodiments, $R^3$ is selected from $Cy^3$, $C_{1-6}$ alkyl, $C_{2-6}$ alkenyl, $C_{2-6}$ alkynyl, $C_{1-6}$ haloalkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, and $NR^{c3}C(O)NR^{c3}R^{d3}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$.

In some embodiments, $R^3$ is selected from $Cy^3$, $C_{1-6}$ alkyl, and $C_{1-6}$ haloalkyl; wherein said $C_{1-6}$ alkyl is optionally substituted with 1, 2, 3, or 4 substituents independently selected from $R^{13}$.

In some embodiments, $R^3$ is selected from $C_{1-6}$ alkyl, CN, halo, $C(O)NR^{c3}R^{d3}$, and $Cy^3$, wherein said $C_{1-6}$ alkyl is optionally substituted with 1, 2, 3, or 4 substituents independently selected from $R^{13}$.

In some embodiments, $R^3$ is halo. In some embodiments, $R^3$ is F.

In some embodiments, $R^3$ is $C_{1-6}$ alkyl, wherein said $C_{1-6}$ alkyl is optionally substituted with 1, 2, 3, or 4 substituents independently selected from $R^{13}$.

In some embodiments, $R^3$ is methyl.

In some embodiments, $R^3$ is 2-hydroxyethyl

In some embodiments, $R^3$ is CN.

In some embodiments, $R^3$ is $C(O)NR^{c3}R^{d3}$.

In some embodiments, $R^3$ is 2-methoxyethyl. In some embodiments, $R^3$ is 2-fluoroethyl.

In some embodiments, $R^3$ is $Cy^3$.

In some embodiments, $Cy^3$ is 4-10 membered heterocycloalkyl or 5-10 membered heteroaryl, each of which is optionally substituted with 1, 2, 3, or 4 substituents independently selected from $R^{13}$.

In some embodiments, $Cy^3$ is 4-10 membered heterocycloalkyl, which is optionally substituted with 1, 2, 3, or 4 substituents independently selected from $R^{13}$. In some embodiments, $Cy^3$ is 4-10 membered heterocycloalkyl. In some embodiments, $Cy^3$ is tetrahydrofuranyl.

In some embodiments, $Cy^3$ is 5-10 membered heteroaryl, which is optionally substituted with 1, 2, 3, or 4 substituents independently selected from $R^{13}$. In some embodiments, $Cy^3$ is 3-cyanopyridinyl.

In some embodiments, $R^X$ is selected from H, D, $Cy^4$, $C_{1-6}$ alkyl, $C_{2-6}$ alkenyl, $C_{2-6}$ alkynyl, $C_{1-6}$ haloalkyl, halo, CN, $OR^{v1}$, $SR^{v1}$, $C(O)R^{w1}$, $C(O)NR^{x1}R^{y1}$, $C(O)OR^{v1}$, $OC(O)R^{w1}$, $OC(O)NR^{x1}R^{y1}$, $NR^{x1}R^{y1}$, $NR^{x1}C(O)R^{w1}$, $NR^{x1}C(O)OR^{v1}$, and $NR^{x1}C(O)NR^{x1}R^{y1}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$.

In some embodiments, $R^X$ is selected from H, D, $C_{1-6}$ alkyl, CN, halo, and $C(O)NR^{x1}R^{y1}$; wherein said $C_{1-6}$ alkyl is optionally substituted with 1, 2, 3, or 4 substituents independently selected from $R^{13}$. In some embodiments, $R^X$ is halo. In some embodiments, $R^X$ is F. In some embodiments, $R^X$ is CN. In some embodiments, $R^X$ is $C_{1-6}$ alkyl, wherein said $C_{1-6}$ alkyl is optionally substituted with 1, 2, 3, or 4 substituents independently selected from $R^{13}$. In some embodiments, $R^X$ is methyl. In some embodiments, $R^X$ is $C(O)NR^{x1}R^{y1}$.

In some embodiments, $R^Y$ is selected from H, D, $Cy^5$, $C_{1-6}$ alkyl, $C_{2-6}$ alkenyl, $C_{2-6}$ alkynyl, $C_{1-6}$ haloalkyl, halo, CN, $OR^{v2}$, $SR^{v2}$, $C(O)R^{w2}$, $C(O)NR^{x2}R^{y2}$, $C(O)OR^X$, $OC(O)R^{w2}$, $OC(O)NR^{x2}R^{y2}$, $NR^{x2}R^{y2}$, $NR^{x2}C(O)R^{w2}$, $NR^{x2}C(O)OR^{v2}$, and $NR^{x2}C(O)NR^{x2}R^{y2}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$.

In some embodiments, $R^Y$ is selected from H, D, $C_{1-6}$ alkyl, halo, and $Cy^5$; wherein said $C_{1-6}$ alkyl is optionally substituted with 1, 2, 3, or 4 substituents independently selected from $R^{13}$. In some embodiments, $R^Y$ is halo. In some embodiments, $R^Y$ is I. In some embodiments, $R^Y$ is $C_{1-6}$ alkyl. In some embodiments, $R^Y$ is methyl. In some embodiments, $R^Y$ is $Cy^5$.

In some embodiments, $Cy^5$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of the 5-10 membered heteroaryl and 4-10 membered heterocycloalkyl is optionally substituted by oxo; and wherein the $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$.

In some embodiments, $Cy^5$ is $C_{6-10}$ aryl or 5-10 membered heteroaryl, each optionally substituted with 1, 2, 3, or 4 substituents independently selected from $R^{13}$.

In some embodiments, $Cy^5$ is $C_{6-10}$ aryl, wherein said $C_{6-10}$ aryl is optionally substituted with 1, 2, 3, or 4 substituents independently selected from $R^{13}$.

In some embodiments, $Cy^5$ is phenyl, wherein said phenyl is optionally substituted with 1, 2, 3, or 4 substituents independently selected from $R^{13}$. In some embodiments, $Cy^5$ is phenyl.

In some embodiments, $Cy^5$ is 5-10 membered heteroaryl, wherein said heteroaryl is optionally substituted with 1, 2, 3, or 4 substituents independently selected from $R^{13}$.

In some embodiments, $Cy^5$ is pyrazolyl, wherein pyrazolyl is optionally substituted with 1, 2, 3, or 4 substituents independently selected from $R^{13}$. In some embodiments, $Cy^5$ is 1-methyl-1H-pyrazol-4-yl.

In some embodiments, $R^{x1}$ is selected from $C_{1-6}$ alkyl and H.

In some embodiments, $R^{y1}$ is selected from $C_{1-6}$ alkyl and H.

In some embodiments, A is N.

In some embodiments, A is $CR^A$.

In some embodiments, $R^A$ is $C_{1-3}$ alkyl or H. In some embodiments, $R^A$ is H.

In some embodiments, $R^4$ is selected from H, D, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^{g4}$.

In some embodiments, $R^4$ is selected from H, D, and $C_{1-6}$ alkyl.

In some embodiments, $R^4$ is H.

In some embodiments, $R^5$ is selected from H, D, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$.

In some embodiments, $R^5$ is H.

In some embodiments, $Cy^B$ is $C_{6-10}$ aryl optionally substituted with 1, 2, 3, or 4 substituents independently selected from $R^7$.

In some embodiments, $Cy^B$ is phenyl optionally substituted with 1, 2, 3, or 4 substituents independently selected from $R^7$.

In some embodiments, each $R^7$ is independently selected from $C_{1-6}$ alkyl, $C_{2-6}$ alkenyl, $C_{2-6}$ alkynyl, $C_{1-6}$ haloalkyl, halo, D, CN, $NO_2$, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$ and $S(O)_2NR^{c7}R^{d7}$; wherein said $C_{1-6}$ alkyl, $C_{2-6}$ alkenyl, $C_{2-6}$ alkynyl, are each optionally substituted with 1, 2, 3, or 4 substituents independently selected from $R^8$.

In some embodiments, each $R^7$ is independently selected from $C_{1-6}$ alkyl, $C_{2-6}$ alkenyl, $C_{2-6}$ alkynyl, $C_{1-6}$ haloalkyl, halo, D, CN, $OR^{a7}$, $SR^{a7}$, $C(O)R^{b7}$, $C(O)NR^{c7}R^{d7}$, $C(O)OR^{a7}$, $NR^{c7}R^{d7}$, $NR^{c7}C(O)R^{b7}$, $NR^{c7}C(O)OR^{a7}$, and $NR^{c7}C(O)NR^{c7}R^{d7}$; wherein said $C_{1-6}$ alkyl, $C_{2-6}$ alkenyl, $C_{2-6}$ alkynyl, are each optionally substituted with 1, 2, 3, or 4 substituents independently selected from $R^8$.

In some embodiments, each $R^7$ is independently selected from $C_{1-6}$ alkyl, 5-10 membered heteroaryl, halo, $OR^{a7}$, $C(O)NR^{c7}R^{d7}$, $NR^{c7}R^{d7}$, wherein said $C_{1-6}$ alkyl and 5-10 membered heteroaryl are each optionally substituted with 1, 2, or 3 substituents independently selected from $R^8$.

In some embodiments, each $R^7$ is independently selected from halo and $OR^{a7}$.

In some embodiments, each $R^8$ is independently selected from $C_{1-6}$ alkyl, $C_{1-6}$ haloalkyl, halo, D, CN, $OR^{a8}$, $SR^{a8}$, $C(O)R^{b8}$, $C(O)NR^{c8}R^{d8}$, $C(O)OR^{a8}$, $NR^{c8}R^{d8}$, $NR^{c8}C(O)R^{b8}$, $S(O)_2R^{b8}$ and $S(O)_2NR^{c8}R^{d8}$.

In some embodiments, each $R^8$ is independently selected from $C_{1-6}$ alkyl and D.

In some embodiments, each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, are each optionally substituted with 1, 2, 3, or 4 substituents independently selected from $R^{11}$.

In some embodiments, each $R^{10}$ is independently selected from $C_{1-6}$ alkyl, $C_{2-6}$ alkenyl, $C_{2-6}$ alkynyl, $C_{1-6}$ haloalkyl, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, and $NR^{c1}C(O)OR^{a1}$; wherein said $C_{1-6}$ alkyl, $C_{2-6}$ alkenyl, and $C_{2-6}$ alkynyl are each optionally substituted with 1, 2, 3, or 4 substituents independently selected from $R^{11}$.

In some embodiments, each $R^{10}$ is independently selected from $C(O)NR^{c1}R^{d1}$, $NR^{c1}R^{d1}$, and $C_{1-6}$ alkyl; wherein said $C(O)NR^{c1}R^{d1}$, $NR^{c1}R^{d1}$, and $C_{1-6}$ alkyl are each optionally substituted with 1, 2, 3, or 4 substituents independently selected from $R^{11}$.

In some embodiments, each $R^{10}$ is independently selected from $C_{1-6}$ alkyl, $OR^{a1}$, $C(O)NR^{c1}R^{d1}$ and $NR^{c1}R^{d1}$.

In some embodiments, each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a11}$, $SR^{a11}$, $C(O)R^{b11}$, $C(O)NR^{c11}R^{d11}$, $C(O)OR^{a11}$, $NR^{c11}R^{d11}$, $NR^{11}C(O)R^{b11}$, $NR^{c11}C(O)OR^{a11}$, $NR^{c11}S(O)R^{b11}$, $NR^{c1}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$ and $S(O)_2NR^{c11}R^{d11}$.

In some embodiments, each $R^{11}$ is independently selected from $OR^{a11}$ and $NR^{c11}R^{d11}$.

In some embodiments, each $R^{13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a13}$, $SR^{a13}$, $C(O)R^{b13}$, $C(O)NR^{c13}R^{d13}$, $C(O)OR^{a13}$, $OC(O)R^{b13}$, $OC(O)NR^{c13}R^{d13}$, $NR^{c13}R^{d13}$, $NR^{c13}C(O)R^{b13}$, $NR^{c13}C(O)OR^{a13}$, $NR^{c13}C(O)NR^{c13}R^{d13}$, $—NR^{c13}S(O)R^{b13}$, $NR^{c13}S(O)_2R^{b13}$, $NR^{c13}S(O)_2NR^{c13}R^{d13}$, $S(O)R^{b13}$, $S(O)NR^{c13}R^{d13}$, $S(O)_2R^{b13}$ and $S(O)_2NR^{c3}R^{d13}$.

In some embodiments, each $R^{13}$ is independently selected from $C_{1-6}$ alkyl, $C_{2-6}$ alkenyl, $C_{2-6}$ alkynyl, $C_{1-6}$ haloalkyl, halo, D, CN, $OR^{a13}$, $SR^{a13}$, $C(O)R^{b13}$, $C(O)NR^{c13}R^{d13}$, $C(O)OR^{a13}$, $NR^{c13}R^{d13}$, $NR^{c13}C(O)R^{b13}$, $NR^{c13}C(O)OR^{a13}$, and $NR^{c13}C(O)NR^{c13}R^{d13}$.

In some embodiments, each $R^{13}$ is independently selected from $C_{1-6}$ alkyl, CN, and $OR^{a13}$.

In some embodiments, $R^{13}$ is $OR^{a13}$.

In some embodiments, each $R^{13}$ is independently selected from $C_{1-6}$ alkyl, halo, CN and $OR^{a13}$. In some embodiments, $R^{13}$ is CN.

In some embodiments, each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl.

In some embodiments, $R^{c1}$ is selected from H and $C_{1-6}$ alkyl.

In some embodiments, $R^{d1}$ is selected from H and $C_{1-6}$ alkyl.

In some embodiments, each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl.

In some embodiments, each $R^{a3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$.

In some embodiments, $R^{c3}$ is selected from $C_{1-6}$ alkyl and H.

In some embodiments, $R^{d3}$ is selected from $C_{1-6}$ alkyl and H.

In some embodiments, each $R^{b3}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$.

In some embodiments, each $R^{a7}$, $R^{c7}$ and $R^{d7}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$.

In some embodiments, each $R^{a7}$, $R^{c7}$ and $R^{d7}$ are each independently selected from H and $C_{1-6}$ alkyl, In some embodiments, $R^{a7}$ is $C_{1-6}$ alkyl. In some embodiments, $R^{a7}$ is methyl.

In some embodiments, or any $R^{c7}$ and $R^{d7}$ attached to the same N atom, together with the N atom to which they are attached, form a 4-, 5-, 6- or 7-membered heterocycloalkyl group optionally substituted with 1, 2, 3, or 4 substituents independently selected from $R^8$.

In some embodiments, each $R^{b7}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$.

In some embodiments, each $R^{a8}$, $R^{c8}$ and $R^{d8}$ is independently selected from H, $C_{1-6}$ alkyl and $C_{1-6}$ haloalkyl.

In some embodiments, each $R^{b8}$ is independently selected from $C_{1-6}$ alkyl and $C_{1-6}$ haloalkyl.

In some embodiments, each $R^{a11}$, $R^{c11}$ and $R^{d11}$ is independently selected from H, $C_{1-6}$ alkyl and $C_{1-6}$ haloalkyl.

In some embodiments, each $R^{a11}$, $R^{c11}$ and $R^{d11}$ is independently selected from H and $C_{1-6}$ alkyl.

In some embodiments, $R^{a11}$ is H.

In some embodiments, $R^{c11}$ is selected from H and $C_{1-6}$ alkyl.

In some embodiments, $R^{d11}$ is H.

In some embodiments, each $R^{b11}$ is independently selected from $C_{1-6}$ alkyl and $C_{1-6}$ haloalkyl.

In some embodiments, each $R^{a13}$, $R^{c13}$ and $R^{d13}$ is independently selected from H, $C_{1-6}$ alkyl and $C_{1-6}$ haloalkyl.

In some embodiments, $R^{a13}$ is selected from H and $C_{1-6}$ alkyl.

In some embodiments, each $R^{b13}$ is independently selected from $C_{1-6}$ alkyl and $C_{1-6}$ haloalkyl.

In some embodiments, provided herein is a compound having Formula IA:

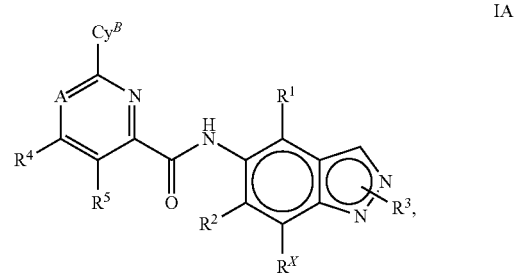

IA or a pharmaceutically acceptable salt thereof, wherein $R^1$, $R^2$, $R^3$, $R^4$, $R^5$, $R^X$, $Cy^B$, and A are as defined herein.

In some embodiments, provided herein is a compound having Formula IB:

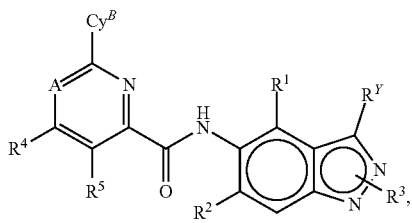

IB or a pharmaceutically acceptable salt thereof, wherein $R^1$, $R^2$, $R^3$, $R^4$, $R^5$, $R^Y$, $Cy^B$, and A are as defined herein.

In some embodiments, provided herein is a compound having Formula II:

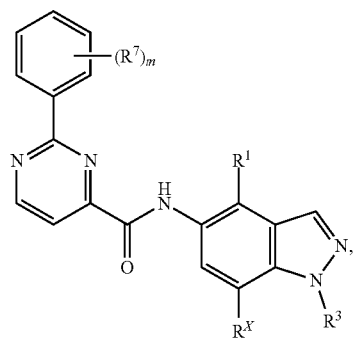

II or a pharmaceutically acceptable salt thereof, wherein m is 1, 2, 3, or 4, and wherein $R^1$, $R^3$, $R^7$, and $R^X$ are as defined herein.

In some embodiments, provided herein is a compound having Formula III:

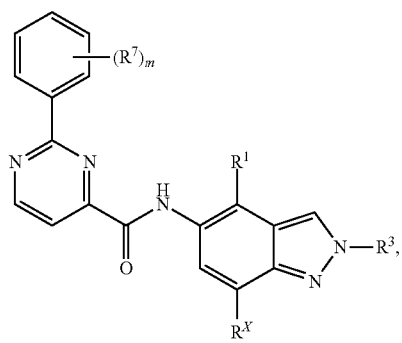

III or a pharmaceutically acceptable salt thereof, wherein m is 1, 2, 3, or 4, and wherein $R^1$, $R^3$, $R^7$, and $R^X$ are as defined herein.

In some embodiments, provided herein is a compound having Formula IV:

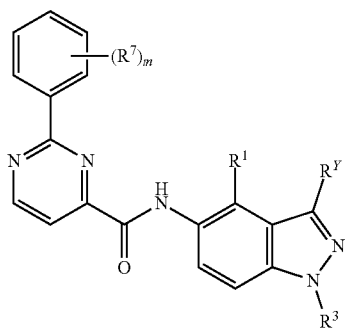

IV or a pharmaceutically acceptable salt thereof, wherein m is 1, 2, 3, or 4, and wherein $R^1$, $R^3$, $R^7$, and $R^Y$ are as defined herein.

In some embodiments, provided herein is a compound having Formula V:

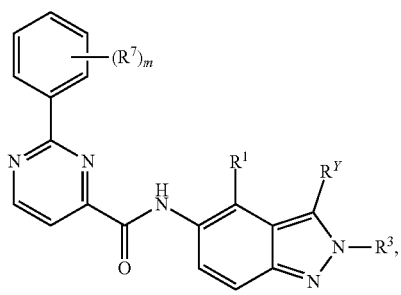

V or a pharmaceutically acceptable salt thereof, wherein m is 1, 2, 3, or 4, and wherein $R^1$, $R^3$, $R^7$, and $R^Y$ are as defined herein.

In some embodiments, provided herein is a compound having Formula VI:

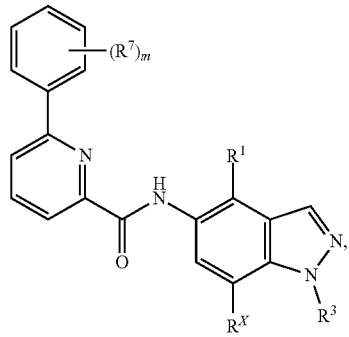

VI or a pharmaceutically acceptable salt thereof, wherein m is 1, 2, 3, or 4, and wherein $R^1$, $R^3$, $R^7$, and $R^X$ are as defined herein.

In some embodiments, provided herein is a compound selected from:

N-(4-((1S,4S)-2,5-Diazabicyclo[2.2.1]heptan-2-yl)-7-fluoro-1-methyl-1H-indazol-5-yl)-2-(2-fluoro-6-methoxyphenyl)pyrimidine-4-carboxamide;

N-(4-((1S,4S)-2,5-diazabicyclo[2.2.1]heptan-2-yl)-7-fluoro-2-methyl-2H-indazol-5-yl)-2-(2-fluoro-6-methoxyphenyl)pyrimidine-4-carboxamide;

(1S,4S)—N-Ethyl-5-(7-fluoro-5-(2-(2-fluoro-6-methoxyphenyl)pyrimidine-4-carboxamido)-1-methyl-1H-indazol-4-yl)-2,5-diazabicyclo[2.2.1]heptane-2-carboxamide;

N-(4-((2S,4S)-4-Amino-2-(hydroxymethyl)pyrrolidin-1-yl)-7-fluoro-1-methyl-1H-indazol-5-yl)-2-(2-fluoro-6-methoxyphenyl)pyrimidine-4-carboxamide;

N-(4-((2S,4S)-4-amino-2-(hydroxymethyl)pyrrolidin-1-yl)-7-fluoro-2-methyl-2H-indazol-5-yl)-2-(2-fluoro-6-methoxyphenyl)pyrimidine-4-carboxamide;

(R)—N-(4-(3-Aminopyrrolidin-1-yl)-7-fluoro-1-methyl-1H-indazol-5-yl)-2-(2-fluoro-6-methoxyphenyl)pyrimidine-4-carboxamide;

(R)—N-(4-(3-aminopyrrolidin-1-yl)-7-fluoro-2-methyl-2H-indazol-5-yl)-2-(2-fluoro-6-methoxyphenyl)pyrimidine-4-carboxamide;

N-(4-((1S,4S)-2,5-Diazabicyclo[2.2.2]octan-2-yl)-7-fluoro-1-methyl-1H-indazol-5-yl)-2-(2-fluoro-6-methoxyphenyl)pyrimidine-4-carboxamide;

N-(4-((1S,4S)-2,5-diazabicyclo[2.2.2]octan-2-yl)-7-fluoro-2-methyl-2H-indazol-5-yl)-2-(2-fluoro-6-methoxyphenyl)pyrimidine-4-carboxamide;

(R)—N-(7-Fluoro-4-(2-(hydroxymethyl)pyrrolidin-1-yl)-1-methyl-1H-indazol-5-yl)-2-(2-fluoro-6-methoxyphenyl)pyrimidine-4-carboxamide;

(R)—N-(7-fluoro-4-(2-(hydroxymethyl)pyrrolidin-1-yl)-2-methyl-2H-indazol-5-yl)-2-(2-fluoro-6-methoxyphenyl)pyrimidine-4-carboxamide;

N-(7-Fluoro-1-methyl-4-morpholino-1H-indazol-5-yl)-2-(2-fluoro-6-methoxyphenyl)pyrimidine-4-carboxamide;

N-(7-fluoro-2-methyl-4-morpholino-2H-indazol-5-yl)-2-(2-fluoro-6-methoxyphenyl)pyrimidine-4-carboxamide;

N-(7-Fluoro-1-methyl-4-(6-oxo-2,7-diazaspiro[4.4]nonan-2-yl)-1H-indazol-5-yl)-2-(2-fluoro-6-methoxyphenyl)pyrimidine-4-carboxamide;

N-(7-fluoro-2-methyl-4-(6-oxo-2,7-diazaspiro[4.4]nonan-2-yl)-2H-indazol-5-yl)-2-(2-fluoro-6-methoxyphenyl)pyrimidine-4-carboxamide;

N-(4-(3-Aminoazetidin-1-yl)-7-fluoro-1-methyl-1H-indazol-5-yl)-2-(2-fluoro-6-methoxyphenyl)pyrimidine-4-carboxamide;

(R)—N-(4-(2-(Aminomethyl)pyrrolidin-1-yl)-7-fluoro-1-methyl-1H-indazol-5-yl)-2-(2-fluoro-6-methoxyphenyl)pyrimidine-4-carboxamide;

(R)—N-(4-(2-(Aminomethyl)pyrrolidin-1-yl)-7-fluoro-2-methyl-2H-indazol-5-yl)-2-(2-fluoro-6-methoxyphenyl)pyrimidine-4-carboxamide;

N-(7-Fluoro-1-methyl-4-(pyrrolidin-3-yl)-1H-indazol-5-yl)-2-(2-fluoro-6-methoxyphenyl)pyrimidine-4-carboxamide;

N-(7-Fluoro-1-methyl-4-(2-oxopyrrolidin-1-yl)-1H-indazol-5-yl)-2-(2-fluoro-6-methoxyphenyl)pyrimidine-4-carboxamide;

N-(7-Fluoro-1-methyl-4-(1H-pyrazol-1-yl)-1H-indazol-5-yl)-2-(2-fluoro-6-methoxyphenyl)pyrimidine-4-carboxamide;

N-(7-Fluoro-1-methyl-4-o-tolyl-1H-indazol-5-yl)-2-(2-fluoro-6-methoxyphenyl)pyrimidine-4-carboxamide;

N-(7-Fluoro-2-methyl-4-o-tolyl-2H-indazol-5-yl)-2-(2-fluoro-6-methoxyphenyl)pyrimidine-4-carboxamide;

(R)—N-(4-(3-aminopiperidin-1-yl)-7-cyano-1-methyl-1H-indazol-5-yl)-2-(2-fluoro-6-methoxyphenyl)pyrimidine-4-carboxamide;

(R)—N-(4-(3-aminopiperidin-1-yl)-7-cyano-2-methyl-2H-indazol-5-yl)-2-(2-fluoro-6-methoxyphenyl)pyrimidine-4-carboxamide;

(R)-4-(3-aminopiperidin-1-yl)-5-(2-(2-fluoro-6-methoxyphenyl)pyrimidine-4-carboxamido)-N,1-dimethyl-1H-indazole-7-carboxamide;

(R)-4-(3-aminopiperidin-1-yl)-5-(2-(2-fluoro-6-methoxyphenyl)pyrimidine-4-carboxamido)-N,2-dimethyl-2H-indazole-7-carboxamide;

(R)—N-(4-(3-Aminopyrrolidin-1-yl)-7-fluoro-1-(2-hydroxyethyl)-1H-indazol-5-yl)-2-(2-fluoro-6-methoxyphenyl)pyrimidine-4-carboxamide;

N-(1,7-Dimethyl-4-(piperazin-1-yl)-1H-indazol-5-yl)-2-(2-fluoro-6-methoxyphenyl)pyrimidine-4-carboxamide;

N-(2,7-dimethyl-4-(piperazin-1-yl)-2H-indazol-5-yl)-2-(2-fluoro-6-methoxyphenyl)pyrimidine-4-carboxamide;

(R)—N-(4-(3-aminopyrrolidin-1-yl)-1,7-dimethyl-1H-indazol-5-yl)-2-(2-fluoro-6-methoxyphenyl)pyrimidine-4-carboxamide;

N-(7-Fluoro-1-methyl-4-(pyridin-3-yl)-1H-indazol-5-yl)-2-(2-fluoro-6-methoxyphenyl)pyrimidine-4-carboxamide;

N-(7-Fluoro-1-methyl-4-(1-methyl-1H-pyrazol-4-yl)-1H-indazol-5-yl)-2-(2-fluoro-6-methoxyphenyl)pyrimidine-4-carboxamide;

N-(7-Fluoro-4-(3-(hydroxymethyl)phenyl)-1-methyl-1H-indazol-5-yl)-2-(2-fluoro-6-methoxyphenyl)pyrimidine-4-carboxamide;

N-(7-Fluoro-4-(2-(hydroxymethyl)phenyl)-1-methyl-1H-indazol-5-yl)-2-(2-fluoro-6-methoxyphenyl)pyrimidine-4-carboxamide;

N-(4-(3-((Dimethylamino)methyl)phenyl)-7-fluoro-1-methyl-1H-indazol-5-yl)-2-(2-fluoro-6-methoxyphenyl)pyrimidine-4-carboxamide;

N-(4-((1S,4S)-2,5-diazabicyclo[2.2.1]heptan-2-yl)-7-fluoro-1-(2-hydroxyethyl)-1H-indazol-5-yl)-2-(2-fluoro-6-methoxyphenyl)pyrimidine-4-carboxamide;

N-(4-((1S,4S)-2,5-diazabicyclo[2.2.1]heptan-2-yl)-7-fluoro-1-(2-methoxyethyl)-1H-indazol-5-yl)-2-(2-fluoro-6-methoxyphenyl)pyrimidine-4-carboxamide;

N-(4-(4-(Dimethylamino)piperidin-1-yl)-3-iodo-1-methyl-1H-indazol-5-yl)-2-(2-fluoro-6-methoxyphenyl)pyrimidine-4-carboxamide;

N-(4-(4-(Dimethylamino)piperidin-1-yl)-1,3-dimethyl-1H-indazol-5-yl)-2-(2-fluoro-6-methoxyphenyl)pyrimidine-4-carboxamide;

N-(4-(4-(Dimethylamino)piperidin-1-yl)-1-methyl-3-phenyl-1H-indazol-5-yl)-2-(2-fluoro-6-methoxyphenyl)pyrimidine-4-carboxamide; and N-(4-(4-(Dimethylamino)piperidin-1-yl)-1-methyl-3-(1-methyl-1H-pyrazol-4-yl)-1H-indazol-5-yl)-2-(2-fluoro-6-methoxyphenyl)pyrimidine-4-carboxamide;

or a pharmaceutically acceptable salt thereof.

In some embodiments, provided herein is a compound selected from:

N-(4-((2S,4S)-4-Amino-2-(hydroxymethyl)pyrrolidin-1-yl)-7-fluoro-1-(2-methoxyethyl)-1H-indazol-5-yl)-2-(2-fluoro-6-methoxyphenyl)pyrimidine-4-carboxamide;

N-(4-((2S,4S)-4-Amino-2-(hydroxymethyl)pyrrolidin-1-yl)-7-fluoro-1-((R)-tetrahydrofuran-3-yl)-1H-indazol-5-yl)-2-(2-fluoro-6-methoxyphenyl)pyrimidine-4-carboxamide;

(R)—N-(7-Fluoro-4-(3-(hydroxymethyl)piperazin-1-yl)-2-methyl-2H-indazol-5-yl)-2-(2-fluoro-6-methoxyphenyl)pyrimidine-4-carboxamide;

N-(4-((2S,4S)-4-Amino-2-(hydroxymethyl)pyrrolidin-1-yl)-1-(3-cyanopyridin-4-yl)-7-fluoro-1H-indazol-5-yl)-2-(2-fluoro-6-methoxyphenyl)pyrimidine-4-carboxamide;

N-(4-((2S,4S)-2-(Aminomethyl)-4-hydroxypyrrolidin-1-yl)-7-fluoro-1-methyl-1H-indazol-5-yl)-2-(2-fluoro-6-methoxyphenyl)pyrimidine-4-carboxamide; and N-(4-((1S,4S)-2,5-Diazabicyclo[2.2.1]heptan-2-yl)-7-fluoro-1-(2-fluoroethyl)-1H-indazol-5-yl)-2-(2-fluoro-6-methoxyphenyl)pyrimidine-4-carboxamide;

or a pharmaceutically acceptable salt thereof.

In some embodiments, provided herein is a compound selected from:

N-(4-((2S,4S)-4-Amino-2-(hydroxymethyl)pyrrolidin-1-yl)-7-fluoro-1-(2-methoxyethyl)-1H-indazol-5-yl)-2-(2-fluoro-6-(methoxy-$d_3$)-3-methylphenyl)pyrimidine-4-carboxamide;

N-(4-((2S,4S)-4-Amino-2-(hydroxymethyl)pyrrolidin-1-yl)-7-fluoro-1-(2-methoxyethyl)-1H-indazol-5-yl)-2-(4-amino-2-fluoro-6-methoxyphenyl)pyrimidine-4-carboxamide;

N-(4-((2S,4S)-4-amino-2-(hydroxymethyl)pyrrolidin-1-yl)-7-fluoro-1-(2-methoxyethyl)-1H-indazol-5-yl)-2-(2-fluoro-6-methoxy-3-(methylcarbamoyl)phenyl)pyrimidine-4-carboxamide;

N-(4-((2S,4S)-4-Amino-2-(hydroxymethyl)pyrrolidin-1-yl)-7-fluoro-1-(2-methoxyethyl)-1H-indazol-5-yl)-2-(2-fluoro-6-methoxy-3-(1-methyl-1H-pyrazol-4-yl)phenyl)pyrimidine-4-carboxamide;

(R)—N-(7-Fluoro-1-methyl-4-(methyl(piperidin-3-yl)amino)-1H-indazol-5-yl)-2-(2-fluoro-6-methoxyphenyl)pyrimidine-4-carboxamide; and N-(4-((2S,4S)-4-Amino-2-(hydroxymethyl)pyrrolidin-1-yl)-7-fluoro-1-(2-methoxyethyl)-1H-indazol-5-yl)-6-(2-fluoro-6-methoxyphenyl)picolinamide, or a pharmaceutically acceptable salt thereof.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms. The term "$C_{n-m}$ dialkoxy" refers to a linking group of formula —O—($C_{n-m}$ alkyl)-O—, the alkyl group of which has n to m carbons. Example dialkyoxy groups include —OCH$_2$CH$_2$O— and OCH$_2$CH$_2$CH$_2$O—. In some embodiments, the two O atoms of a $C_{n-m}$ dialkoxy group may be attached to the same B atom to form a 5- or 6-membered heterocycloalkyl group.

The term "amino" refers to a group of formula —NH$_2$.

The term "carbonyl", employed alone or in combination with other terms, refers to a —C(=O)— group, which also may be written as C(O).

The term "cyano" or "nitrile" refers to a group of formula —C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include CF$_3$, C$_2$F$_5$, CHF$_2$, CH$_2$F, CCl$_3$, CHCl$_2$, C$_2$Cl$_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "sulfido" refers to a sulfur atom as a divalent substituent, forming a thiocarbonyl group (C=S) when attached to carbon.

The term "oxidized" in reference to a ring-forming N atom refers to a ring-forming N-oxide.

The term "oxidized" in reference to a ring-forming S atom refers to a ring-forming sulfonyl or ring-forming sulfinyl.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3, or 4 heteroatom ring members independently selected from nitrogen, sulfur and oxygen. In some embodiments, the heteroaryl has 5-10 ring atoms including carbon atoms and 1, 2, 3, or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, isoxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3-, and 2,6-naphthyridine), indolyl, isoindolyl, benzothiophenyl, benzofuranyl, benzisoxazolyl, imidazo[1,2-b]thiazolyl, purinyl, and the like. In some embodiments, the heteroaryl group is pyridone (e.g., 2-pyridone).

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl, isoindolyl, and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2. 1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 2,5-diazabicyclo[2.2.1]heptanyl (e.g., 2,5-diazabicyclo[2.2.1] heptan-2-yl); pyrrolidinyl; 2,5-diazabicyclo[2.2.1]octanyl; 2,5-diazabicyclo[2.2.2]octanyl (e.g., 2,5-diazabicyclo[2.2.2] octan-2-yl); morpholino; 6-oxo-2,7-diazaspiro[4.4]nonanyl (e.g., 6-oxo-2,7-diazaspiro[4.4]nonan-2-yl); azetidinyl; 2-oxopyrrolidinyl; piperidinyl; and piperazinyl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term, "compound," as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared, e.g., using a process as illustrated in the schemes below.

Compounds of Formula (IA) with a variety of substitution at position $R^1$ such as those described herein can be prepared using a process as illustrated in Scheme 1. In the process depicted in Scheme 1, an appropriately substituted 4-halo-1H-indazole 1-1 is nitrated using a variety of nitration conditions, including but not limited to nitric acid in the presence of sulfuric acid, to provide the corresponding nitrated derivative 1-2. Alkylation of the indazole using a suitable electrophile in the presence of a suitable base (e.g. cesium carbonate or sodium hydride) or Mitsunobu displacement of a suitable alcohol in the presence of triphenylphosphine and a suitable diimide, including but not limited to diethylazidodicarboxylate or Cu-catalyzed amination (e.g., in the presence of Cu catalyst and a ligand, such as CuI and phenanthroline), provides compounds of general formula 1-3. The halo substituent in 1-3 can be converted into the $R^1$ via a number of methods, including but not limited to nucleophilic displacement with an appropriate amine nucleophile in a suitable solvent (e.g., DMF, DMSO, dioxane) with a suitable base (e.g., triethylamine or DIPEA) or by a suitable cross-coupling, including but not limited to Buchwald (e.g. in the presence of a palladacycle precatalyst, such as RuPhod Pd G2) and Suzuki (e.g., in the presence of a palladacycle precatalyst, such as Xphos Pd G2), to give compounds of Formula 1-4. Examples of cross-coupling procedures include Stille (ACS Catalysis 2015, 5, 3040-3053) Suzuki (Tetrahedron 2002, 58, 9633-9695), Sonogashira (Chem. Soc. Rev. 2011, 40, 5084-5121), Negishi (ACS Catalysis 2016, 6, 1540-1552), Buchwald-Hartwig amination (Chem. Sci. 2011, 2, 27-50), Cu-catalyzed amination (Org. React. 2014, 85, 1-688) among others. Reduction of the nitro group with an appropriate reducing agent (e.g., iron in the presence of ammonium chloride or hydrogen gas in the presence of Pd/C catalyst) provides compounds of formula 1-5. Amide bond formation with an acid of formula 1-7 (e.g., using 1-[Bis(dimethylamino)methylene]-1H-1,2,3-triazolo[4,5-b]pyridinium 3-oxid hexafluorophosphate ("HATU") and a base such as Hunig's base) provides compounds of desired Formula (IA).

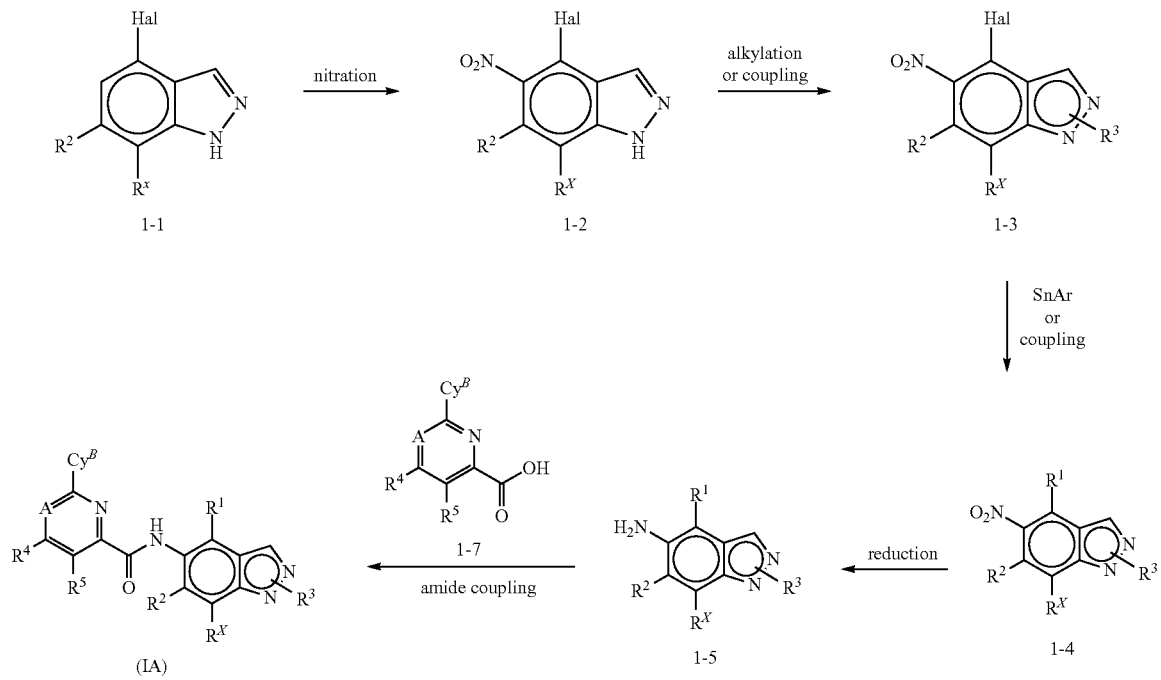

Scheme 1

The acids 1-7 can be prepared as illustrated in Scheme 2 by reaction of a halogen containing compound (i.e., X=chloro, bromo or iodo) of formula 1-6 and $Cy^B$-M (M=e.g., appropriately functionalized boron, stannyl or zinc species) using a cross coupling, such as Suzuki (e.g., in the presence of a palladacycle precatalyst, such as Xphos Pd G2) or Stille (e.g., in the precense of a palladium catalyst such as $(PPh_3)_2PdCl_2$ and a base such as triethylamine).

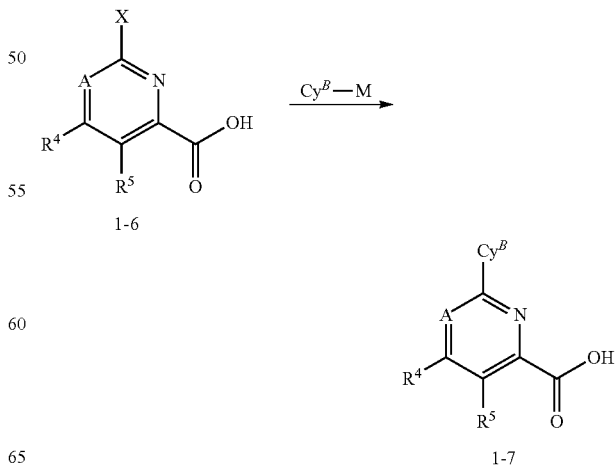

Scheme 2

Compounds of Formula (IB) with a variety of substitution at position R¹ such as those described herein can be prepared using a process as illustrated in Scheme 3. In the process depicted in Scheme 3, an appropriately substituted 4-halo-1H-indazole 2-1 is nitrated using a variety of nitration conditions, i.e. nitric acid in the presence of sulfuric acid, to provide the corresponding nitrated derivative 2-2. Iodination of 2-2 using standard conditions, i.e. NIS in an appropriate solvent such as DMF, provides compounds of formula 2-3. Cross coupling (e.g., Suzuki in the presence of a paladium catalyst, such as PdCl₂dppf) provides compounds of formula 2-4. Alkylation of the indazole using a suitable electrophile in the presence of a suitable base (e.g., cesium carbonate or sodium hydride) or Mitsunobu displacement of a suitable alcohol in the presence of triphenylphosphine and a suitable diimide, e.g., diethylazidodicarboxylate or Cu-catalyzed amination (e.g., in the presence of Cu catalyst and a ligand, such as CuI and phenanthroline), provides compounds of general formula 2-5. Compounds of formula 2-5 can be converted into compounds of general formula (IB) in an analogous fashion to that described in Scheme 1 for compounds 1-5.

11037-48). Activated HPK1 phosphorylates SLP-76 on Ser376 or BLNK on Thr152, leading to the recruitment of signaling molecule 14-3-3 and ultimate ubiquitination-mediated degradation of SLP-76 or BLNK (Liou, J., et al., Immunity, 2000. 12(4): p. 399-408; Di Bartolo, V., et al., J Exp Med, 2007. 204(3): p. 681-91). As SLP-76 and BLNK are essential for TCR/BCR-mediated signaling activation (e.g. ERK, phospholipase Cγ1, calcium flux, and NFAT activation), HPK1-mediated downregulation of these adaptor proteins provide a negative feedback mechanism to attenuate signaling intensity during T cell or B cell activation (Wang, X., et al., J Biol Chem, 2012. 287(14): p. 11037-48).

The bone marrow-derived dendritic cells (BDMCs) from HPK1 knockout mice showed higher expression of co-stimulatory molecules (e.g. CD80/CD86) and enhanced production of proinflammatory cytokines (IL-12, TNF-α etc), and demonstrated superior ability to stimulate T cell proliferation in vitro and in vivo as compared to wild-type DCs (Alzabin, S., et al., J Immunol, 2009. 182(10): p. 6187-94). These data suggest that HPK1 is also an important negative regulator of dendritic cell activation (Alzabin, S., et al., J

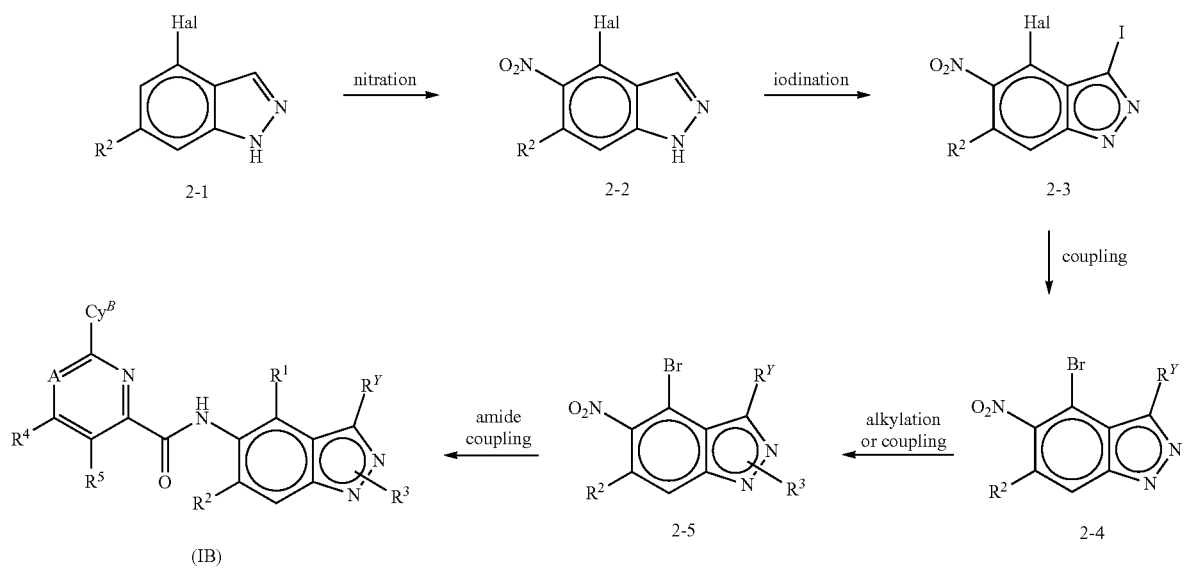

Scheme 3

HPK1 Kinase

Studies have established that HPK1 is a negative regulator of T cell and B cell activation (Hu, M. C., et al., Genes Dev, 1996. 10(18): p. 2251-64; Kiefer, F., et al., EMBO J, 1996. 15(24): p. 7013-25). HPK1-deficient mouse T cells showed dramatically increased activation of TCR proximal signaling, enhanced IL-2 production, and hyper-proliferation in vitro upon anti-CD3 stimulation (Shui, J. W., et al., Nat Immunol, 2007. 8(1): p. 84-91). Similar to T cells, HPK1 knockout B cells produced much higher levels of IgM and IgG isoforms after KLH immunization and displayed hyper-proliferation potentially as a result of enhanced BCR signaling. Wang, X., et al., J Biol Chem, 2012. 287(14): p. 11037-48. Mechanistically, during TCR or BCR signaling, HPK1 is activated by LCK/ZAP70 (T cells) or SYK/LYN (B cells) mediated-Tyr379 phosphorylation and its subsequent binding to adaptor protein SLP-76 (T cells) or BLNK (B cells) (Wang, X., et al., J Biol Chem, 2012. 287(14): p.

Immunol, 2009. 182(10): p. 6187-94). However, the signaling mechanisms underlying HPK-1 mediated negative regulation of DC activation remains to be elucidated.

In contrast, HPK1 appears to be a positive regulator of suppressive functions of regulatory T cells (Treg) (Sawasdikosol, S. et al., The journal of immunology, 2012. 188 (supplement 1): p. 163). HPK1 deficient mouse Foxp3+ Tregs were defective in suppressing TCR-induced effector T cell proliferation, and paradoxically gained the ability to produce IL-2 following TCR engagement (Sawasdikosol, S. et al., The Journal of Immunology, 2012. 188(supplement 1): p. 163). These data suggest that HPK1 is an important regulator of Treg functions and peripheral self-tolerance.

HPK1 was also involved in PGE2-mediated inhibition of CD4+ T cell activation (Ikegami, R., et al., J Immunol, 2001. 166(7): p. 4689-96). Studies published in US 2007/0087988 indicated that HPK1 kinase activity was increased by exposure to physiological concentrations of PGE2 in CD4+ T cells and this effect was mediated by PEG2-induced PKA activation. The proliferation of HPK1 deficient T cells was resistant to the suppressive effects of PGE2 (see US 2007/0087988). Therefore, PGE2-mediated activation of HPK1 may represent a novel regulatory pathway of modulating immune response.

The present disclosure provides methods of modulating (e.g., inhibiting) HPK1 activity, by contacting HPK1 with a compound of the invention, or a pharmaceutically acceptable salt thereof. In some embodiments, the contacting can be administering to a patient a compound provided herein, or a pharmaceutically acceptable salt thereof. In certain embodiments, the compounds of the present disclosure, or pharmaceutically acceptable salts thereof, are useful for therapeutic administration to enhance, stimulate and/or increase immunity in cancer. For example, a method of treating a disease or disorder associated with inhibition of HPK1 interaction can include administering to a patient in need thereof a therapeutically effective amount of a compound provided herein, or a pharmaceutically acceptable salt thereof. The compounds of the present disclosure can be used alone, in combination with other agents or therapies or as an adjuvant or neoadjuvant for the treatment of diseases or disorders, including cancers. For the uses described herein, any of the compounds of the disclosure, including any of the embodiments thereof, may be used.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, triple-negative breast cancer, colon cancer and lung cancer (e.g. non-small cell lung cancer and small cell lung cancer). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, diseases and indications that are treatable using the compounds of the present disclosure include, but are not limited to, hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, Waldenstrom's Macroglubulinemia, hairy cell lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers.

In some embodiments, HPK1 inhibitors may be used to treat tumors producing PGE2 (e.g. Cox-2 overexpressing tumors) and/or adenosine (CD73 and CD39 over-expressing tumors). Overexpression of Cox-2 has been detected in a number of tumors, such as colorectal, breast, pancreatic and lung cancers, where it correlates with a poor prognosis. Overexpression of COX-2 has been reported in hematological cancer models such as RAJI (Burkitt's lymphoma) and U937 (acute promonocytic leukemia) as well as in patient's blast cells. CD73 is up-regulated in various human carcinomas including those of colon, lung, pancreas and ovary. Importantly, higher expression levels of CD73 are associated with tumor neovascularization, invasiveness, and metastasis and with shorter patient survival time in breast cancer.

As used herein, the term "contacting" refers to the bringing together of the indicated moieties in an in vitro system or an in vivo system such that they are in sufficient physical proximity to interact.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

I. Immune-Checkpoint Therapies

In some embodiments, the HPK1 inhibitors provided herein can be used in combination with one or more immune checkpoint inhibitors for the treatment of cancer as described herein. Compounds of the present disclosure can be used in combination with one or more immune checkpoint inhibitors. Exemplary immune checkpoint inhibitors include inhibitors against immune checkpoint molecules such as CD20, CD28, CD39, CD40, CD122, CD96, CD73, CD47, GITR, CSF1R, JAK, PI3K delta, PI3K gamma, TAM, arginase, CD137 (also known as 4-1BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of CSF1R, e.g., an anti-CSF1R antibody. In some embodiments, the anti-CSF1R antibody is IMC-CS4 or RG7155.

In some embodiments, the inhibitor of an immune checkpoint molecule is an inhibitor of LAG3, e.g., an anti-LAG3 antibody. In some embodiments, the anti-LAG3 antibody is BMS-986016, LAG525, IMP321, GSK2831781, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MEDI6469, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196. An example of an arginase inhibitor is CB-1158.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Examples of agents that may be combined with compounds of the present disclosure include inhibitors of the PI3K-AKT-mTOR pathway, inhibitors of the Raf-MAPK pathway, inhibitors of JAK-STAT pathway, inhibitors of beta catenin pathway, inhibitors of notch pathway, inhibitors of hedgehog pathway, inhibitors of Pim kinases, and inhibitors of protein chaperones and cell cycle progression. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors for the treatment of diseases, such as cancer. Examples of cancers include solid tumors and liquid tumors, such as blood cancers. For example, the compounds of the present disclosure can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer. Non-limiting examples of inhibitors that can be combined with the compounds of the present disclosure for treatment of cancers include an FGFR inhibitor (FGFR1, FGFR2, FGFR3 or FGFR4, e.g., AZD4547, BAY1187982, ARQ087, BGJ398, BIBF1120, TKI258, lucitanib, dovitinib, TAS-120, JNJ-42756493, Debio1347, INCB54828, INCB62079 and INCB63904), a JAK inhibitor (JAK1 and/or JAK2, e.g., ruxolitinib, baricitinib or INCB39110), an IDO inhibitor (e.g., epacadostat and NLG919), an LSD1 inhibitor (e.g., GSK2979552, INCB59872 and INCB60003), a TDO inhibitor, a PI3K-delta inhibitor (e.g., INCB50797 and INCB50465), a PI3K-gamma inhibitor such as a PI3K-gamma selective inhibitor, a CSF1R inhibitor (e.g., PLX3397 and LY3022855), a TAM receptor tyrosine kinases (Tyro-3, Axl, and Mer), an angiogenesis inhibitor, an interleukin receptor inhibitor, bromo and extra terminal family members inhibitors (for example, bromodomain inhibitors or BET inhibitors such as OTX015, CPI-0610, INCB54329 and INCB57643) and an adenosine receptor antagonist or combinations thereof. Inhibitors of HDAC such as panobinostat and vorinostat. Inhibitors of c-Met such as onartumzumab, tivantnib, and INC-280. Inhibitors of BTK such as ibrutinib. Inhibitors of mTOR such as rapamycin, sirolimus, temsirolimus, and everolimus. Inhibitors of Raf, such as vemurafenib and dabrafenib. Inhibitors of MEK such as trametinib, selumetinib and GDC-0973. Inhibitors of Hsp90 (e.g., tanespimycin), cyclin dependent kinases (e.g., palbociclib), PARP (e.g., olaparib) and Pim kinases (LGH447, INCB053914 and SGI-1776) can also be combined with compounds of the present disclosure.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include bendamustine, nitrogen mustards, ethylenimine derivatives, alkyl sulfonates, nitrosoureas and triazenes, uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, CAR (Chimeric antigen receptor) T cell treatment as a booster for T cell activation, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, abiraterone, afatinib, aflibercept, aldesleukin, alemtuzumab, alitretinoin, allopurinol, altretamine, amsacrine, anastrozole, aphidicolon, arsenic trioxide, asparaginase, axitinib, azacitidine, bevacizumab, bexarotene, baricitinib, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, nofetumomab, oserelin, oxaliplatin, paclitaxel, pamidronate, panitumumab, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, ruxolitinib, sorafenib, streptozocin, sunitinib, sunitinib maleate, tamoxifen, tegafur, temozolomide, teniposide, testolactone, thalidomide, thioguanine, thiotepa, topotecan, toremifene, tositumomab, trastuzumab, tretinoin, triptorelin, uracil mustard, valrubicin, vandetanib, vinblastine, vincristine, vindesine, vinorelbine, vorinostat, and zoledronate.

Other anti-cancer agent(s) include antibody therapeutics such as trastuzumab (Herceptin), antibodies to costimulatory molecules such as CTLA-4 (e.g., ipilimumab or tremelimumab), 4-1BB, antibodies to PD-1 and PD-L1, or antibodies to cytokines (IL-10, TGF-β, etc.). Examples of antibodies to PD-1 and/or PD-L1 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

Other anti-cancer agents include inhibitors of kinases associated cell proliferative disorder. These kinases include but not limited to Aurora-A, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, PAK1, PAK2, PAK3, PAK4, PDK1, PKA, PKC, Rsk and SGK.

Other anti-cancer agents also include those that block immune cell migration such as antagonists to chemokine receptors, including CCR2 and CCR4.

The compounds of the present disclosure can further be used in combination with one or more anti-inflammatory agents, steroids, immunosuppressants or therapeutic antibodies. The steroids include but are not limited to 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

The compounds of the present disclosure can also be used in combination with lonafarnib (SCH6636), tipifarnib (R115777), L778123, BMS 214662, tezacitabine (MDL 101731), Sml1, triapine, didox, trimidox and amidox.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

The compounds of the present disclosure can be used in combination with bone marrow transplant for the treatment of a variety of tumors of hematopoietic origin.

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis (POM)-PMEA]; lobucavir (BMS-180194); BCH-10652; emitricitabine [(−)-FTC]; beta-L-FD4 (also called beta-L-D4C and named beta-L-2′, 3′-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

When more than one pharmaceutical agent is administered to a patient, they can be administered simultaneously, separately, sequentially, or in combination (e.g., for more than two agents).

In some embodiments, the compounds of the disclosure can be used in combination with INCB086550.

Formulation, Dosage Forms and Administration

When employed as pharmaceuticals, the compounds of the present disclosure can be administered in the form of pharmaceutical compositions. Thus the present disclosure provides a composition comprising a compound of Formula (I) or any of the formulas as described herein, a compound as recited in any of the claims and described herein, or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Labeled Compounds and Assay Methods

Another aspect of the present invention relates to labeled compounds of the disclosure (radio-labeled, fluorescent-labeled, etc.) that would be useful not only in imaging techniques but also in assays, both in vitro and in vivo, for localizing and quantitating HPK1 protein in tissue samples, including human, and for identifying HPK1 ligands by inhibition binding of a labeled compound. Substitution of one or more of the atoms of the compounds of the present disclosure can also be useful in generating differentiated ADME (Adsorption, Distribution, Metabolism and Excretion). Accordingly, the present invention includes HPK1 binding assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups in Formula (I) can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. J. *Med. Chem.* 2011, 54, 201-210; R. Xu et. al. J. *Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro adenosine receptor labeling and competition assays, compounds that incorporate $^{3}$H, $^{14}$C, $^{82}$Br, $^{125}$I, $^{131}$I or $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments, the radionuclide is selected from the group consisting of $^{3}$H, $^{14}$C, $^{125}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the invention can be used in a screening assay to identify and/or evaluate compounds. For example, a newly synthesized or identified compound (i.e., test compound) which is labeled can be evaluated for its ability to bind a HPK1 protein by monitoring its concentration variation when contacting with the HPK1, through tracking of the labeling. For example, a test compound (labeled) can be evaluated for its ability to reduce binding of another compound which is known to bind to a HPK1 protein (i.e., standard compound). Accordingly, the ability of a test compound to compete with the standard compound for binding to the HPK1 protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, e.g., in the treatment or prevention of diseases or disorders associated with the activity of HPK1, such as cancer or infections, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of HPK1 according to at least one assay described herein.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Haque, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004). The compounds separated were typically subjected to analytical liquid chromatography mass spectrometry (LCMS) for purity check.

The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 m particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, J. Comb. Chem., 6, 874-883 (2004)]. Typically, the flow rate used with the 30×100 mm column was 60 mL/minute. pH=10 purifications: Waters XBridge $C_{18}$ 5 μm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, J. Comb. Chem., 6, 874-883 (2004)]. Typically, the flow rate used with 30×100 mm column was 60 mL/minute."

The following abbreviations may be used herein: AcOH (acetic acid); $Ac_2O$ (acetic anhydride); aq. (aqueous); atm. (atmosphere(s)); Boc (t-butoxycarbonyl); BOP ((benzotriazol-1-yloxy)tris(dimethylamino)phosphonium hexafluorophosphate); br (broad); Cbz (carboxybenzyl); calc. (calculated); d (doublet); dd (doublet of doublets); DBU (1,8-diazabicyclo[5.4.0]undec-7-ene); DCM (dichloromethane); DIAD (N, N'-diisopropyl azidodicarboxylate); DIEA (N,N-diisopropylethylamine); DIPEA (N, N-diisopropylethylamine); DIBAL (diisobutylaluminium hydride); DMF (N, N-dimethylformamide); Et (ethyl); EtOAc (ethyl acetate); FCC (flash column chromatography); g (gram(s)); h (hour(s)); HATU (N, N, N', N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography—mass spectrometry); LDA (lithium diisopropylamide); m (multiplet); M (molar); mCPBA (3-chloroperoxybenzoic acid); MS (Mass spectrometry); Me (methyl); MeCN (acetonitrile); MeOH (methanol); mg (milligram(s)); min. (minutes(s)); mL (milliliter(s)); mmol (millimole(s)); N (normal); nM (nanomolar); NMP (N-methylpyrrolidinone); NMR (nuclear magnetic resonance spectroscopy); OTf (trifluoromethanesulfonate); Ph (phenyl); pM (picomolar); RP-HPLC (reverse phase high performance liquid chromatography); r.t. (room temperature), s (singlet); t (triplet or tertiary); TBS (tert-butyldimethylsilyl); tert (tertiary); tt (triplet of triplets); TFA (trifluoroacetic acid); THF (tetrahydrofuran); g (microgram(s)); μL (microliter(s)); M (micromolar); wt % (weight percent).

Example 1. N-(4-((1S,4S)-2,5-Diazabicyclo[2.2.1]heptan-2-yl)-7-fluoro-1-methyl-1H-indazol-5-yl)-2-(2-fluoro-6-methoxyphenyl)pyrimidine-4-carboxamide and N-(4-((1S,4S)-2,5-diazabicyclo[2.2.1]heptan-2-yl)-7-fluoro-2-methyl-2H-indazol-5-yl)-2-(2-fluoro-6-methoxyphenyl)pyrimidine-4-carboxamide

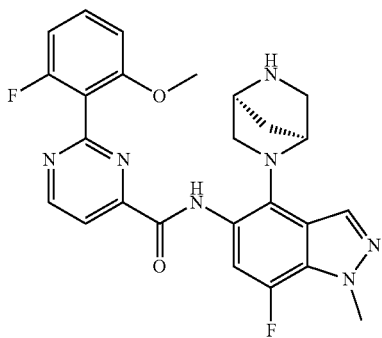

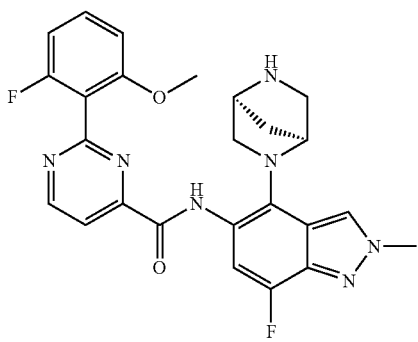

Step 1. 4-Bromo-7-fluoro-5-nitro-1H-indazole

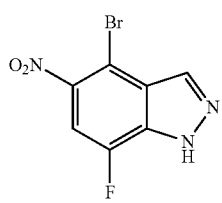 [SMILES: O=[N+]([O-])c1cc(F)c2[nH]ncc2c1Br]

A solution of 4-bromo-7-fluoro-1H-indazole (10 g, 46.5 mmol) in sulfuric acid (74.4 mL) at 0° C. was treated with nitric acid (18.60 mL) dropwise. The reaction mixture was warmed to room temperature and stirred for 30 mins. The mixture was then poured into ice and the resulting precipitate was collected by filtration and washed with water. The solid was air dried overnight and used in the next step without further purification (8.75 g, 70%). LCMS calculated for $C_7H_4BrFN_3O_2(M+H)^+$: m/z=260.0/262.0; found 260.0/262.0.

Step 2. A mixture of 4-bromo-7-fluoro-1-methyl-5-nitro-1H-indazole and 4-bromo-7-fluoro-2-methyl-5-nitro-2H-indazole

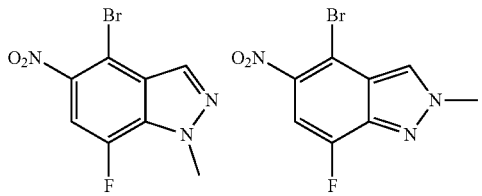

Procedure A. A suspension of 4-bromo-7-fluoro-5-nitro-1H-indazole (2.5 g, 9.61 mmol) and potassium carbonate (6.64 g, 48.1 mmol) in acetonitrile (48.1 mL) was treated with methyl iodide (0.902 mL, 14.42 mmol) and the resulting reaction mixture was stirred at room temperature for 5 hrs. The mixture was then treated with water and the desired product was extracted with ethyl acetate. The combined organic phases were washed with water and brine, dried over sodium sulfate and concentrated. The crude solid was used in the next step without further purification (1.95 g, 74%). The product consisted of a ~1:1 ratio of regioisomers. Peak 1: LCMS calculated for $C_8H_6BrFN_3O_2(M+H)^+$: m/z=274.0/276.0; found 274.0/276.0. Peak 2: LCMS calculated for $C_8H_6BrFN_3O_2(M+H)^+$: m/z=274.0/276.0; found 274.0/276.0.

Procedure B. A solution of 4-bromo-7-fluoro-5-nitro-1H-indazole (500 mg, 1.923 mmol) in ethyl acetate (9.615 mL) was treated with trimethyloxonium tetrafluoroborate (370 mg, 2.500 mmol) and the reaction mixture stirred at room temperature overnight. The mixture was washed in turn with saturated aqueous sodium bicarbonate, water, and brine. The mixture was then dried over sodium sulfate and concentrated. The crude product was used in the next step without further purification. This procedure affords the 2H isomer. LCMS calculated for $C_8H_6BrFN_3O_2$ $(M+H)^+$: m/z=274.0/276.0; found 274.0/276.0.

Step 3. 2-(2-Fluoro-6-methoxyphenyl)pyrimidine-4-carboxylic acid

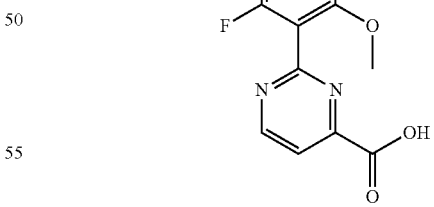

A mixture of 2-chloropyrimidine-4-carboxylic acid (9 g, 56.8 mmol), (2-fluoro-6-methoxyphenyl)boronic acid (11.58 g, 68.1 mmol), XPhos Pd G2 (1.340 g, 1.703 mmol) and potassium phosphate (24.10 g, 114 mmol) was mixed with 1,4-dioxane (100 mL) and water (20.00 mL). The reaction mixture was heated to 80° C. for 2 h under a nitrogen atmosphere. The reaction mixture was then cooled to room temperature, treated with water and diluted with ethyl acetate. The aqueous phase was separated, and acidified with 1 N HCl. The precipitated solid was collected by filtration and washed with water. After air drying, the solid was used in the next step without further purification. LCMS calculated for $C_{12}H_{10}FN_2O_3(M+H)^+$: m/z=249.2; found 249.2.

Step 4. A mixture of (1S,4S)-tert-butyl 5-(7-fluoro-1-methyl-5-nitro-1H-indazol-4-yl)-2,5-diazabicyclo[2.2.1]heptane-2-carboxylate and (1S,4S)-tert-butyl 5-(7-fluoro-2-methyl-5-nitro-2H-indazol-4-yl)-2,5-diazabicyclo[2.2.1]heptane-2-carboxylate

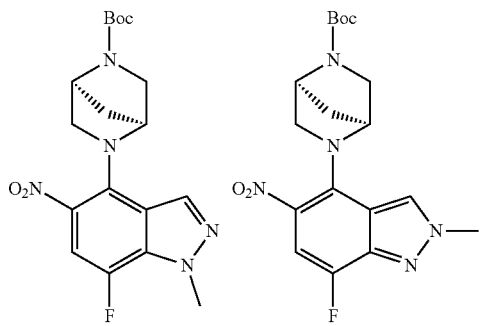 [SMILES: Cn1ncc2c(N3C[C@@H]4C[C@H]3CN4C(=O)OC(C)(C)C)c([N+](=O)[O-])cc(F)c21 ; Cn1cc2c(N3C[C@@H]4C[C@H]3CN4C(=O)OC(C)(C)C)c([N+](=O)[O-])cc(F)c2n1]

A mixture of 4-bromo-7-fluoro-1-methyl-5-nitro-1H-indazole and 4-bromo-7-fluoro-2-methyl-5-nitro-2H-indazole (from Step 2, 250 mg, 0.912 mmol), tert-butyl (1S,4S)-2,5-diazabicyclo[2.2.1]heptane-2-carboxylate (181 mg, 0.912 mmol), BINAP (56.8 mg, 0.091 mmol), palladium(II) acetate (20.48 mg, 0.091 mmol) and cesium carbonate (594 mg, 1.824 mmol) in toluene (3 mL) was stirred at 100° C. for 2 h under a nitrogen atmosphere. The mixture was then diluted with dichloromethane and filtered through a pad of Celite. The filtrate was concentrated and the resultant residue purified by Biotage Isolera™ (flash purification system with 20-100% ethyl acetate in hexane) to provide the desired product (156 mg, 44%) as a ~1:1 mixture of regioisomers of the indazole core. Peak 1: LCMS calculated for $C_{18}H_{23}FN_5O_4$ (M+H)$^+$: m/z=392.2; found 392.2. Peak 2: LCMS calculated for $C_{18}H_{23}FN_5O_4$ (M+H)$^+$: m/z=392.2; found 392.2.

Step 5. N-(4-((S,4S)-2,5-diazabicyclo[2.2.1]heptan-2-yl)-7-fluoro-1-methyl-1H-indazol-5-yl)-2-(2-fluoro-6-methoxyphenyl)pyrimidine-4-carboxamide and N-(4-((1S,4S)-2,5-diazabicyclo[2.2.1]heptan-2-yl)-7-fluoro-2-methyl-2H-indazol-5-yl)-2-(2-fluoro-6-methoxyphenyl)pyrimidine-4-carboxamide A solution of tert-butyl (1S,4S)-5-(7-fluoro-1-methyl-5-nitro-1H-indazol-4-yl)-2,5-diazabicyclo[2.2.1]heptane-2-carboxylate and tert-butyl (1S,4S)-5-(7-fluoro-2-methyl-5-nitro-2H-indazol-4-yl)-2,5-diazabicyclo[2.2.1]heptane-2-carboxylate (156 mg, 0.399 mmol) in a 1:1:1 (v/v/v) mixture of THF/MeOH/water (4 mL) was treated with iron (89 mg, 1.594 mmol) and ammonium chloride (128 mg, 2.391 mmol). The reaction mixture was heated to 80° C. for 1 h, cooled to room temperature, diluted with ethyl acetate and filtered through a pad of Celite. The filtrate was washed with water and brine, dried over sodium sulfate and concentrated. The residue was treated with 2-(2-fluoro-6-methoxyphenyl)pyrimidine-4-carboxylic acid (109 mg, 0.438 mmol), HATU (182 mg, 0.478 mmol), DMF (1993 μl) and Hunig's base (209 μL, 1.196 mmol). The resulting mixture was stirred at room temperature for 30 mins and then treated with water. The resulting precipitate was collected by filtration, washed with water and hexane, and air dried overnight. The crude solid was treated with TFA (3 mL) and the mixture was stirred at room temperature for 30 mins. The mixture was then diluted with methanol and purified with prep-LCMS (XBridge C18 column, eluting with a gradient of acetonitrile/water containing 0.1% TFA, at flow rate of 60 mL/min). Both the 1H and 2H isomers were isolated as the TFA salts of the title compounds. Peak 1 was assigned as the 2H isomer, and peak 2 was assigned as the 1H isomer. Peak 1: LCMS calculated for $C_{25}H_{24}F_2N_7O_2(M+H)^+$: m/z=492.2; Found: 492.2. $^1$H NMR (500 MHz, DMSO) δ 10.44 (s, 1H), 9.27 (d, J=5.0 Hz, 1H), 9.14 (s, 1H), 8.87 (s, 1H), 8.77 (s, 1H), 8.15 (d, J=5.0 Hz, 1H), 7.63 (d, J=12.3 Hz, 1H), 7.61-7.51 (m, 1H), 7.08 (d, J=8.5 Hz, 1H), 7.00 (t, J=8.8 Hz, 1H), 4.45 (s, 1H), 4.38 (s, 1H), 4.19 (s, 3H), 3.78 (s, 3H), 3.70 (d, J=10.3 Hz, 1H), 3.48 (d, J=10.9 Hz, 1H), 3.32 (s, 1H), 3.18 (t, J=9.4 Hz, 1H), 2.03 (d, J=10.9 Hz, 1H), 1.78 (d, J=10.5 Hz, 1H).

Peak 2: LCMS calculated for $C_{25}H_{24}F_2N_7O_2(M+H)^+$: m/z=492.2; Found: 492.2. $^1$H NMR (500 MHz, DMSO) δ 10.45 (s, 1H), 9.27 (d, J=5.0 Hz, 1H), 9.07 (s, 1H), 8.78 (s, 1H), 8.37 (s, 1H), 8.14 (d, J=5.0 Hz, 1H), 7.72 (d, J=12.7 Hz, 1H), 7.56 (q, J=8.4 Hz, 1H), 7.08 (d, J=8.5 Hz, 1H), 7.00 (t, J=8.8 Hz, 1H), 4.49 (s, 1H), 4.43 (s, 1H), 4.17 (s, 3H), 3.78 (s, 3H), 3.76 (s, 1H), 3.51 (d, J=10.8 Hz, 1H), 3.32 (d, J=9.7 Hz, 1H), 3.26-3.16 (m, 1H), 2.05 (d, J=10.7 Hz, 1H), 1.79 (d, J=10.6 Hz, 1H).

Example 2. (1S,4S)—N-Ethyl-5-(7-fluoro-5-(2-(2-fluoro-6-methoxyphenyl)pyrimidine-4-carboxamido)-1-methyl-1H-indazol-4-yl)-2,5-diazabicyclo[2.2.1]heptane-2-carboxamide

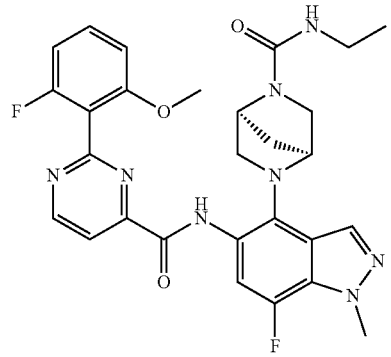 [SMILES: CCNC(=O)N1C[C@@H]2C[C@H]1CN2c1c(NC(=O)c2ccnc(-c3c(F)cccc3OC)n2)cc(F)c2c1cnn2C]

A solution of N-(4-((1S,4S)-2,5-diazabicyclo[2.2.1]heptan-2-yl)-7-fluoro-1-methyl-1H-indazol-5-yl)-2-(2-fluoro-6-methoxyphenyl)pyrimidine-4-carboxamide (from Example 1, Step 5; 10 mg, 0.0065 mmol) and hunig's base (9.4 μL, 0.054 mmol) in dichloromethane (215 μL) was treated with ethyl isocyanate (1.5 μL, 0.021 mmol). The reaction mixture was stirred at 60° C. for 1 h, diluted with methanol and purified with prep-LCMS (XBridge C18 column, eluting with a gradient of acetonitrile/water containing 0.1% ammonium hydroxide, at flow rate of 60 mL/min). LCMS calculated for $C_{28}H_{29}F_2N_8O_3$ (M+H)$^+$: m/z=563.2; Found: 563.2.

Example 3. N-(4-((2S,4S)-4-Amino-2-(hydroxymethyl)pyrrolidin-1-yl)-7-fluoro-1-methyl-1H-indazol-5-yl)-2-(2-fluoro-6-methoxyphenyl)pyrimidine-4-carboxamide and N-(4-((2S,4S)-4-amino-2-(hydroxymethyl)pyrrolidin-1-yl)-7-fluoro-2-methyl-2H-indazol-5-yl)-2-(2-fluoro-6-methoxyphenyl)pyrimidine-4-carboxamide Example 4. (R)—N-(4-(3-Aminopyrrolidin-1-yl)-7-fluoro-1-methyl-1H-indazol-5-yl)-2-(2-fluoro-6-methoxyphenyl)pyrimidine-4-carboxamide and (R)—N-(4-(3-aminopyrrolidin-1-yl)-7-fluoro-2-methyl-2H-indazol-5-yl)-2-(2-fluoro-6-methoxyphenyl)pyrimidine-4-carboxamide

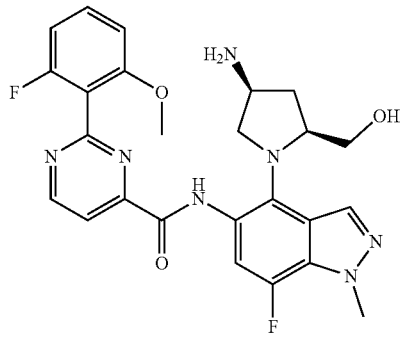

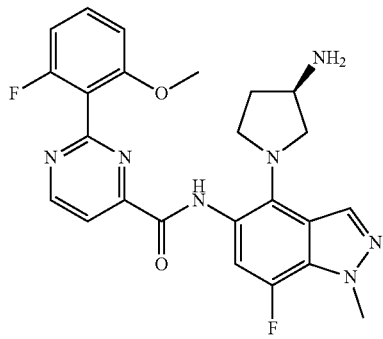

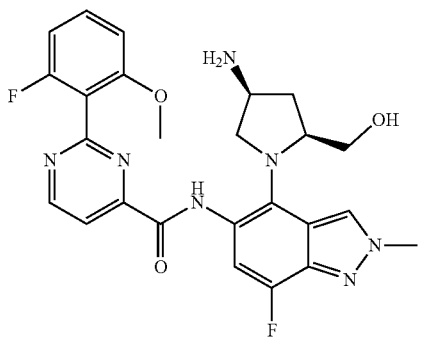

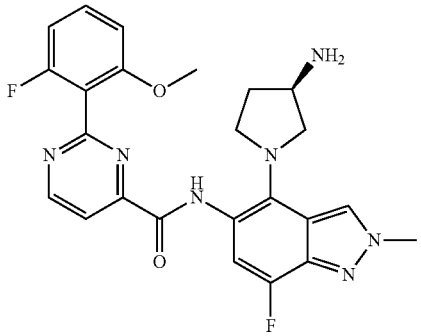

The TFA salts of the title compounds were prepared according to the procedures described in Example 1, using tert-butyl (3S,5S)-5-(hydroxymethyl)pyrrolidin-3-ylcarbamate instead of tert-butyl (1S,4S)-2,5-diazabicyclo[2.2.1]heptane-2-carboxylate as starting material. Peak 1: LCMS calculated for $C_{25}H_{26}F_2N_7O_3(M+H)^+$: m/z=510.2; Found: 510.2. Peak 2: LCMS calculated for $C_{25}H_{26}F_2N_7O_3(M+H)^+$: m/z=510.2; Found: 510.2. $^1$H NMR (500 MHz, DMSO) δ 10.73 (s, 1H), 9.26 (d, J=5.0 Hz, 1H), 8.34 (s, 1H), 8.26 (d, J=13.5 Hz, 1H), 8.17 (d, J=5.0 Hz, 1H), 7.91 (s, 2H), 7.60-7.46 (m, 1H), 7.06 (d, J=8.5 Hz, 1H), 7.00 (t, J=8.7 Hz, 1H), 4.19 (s, 3H), 3.77 (s, 5H), 3.55 (dd, J=9.9, 4.9 Hz, 1H), 3.43-3.29 (m, 2H), 3.17 (q, J=10.8, 9.8 Hz, 2H), 2.74-2.59 (m, 1H), 1.83 (d, J=13.5 Hz, 1H).

The TFA salts of the title compounds were prepared according to the procedures described in Example 1, using (R)-tert-butyl pyrrolidin-3-ylcarbamate instead of tert-butyl (1S,4S)-2,5-diazabicyclo[2.2.1]heptane-2-carboxylate as starting material. Peak 1: LCMS calculated for $C_{24}H_{24}F_2N_7O_2(M+H)^+$: m/z=480.2; Found: 480.2. Peak 2: LCMS calculated for $C_{24}H_{24}F_2N_7O_2(M+H)^+$: m/z=480.2; Found: 480.2. Peak 2: $^1$H NMR (500 MHz, DMSO) δ 10.94 (s, 1H), 9.28 (d, J=5.0 Hz, 1H), 8.38 (d, J=2.2 Hz, 1H), 8.14 (d, J=5.0 Hz, 1H), 8.12 (d, J=13.2 Hz, 1H), 8.07 (s, 1H), 7.58 (q, J=8.4 Hz, 1H), 7.09 (d, J=8.5 Hz, 1H), 7.03 (t, J=8.8 Hz, 1H), 4.18 (s, 3H), 3.79 (s, 3H), 3.68-3.57 (m, 2H), 3.51 (q, J=8.2 Hz, 2H), 3.29 (dd, J=9.3, 5.1 Hz, 1H), 3.21 (td, J=8.5, 3.4 Hz, 1H), 2.06 (dq, J=16.1, 8.1 Hz, 1H), 1.97-1.88 (m, 1H).

Example 5. N-(4-((1S,4S)-2,5-Diazabicyclo[2.2.2]octan-2-yl)-7-fluoro-1-methyl-1H-indazol-5-yl)-2-(2-fluoro-6-methoxyphenyl)pyrimidine-4-carboxamide and N-(4-((1S,4S)-2,5-diazabicyclo[2.2.2]octan-2-yl)-7-fluoro-2-methyl-2H-indazol-5-yl)-2-(2-fluoro-6-methoxyphenyl)pyrimidine-4-carboxamide

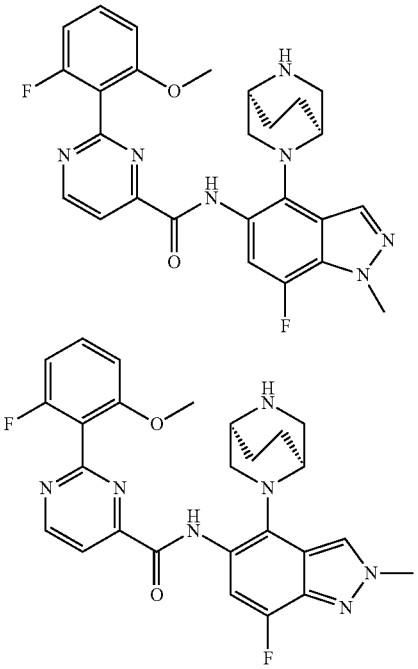

The TFA salts of the title compounds were prepared according to the procedures described in Example 1, using (1S,4S)-tert-butyl 2,5-diazabicyclo[2.2.2]octane-2-carboxylate instead of tert-butyl (1S,4S)-2,5-diazabicyclo[2.2.1]heptane-2-carboxylate as starting material. Peak 1: LCMS calculated for $C_{26}H_{26}F_2N_7O_2(M+H)^+$: m/z=506.2; Found: 506.2. Peak 2: LCMS calculated for $C_{26}H_{26}F_2N_7O_2(M+H)^+$: m/z=506.2; Found: 506.2.

Example 6. (R)—N-(7-Fluoro-4-(2-(hydroxymethyl)pyrrolidin-1-yl)-1-methyl-1H-indazol-5-yl)-2-(2-fluoro-6-methoxyphenyl)pyrimidine-4-carboxamide and (R)—N-(7-fluoro-4-(2-(hydroxymethyl)pyrrolidin-1-yl)-2-methyl-2H-indazol-5-yl)-2-(2-fluoro-6-methoxyphenyl)pyrimidine-4-carboxamide

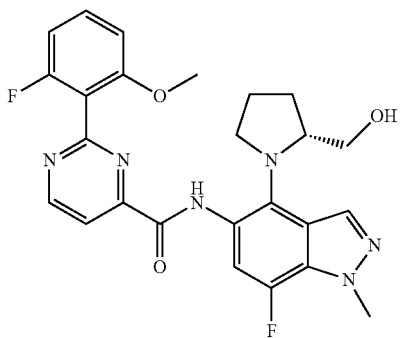

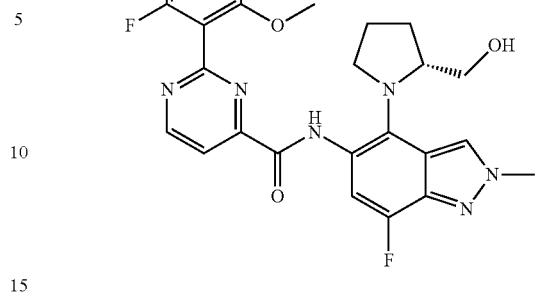

The TFA salts of the title compounds were prepared according to the procedures described in Example 1, using (R)-pyrrolidin-2-ylmethanol instead of tert-butyl (1S,4S)-2,5-diazabicyclo[2.2.1]heptane-2-carboxylate as starting material. Peak 1: LCMS calculated for $C_{25}H_{25}F_2N_6O_3(M+H)^+$: m/z=495.2; Found: 495.2. Peak 2: LCMS calculated for $C_{25}H_{25}F_2N_6O_3$ $(M+H)^+$: m/z=495.2; Found: 495.2.

Example 7. N-(7-Fluoro-1-methyl-4-morpholino-1H-indazol-5-yl)-2-(2-fluoro-6-methoxyphenyl)pyrimidine-4-carboxamide and N-(7-fluoro-2-methyl-4-morpholino-2H-indazol-5-yl)-2-(2-fluoro-6-methoxyphenyl)pyrimidine-4-carboxamide

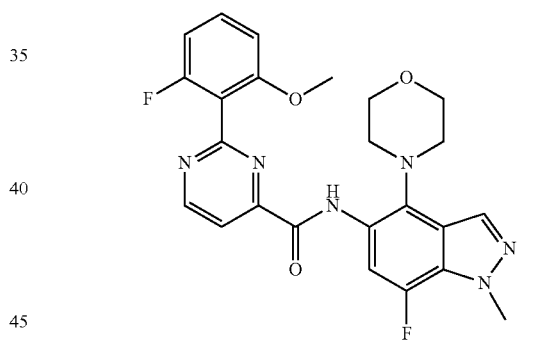

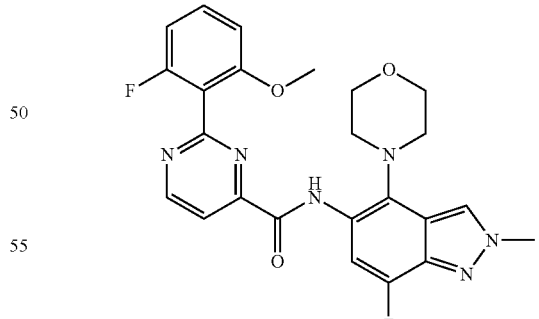

The TFA salts of the title compounds were prepared according to the procedures described in Example 1, using morpholine instead of tert-butyl (1S,4S)-2,5-diazabicyclo[2.2.1]heptane-2-carboxylate as starting material. Peak 1: LCMS calculated for $C_{24}H_{23}F_2N_6O_3(M+H)^+$: m/z=481.2; Found: 481.2. Peak 2: LCMS calculated for $C_{24}H_{23}F_2N_6O_3$ $(M+H)^+$: m/z=481.2; Found: 481.2.

Example 8. N-(7-Fluoro-1-methyl-4-(6-oxo-2,7-diazaspiro[4.4]nonan-2-yl)-1H-indazol-5-yl)-2-(2-fluoro-6-methoxyphenyl)pyrimidine-4-carboxamide and N-(7-fluoro-2-methyl-4-(6-oxo-2,7-diazaspiro[4.4]nonan-2-yl)-2H-indazol-5-yl)-2-(2-fluoro-6-methoxyphenyl)pyrimidine-4-carboxamide

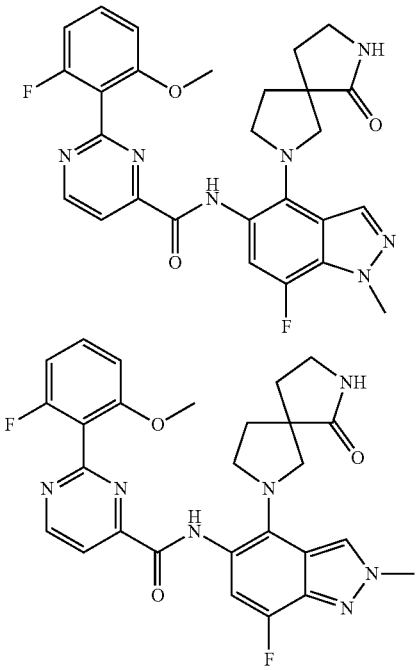

The TFA salts of the title compounds were prepared according to the procedures described in Example 1, using 2,7-diazaspiro[4.4]nonan-1-one instead of tert-butyl (1S,4S)-2,5-diazabicyclo[2.2.1]heptane-2-carboxylate as starting material. Peak 1: LCMS calculated for $C_{27}H_{26}F_2N_7O_3$ $(M+H)^+$: m/z=534.2; Found: 534.2. Peak 2: LCMS calculated for $C_{27}H_{26}F_2N_7O_3$ $(M+H)^+$: m/z=534.2; Found: 534.2.

Example 9. N-(4-(3-Aminoazetidin-1-yl)-7-fluoro-1-methyl-1H-indazol-5-yl)-2-(2-fluoro-6-methoxyphenyl)pyrimidine-4-carboxamide

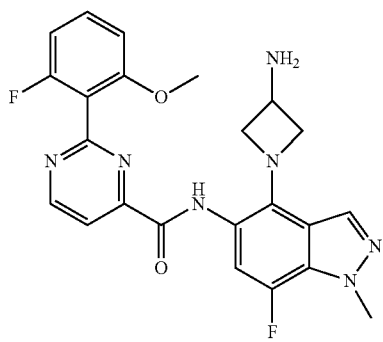 [SMILES: COc1cccc(F)c1-c1nccc(C(=O)Nc2cc(F)c3c(cnn3C)c2N2CC(N)C2)n1]

The TFA salt of the title compound was prepared according to the procedures described in Example 1, using tert-butyl azetidin-3-ylcarbamate instead of tert-butyl (1S,4S)-2,5-diazabicyclo[2.2.1]heptane-2-carboxylate as starting material. LCMS calculated for $C_{23}H_{22}F_2N_7O_2(M+H)^+$: m/z=466.2; Found: 466.2.

Example 10. (R)—N-(4-(2-(Aminomethyl)pyrrolidin-1-yl)-7-fluoro-1-methyl-1H-indazol-5-yl)-2-(2-fluoro-6-methoxyphenyl)pyrimidine-4-carboxamide and (R)—N-(4-(2-(Aminomethyl)pyrrolidin-1-yl)-7-fluoro-2-methyl-2H-indazol-5-yl)-2-(2-fluoro-6-methoxyphenyl)pyrimidine-4-carboxamide

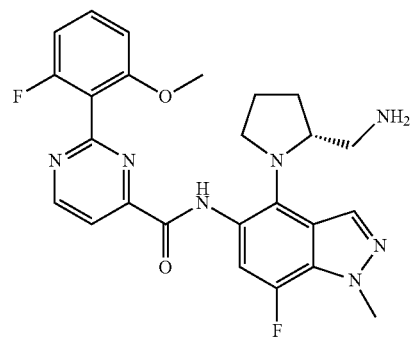

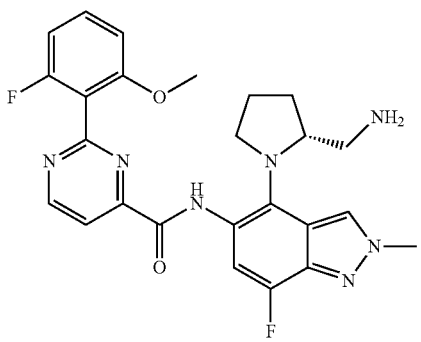

The TFA salts of the title compounds were prepared according to the procedures described in Example 1, using (R)-tert-butyl pyrrolidin-2-ylmethylcarbamate instead of tert-butyl (1S,4S)-2,5-diazabicyclo[2.2.1]heptane-2-carboxylate as starting material. Peak 1: LCMS calculated for $C_{25}H_{26}F_2N_7O_2(M+H)^+$: m/z=494.2; Found: 494.2. Peak 2: LCMS calculated for $C_{25}H_{26}F_2N_7O_2(M+H)^+$: m/z=494.2; Found: 494.2.

Example 11. N-(7-Fluoro-1-methyl-4-(pyrrolidin-3-yl)-1H-indazol-5-yl)-2-(2-fluoro-6-methoxyphenyl)pyrimidine-4-carboxamide

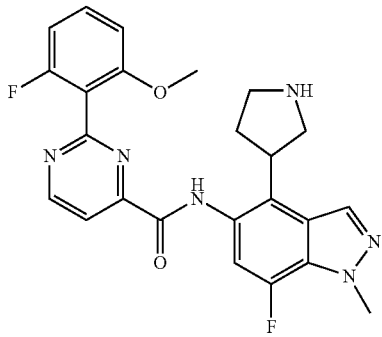 [SMILES: COc1cccc(F)c1-c1nccc(C(=O)Nc2cc(F)c3c(cnn3C)c2C2CCNC2)n1]

Step 1. tert-Butyl 3-(5-amino-7-fluoro-1-methyl-1H-indazol-4-yl)pyrrolidine-1-carboxylate

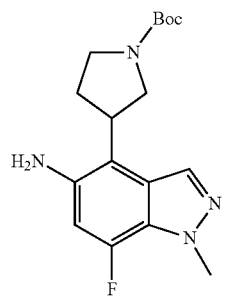 [SMILES: Cn1ncc2c(C3CCN(C(=O)OC(C)(C)C)C3)c(N)cc(F)c21]

A mixture of 4-bromo-7-fluoro-1-methyl-5-nitro-1H-indazole and 4-bromo-7-fluoro-2-methyl-5-nitro-2H-indazole (from Example 1, Step 2; 200 mg, 0.730 mmol), tert-butyl 3-(4,4,5,5-tetramethyl-1,3,2-dioxaborolan-2-yl)-2,5-dihydro-1H-pyrrole-1-carboxylate (323 mg, 1.095 mmol), XPhos Pd G2 (57.4 mg, 0.073 mmol) and potassium phosphate, tribasic (310 mg, 1.460 mmol) was taken up in 1,4-dioxane (2 mL) and water (405 μL). The reaction mixture was stirred at 80° C. for 1 h under a nitrogen atmosphere. The mixture was then cooled to room temperature, diluted with dichloromethane and filtered through a pad of Celite. The filtrate was concentrated, and the residue purified by Biotage Isolera™ (flash purification system with ethyl acetate/hexane at a ratio from 0 to 100%) to afford the desired product.

The residue was dissolved in a 1:1 (v/v) mixture of ethanol/methanol (4 mL) and treated with palladium hydroxide on carbon (102 mg, 0.146 mmol). The reaction flask was evacuated, back filled with hydrogen gas from a balloon and then stirred at 60° C. overnight. The reaction mixture was diluted with methanol, filtered through a pad of Celite, diluted further with ethyl acetate and then concentrated. The crude product was used in the next step without further purification. LCMS calculated for $C_{17}H_{24}FN_4O_2$ (M+H)$^+$: m/z=335.2; Found: 335.2.

Step 2. N-(7-fluoro-1-methyl-4-(pyrrolidin-3-yl)-1H-indazol-5-yl)-2-(2-fluoro-6-methoxyphenyl)pyrimidine-4-carboxamide A mixture of 2-(2-fluoro-6-methoxyphenyl)pyrimidine-4-carboxylic acid (65.3 mg, 0.263 mmol), tert-butyl 3-(5-amino-7-fluoro-1-methyl-1H-indazol-4-yl)pyrrolidine-1-carboxylate (80 mg, 0.239 mmol) and HATU (109 mg, 0.287 mmol) was treated with DMF (1196 μL) and Hunig's base (125 μL, 0.718 mmol). The reaction mixture was stirred at room temperature for 30 min and then treated with water. The resulting precipitate was collected by filtration, washed with water and hexane, and air dried. The solid was dissolved in TFA (1 mL) and allowed to stand for 30 mins at room temperature. The TFA solution was diluted with MeOH and the sample was purified with prep-LCMS (XBridge C18 column, eluting with a gradient of acetonitrile/water containing 0.1% TFA, at flow rate of 60 mL/min) to provide the TFA salt of the title compound. LCMS calculated for $C_{24}H_{23}F_2N_6O_2$ (M+H)$^+$: m/z=465.2; Found: 465.2.

Example 12. N-(7-Fluoro-1-methyl-4-(2-oxopyrrolidin-1-yl)-1H-indazol-5-yl)-2-(2-fluoro-6-methoxyphenyl)pyrimidine-4-carboxamide

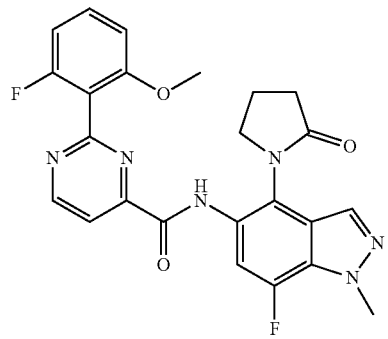 [SMILES: COc1cccc(F)c1-c1nccc(C(=O)Nc2cc(F)c3c(cnn3C)c2N2CCCC2=O)n1]

Step 1. 1-(7 fluoro-bromo-7-methyl-5-nitro-1H-indazol-4 yl) pyrrolidin-2-one

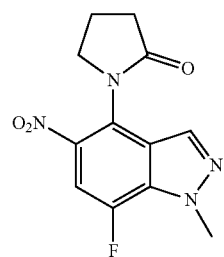 [SMILES: Cn1ncc2c(N3CCCC3=O)c([N+](=O)[O-])cc(F)c21]

A mixture of 4-bromo-7-fluoro-1-methyl-5-nitro-1H-indazole and 4-bromo-7-fluoro-2-methyl-5-nitro-2H-indazole (from Example 1, Step 2; 50 mg, 0.182 mmol), Pd$_2$(dba)$_3$ (16.71 mg, 0.018 mmol), Xantphos (10.56 mg, 0.018 mmol) and cesium carbonate (178 mg, 0.547 mmol) was treated with 1,4-dioxane (912 μL) and pyrrolidin-2-one (28.0 μL, 0.365 mmol). The reaction mixture was stirred at 90° C. overnight under a nitrogen atmosphere. The mixture was then diluted with dichloromethane and filtered through a pad of Celite. The filtrate was concentrated and the residue purified by Biotage Isolera™ (flash purification system with ethyl acetate/hexane at a ratio from 35 to 100%, then methanol/dichloromethane 0-20%) to provide the desired product (50 mg, 100%). LCMS calculated for $C_{12}H_{12}FN_4O_3$ (M+H)⁺: m/z=279.2; Found: 279.2.

Step 2. N-(7-fluoro-1-methyl-4-(2-oxopyrrolidin-1-yl)-1H-indazol-5-yl)-2-(2-fluoro-6-methoxyphenyl)pyrimidine-4-carboxamide A solution of 1-(7-fluoro-1-methyl-5-nitro-1H-indazol-4-yl)pyrrolidin-2-one (48 mg, 0.173 mmol) in a 1:1:1 (v/v/v) mixture of THF/MeOH/Water (1.5 mL) was treated with iron (38.5 mg, 0.690 mmol) and ammonium chloride (55.4 mg, 1.035 mmol). The reaction mixture was heated to 80° C. for 1 h, then cooled to room temperature, diluted with ethyl acetate and filtered through a pad of Celite. The filtrate was washed with water and brine, dried over sodium sulfate and concentrated. The residue was combined with 2-(2-fluoro-6-methoxyphenyl)pyrimidine-4-carboxylic acid (42.8 mg, 0.173 mmol) and HATU (72.2 mg, 0.190 mmol) and then the mixture was treated with DMF (863 μL) and Hunig's base (90 μL, 0.518 mmol). The reaction mixture was stirred at room temperature for 30 min, and then treated with water. The resulting precipitate was collected by filtration, washed with water and hexane, and then dissolved in acetonitrile and purified with prep-LCMS (XBridge C18 column, eluting with a gradient of acetonitrile/water containing 0.1% TFA, at flow rate of 60 mL/min) to provide the TFA salt of the title compound. LCMS calculated for $C_{24}H_{21}F_2N_6O_3$(M+H)⁺: m/z=479.2; Found: 479.2.

Example 13. N-(7-Fluoro-1-methyl-4-(1H-pyrazol-1-yl)-1H-indazol-5-yl)-2-(2-fluoro-6-methoxyphenyl)pyrimidine-4-carboxamide

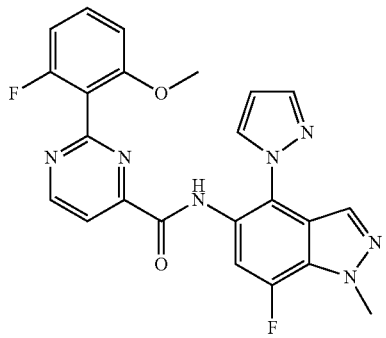 [SMILES: COc1cccc(F)c1-c1nccc(C(=O)Nc2cc(F)c3c(cnn3C)c2-n2cccn2)n1]

Step 1. 7-fluoro-1-methyl-5-nitro-4-(1H-pyrazol-1-yl)-1H-indazole

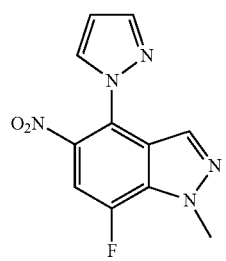 [SMILES: Cn1ncc2c(-n3cccn3)c([N+](=O)[O-])cc(F)c21]

A solution of 1H-pyrazole (12.42 mg, 0.182 mmol) in DMF (1800 μL) was treated with sodium hydride (8.76 mg, 0.219 mmol) and the reaction mixture stirred at room temperature for 5 min. 4-bromo-7-fluoro-1-methyl-5-nitro-1H-indazole (50 mg, 0.182 mmol) was then added and stirring was continued for 3 hrs at room temperature. The mixture was then treated with water and extracted with ethyl acetate. The combined organic phases were washed with water and brine, dried over sodium sulfate and concentrated. The crude product was used in the next step without further purification. LCMS calculated for $C_{11}H_9FN_5O_2$ (M+H)⁺: m/z=262.2; Found: 262.2.

Step 2. N-(7-Fluoro-1-methyl-4-(1H-pyrazol-1-yl)-1H-indazol-5-yl)-2-(2-fluoro-6-methoxyphenyl)pyrimidine-4-carboxamide A solution of 7-fluoro-1-methyl-5-nitro-4-(1H-pyrazol-1-yl)-1H-indazole (45 mg, 0.172 mmol) in a 1:1:1 (v/v/v) mixture of MeOH/THF/Water (1.5 mL) was treated with iron (9.6 mg, 0.172 mmol) and ammonium chloride (9.2 mg, 0.172 mmol). The reaction mixture was heated to 80° C. for 1 h, cooled to room temperature, diluted with ethyl acetate and filtered through a pad of Celite. The filtrate was washed with water and brine, dried over sodium sulfate, and concentrated. To the residue was added 2-(2-fluoro-6-methoxyphenyl)pyrimidine-4-carboxylic acid (42.8 mg, 0.172 mmol) and HATU (65.5 mg, 0.172 mmol) followed by DMF (1700 μL) and Hunig's base (30 μL, 0.172 mmol). The reaction mixture was stirred at room temperature for 30 min, then treated with water. The resulting precipitate was collected by filtration, washed with water and hexane, and then dissolved in acetonitrile/TFA and purified with prep-LCMS (XBridge C18 column, eluting with a gradient of acetonitrile/water containing 0.1% TFA, at flow rate of 60 mL/min) to provide the TFA salt of the title compound. LCMS calculated for $C_{23}H_{18}F_2N_7O_2$ (M+H)⁺: m/z=462.2; Found: 462.2.

Example 14. N-(7-Fluoro-1-methyl-4-o-tolyl-1H-indazol-5-yl)-2-(2-fluoro-6-methoxyphenyl)pyrimidine-4-carboxamide and N-(7-Fluoro-2-methyl-4-o-tolyl-2H-indazol-5-yl)-2-(2-fluoro-6-methoxyphenyl)pyrimidine-4-carboxamide

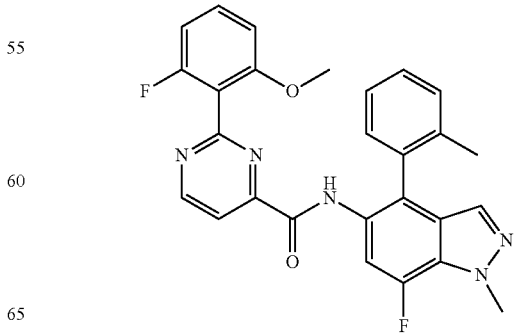

75

-continued

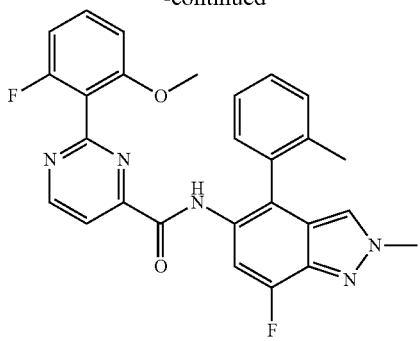

Step 1. A mixture of N-(4-Bromo-7-fluoro-1-methyl-1H-indazol-5-yl)-2-(2-fluoro-6-methoxyphenyl)pyrimidine-4-carboxamide and N-(4-bromo-7-fluoro-2-methyl-2H-indazol-5-yl)-2-(2-fluoro-6-methoxyphenyl)pyrimidine-4-carboxamide

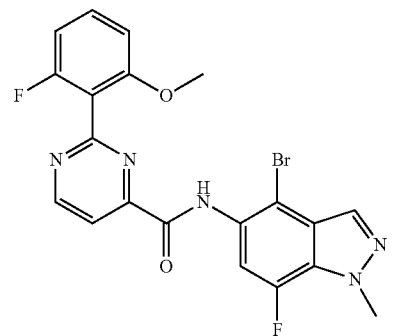

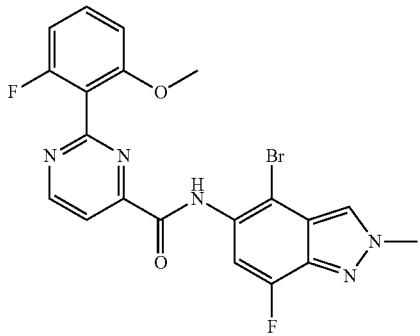

A solution of 4-bromo-7-fluoro-1-methyl-5-nitro-1H-indazole and 4-bromo-7-fluoro-2-methyl-5-nitro-2H-indazole (from Example 1, Step 2; 257 mg, 0.938 mmol) in a 1:1:1 mixture of THF/MeOH/Water (4 mL) was treated with iron (209 mg, 3.75 mmol) and ammonium chloride (301 mg, 5.63 mmol). The reaction mixture was stirred at 80° C. for 1 hr. The mixture was then diluted with ethyl acetate and filtered through a pad of Celite. The filtrate was washed with water and brine, dried over sodium sulfate and filtered. The resulting residue was treated with 2-(2-fluoro-6-methoxyphenyl)pyrimidine-4-carboxylic acid (256 mg, 1.032 mmol), HATU (428 mg, 1.125 mmol), DMF (4689 µL) and Hunig's base (328 µL, 1.876 mmol). The reaction mixture was stirred at room temperature for 30 min. Water was then added and the resulting solid was collected by filtration, washed with water and hexane, and air dried. The crude product was used in the next step without further purification (303 mg, 68%). This compound was isolated as a 1:1 mixture of regioisomers around the indazole. Peak 1: LCMS calculated for $C_{20}H_{15}BrF_2N_5O_2$ (M+H)$^+$: m/z=474.0/476.0; Found: 474.0/476.0. Peak 2: LCMS calculated for $C_{20}H_{15}BrF_2N_5O_2$ (M+H)$^+$: m/z=474.0/476.0; Found: 474.0/476.0.

Step 2: N-(7-Fluoro-1-methyl-4-o-tolyl-1H-indazol-5-yl)-2-(2-fluoro-6-methoxyphenyl)pyrimidine-4-carboxamide and N-(7-Fluoro-2-methyl-4-o-tolyl-2H-indazol-5-yl)-2-(2-fluoro-6-methoxyphenyl)pyrimidine-4-carboxamide A mixture of N-(4-bromo-7-fluoro-1-methyl-1H-indazol-5-yl)-2-(2-fluoro-6-methoxyphenyl)pyrimidine-4-carboxamide and N-(4-bromo-7-fluoro-2-methyl-2H-indazol-5-yl)-2-(2-fluoro-6-methoxyphenyl)pyrimidine-4-carboxamide (15 mg, 0.032 mmol), o-tolylboronic (6 mg, 0.047 mmol), XPhos Pd G2 (2.5 mg, 3.16 µmol) and potassium phosphate, tribasic (13.4 mg, 0.063 mmol) were combined with 1,4-dioxane (253 µL) and water (63.3 µL). The reaction flask was evacuated, back filled with nitrogen, and then stirred at 90° C. for 1 h. The mixture was diluted with acetonitrile, filtered and purified with prep-LCMS (XBridge C18 column, eluting with a gradient of acetonitrile/water containing 0.1% TFA, at flow rate of 60 mL/min) to provide TFA salts of the title compounds. Peak 1: LCMS calculated for $C_{27}H_{22}F_2N_5O_2$ (M+H)$^+$: m/z=486.2; Found: 486.2. Peak 2: LCMS calculated for $C_{27}H_{22}F_2N_5O_2$ (M+H)$^+$: m/z=486.2; Found: 486.2.

Example 15. (R)—N-(4-(3-aminopiperidin-1-yl)-7-cyano-1-methyl-1H-indazol-5-yl)-2-(2-fluoro-6-methoxyphenyl)pyrimidine-4-carboxamide and (R)—N-(4-(3-aminopiperidin-1-yl)-7-cyano-2-methyl-2H-indazol-5-yl)-2-(2-fluoro-6-methoxyphenyl)pyrimidine-4-carboxamide

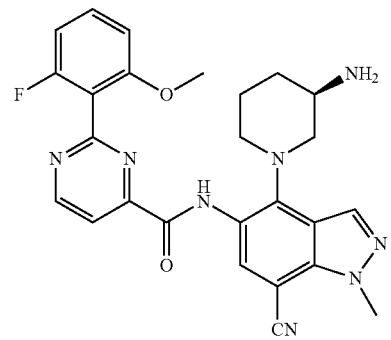

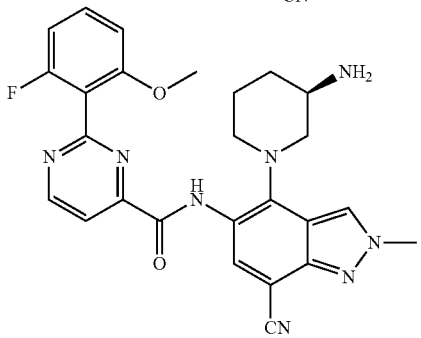

Step 1. (R)-tert-butyl 1-(5-nitro-1H-indazol-4-yl)piperidin-3-ylcarbamate

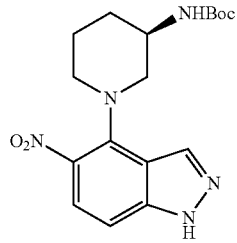 [SMILES: CC(C)(C)OC(=O)N[C@@H]1CCCN(c2c([N+](=O)[O-])ccc3[nH]ncc23)C1]

A solution of 4-bromo-5-nitro-1H-indazole (100 mg, 0.413 mmol) and tert-butyl (R)-piperidin-3-ylcarbamate (124 mg, 0.620 mmol) in DMSO (1377 µL) was treated with Hunig's base (144 µL, 0.826 mmol). The reaction mixture was heated to 90° C. for 2 hrs, then cooled to room temperature, quenched with water and extracted with ethyl acetate. The combined organic phases were washed with water and brine, dried over sodium sulfate and concentrated. The crude product was used in the next step without further purification. LCMS calculated for $C_{17}H_{24}N_5O_4$ $(M+H)^+$: m/z=362.2; Found: 362.2.

Step 2. A mixture of (R)-tert-butyl 1-(7-iodo-1-methyl-5-nitro-1H-indazol-4-yl)piperidin-3-ylcarbamate and (R)-tert-butyl 1-(7-iodo-2-methyl-5-nitro-2H-indazol-4-yl)piperidin-3-ylcarbamate

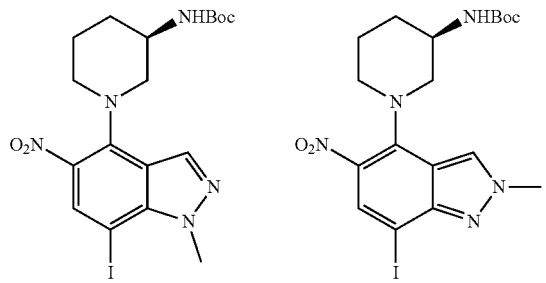 [SMILES: Cn1ncc2c(N3CCC[C@@H](NC(=O)OC(C)(C)C)C3)c([N+](=O)[O-])cc(I)c21 ; Cn1cc2c(N3CCC[C@@H](NC(=O)OC(C)(C)C)C3)c([N+](=O)[O-])cc(I)c2n1]

A solution of tert-butyl (R)-(1-(5-nitro-1H-indazol-4-yl)piperidin-3-yl)carbamate (450 mg, 1.245 mmol) in DMF (6300 µL) was treated with NIS (280 mg, 1.245 mmol) and the reaction mixture was stirred at room temperature for 1 h. Then potassium carbonate (344 mg, 2.5 mmol) and methyl iodide (171 µL, 2.74 mmol) were added and the mixture was heated to 80° C. for 1 h. The reaction mixture was treated with water and extracted with ethyl acetate. The combined organic phases were washed with water and brine, dried over sodium sulfate and concentrated. The residue was purified by Biotage Isolera™ (flash purification system with ethyl acetate/hexane at a ratio from 30 to 100%) to provide the desired product as an orange solid (503 mg, 81%). Peak 1: LCMS calculated for $C_{18}H_{25}IN_5O_4$ $(M+H)^+$: m/z=502.2; Found: 502.2. Peak 2: LCMS calculated for $C_{18}H_{25}IN_5O_4$ $(M+H)^+$: m/z=502.2; Found: 502.2.

Step 3. A mixture of (R)-tert-butyl 1-(5-amino-7-iodo-1-methyl-1H-indazol-4-yl)piperidin-3-ylcarbamate and (R)-tert-butyl 1-(5-amino-7-iodo-2-methyl-2H-indazol-4-yl)piperidin-3-ylcarbamate

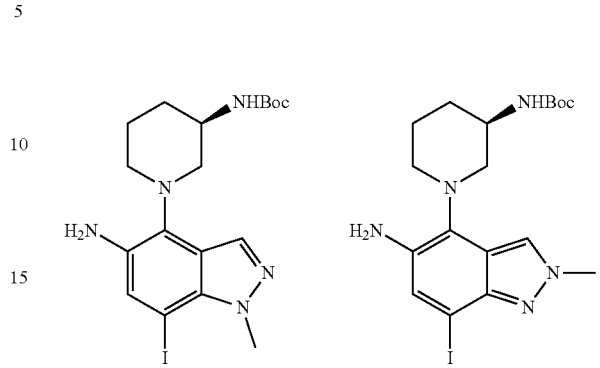

A solution of tert-butyl (R)-(1-(3-iodo-1-methyl-5-nitro-1H-indazol-4-yl)piperidin-3-yl)carbamate and tert-butyl (R)-(1-(3-iodo-2-methyl-5-nitro-2H-indazol-4-yl)piperidin-3-yl)carbamate (475 mg, 0.947 mmol) in a 1:1:1 (v/v/v) mixture of MeOH/THF/Water (4.5 mL) was treated with iron (212 mg, 3.79 mmol) and ammonium chloride (304 mg, 5.68 mmol). The mixture was heated to 65° C. for 2 hrs, diluted with methanol and filtered through a pad of Celite. The filtrate was concentrated, partitioned between ethyl acetate and water and the phases were separated. The organic phase was washed with brine, dried over sodium sulfate and concentrated. The crude product was purified by Biotage Isolera™ (flash purification system with ethyl acetate/hexane at a ratio from 30 to 100%) to provide the desired product as a brown solid (261 mg, 58%). Peak 1: LCMS calculated for $C_{18}H_{27}IN_5O_2(M+H)^+$: m/z=472.2; Found: 472.2. Peak 2: LCMS calculated for $C_{18}H_{27}IN_5O_2$ $(M+H)^+$: m/z=472.2; Found: 472.2.

Step 4. A mixture of (R)-tert-butyl 1-(5-(2-(2-fluoro-6-methoxyphenyl)pyrimidine-4-carboxamido)-7-iodo-1-methyl-1H-indazol-4-yl)piperidin-3-ylcarbamate and (R)-tert-butyl 1-(5-(2-(2-fluoro-6-methoxyphenyl)pyrimidine-4-carboxamido)-7-iodo-2-methyl-2H-indazol-4-yl)piperidin-3-ylcarbamate

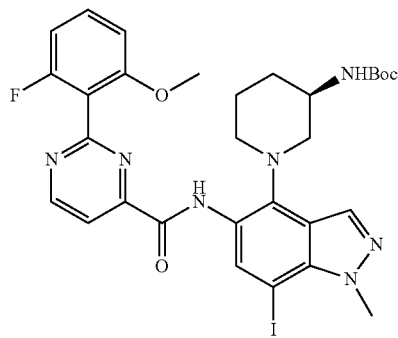

-continued

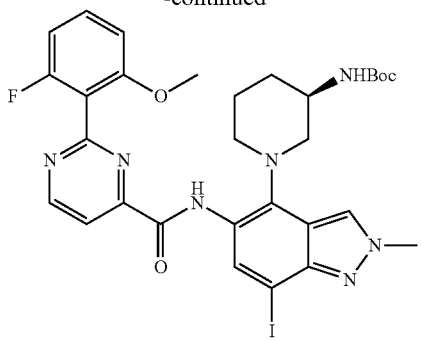

A solution of 2-(2-fluoro-6-methoxyphenyl)pyrimidine-4-carboxylic acid (151 mg, 0.609 mmol), a mixture of tert-butyl (R)-(1-(5-amino-3-iodo-1-methyl-1H-indazol-4-yl)piperidin-3-yl)carbamate and tert-butyl (R)-(1-(5-amino-3-iodo-2-methyl-2H-indazol-4-yl)piperidin-3-yl)carbamate (261 mg, 0.554 mmol) and HATU (253 mg, 0.664 mmol) in DMF (2769 μL) was treated with Hunig's base (193 μL, 1.107 mmol). The reaction mixture was stirred at room temperature for 1 h, then treated with water and extracted with dichloromethane. The combined organic phases were washed with water and brine, dried over sodium sulfate and concentrated. The residue was purified by Biotage Isolera™ (flash purification system with methanol/dichloromethane at a ratio from 2 to 10%) to provide the desired product (250 mg, 64%) as a 1:1 mixture of indazole regioisomers. Peak 1: LCMS calculated for $C_{30}H_{34}FIN_7O_4$ (M+H)$^+$: m/z=702.2; Found: 702.2. Peak 2: LCMS calculated for $C_{30}H_{34}FIN_7O_4$ (M+H)$^+$: m/z=702.2; Found: 702.2.

Step 5: (R)—N-(4-(3-aminopiperidin-1-yl)-7-cyano-1-methyl-1H-indazol-5-yl)-2-(2-fluoro-6-methoxyphenyl)pyrimidine-4-carboxamide and (R)—N-(4-(3-aminopiperidin-1-yl)-7-cyano-2-methyl-2H-indazol-5-yl)-2-(2-fluoro-6-methoxyphenyl)pyrimidine-4-carboxamide A mixture of (R)-tert-butyl 1-(5-(2-(2-fluoro-6-methoxyphenyl)pyrimidine-4-carboxamido)-7-iodo-1-methyl-1H-indazol-4-yl)piperidin-3-ylcarbamate and (R)-tert-butyl 1-(5-(2-(2-fluoro-6-methoxyphenyl)pyrimidine-4-carboxamido)-7-iodo-2-methyl-2H-indazol-4-yl)piperidin-3-ylcarbamate (37 mg, 0.053 mmol), tetrakis(triphenylphosphine)palladium(O) (6.1 mg, 5.27 μmol) and zinc cyanide (12.4 mg, 0.105 mmol) was combined with DMF (264 μL). The reaction flask was evacuated, back filled with nitrogen, then stirred at 100° C. overnight. The mixture was cooled to room temperature, treated with water and extracted with ethyl acetate. The combined organic phases were washed with water and brine, dried over sodium sulfate and concentrated. To the residue was added TFA. After stirring for 30 mins at room temperature, the mixture was diluted with methanol and purified with prep-LCMS (XBridge C18 column, eluting with a gradient of acetonitrile/water containing 0.1% TFA, at flow rate of 60 mL/min) to provide TFA salts of the title compounds. Peak 1: LCMS calculated for $C_{26}H_{26}FN_8O_2$ (M+H)$^+$: m/z=501.2; Found: 501.2. Peak 2: LCMS calculated for $C_{26}H_{26}FN_8O_2$ (M+H)$^+$: m/z=501.2; Found: 501.2.

Example 16. (R)-4-(3-aminopiperidin-1-yl)-5-(2-(2-fluoro-6-methoxyphenyl)pyrimidine-4-carboxamido)-N,1-dimethyl-1H-indazole-7-carboxamide and (R)-4-(3-aminopiperidin-1-yl)-5-(2-(2-fluoro-6-methoxyphenyl)pyrimidine-4-carboxamido)-N,2-dimethyl-2H-indazole-7-carboxamide

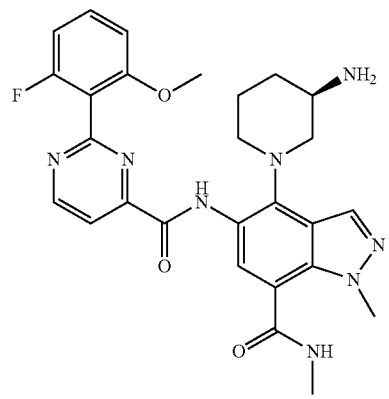

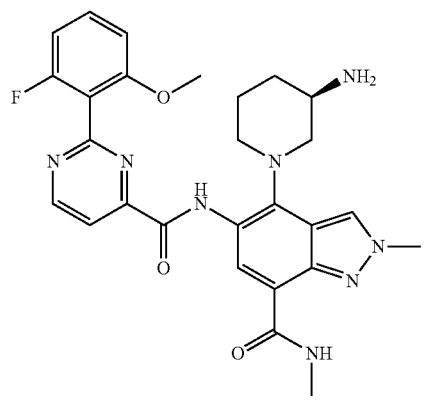

Step 1. A mixture of (R)-4-(3-(tert-butoxycarbonylamino)piperidin-1-yl)-5-(2-(2-fluoro-6-methoxyphenyl)pyrimidine-4-carboxamido)-1-methyl-1H-indazole-7-carboxylic acid and (R)-4-(3-(tert-butoxycarbonylamino)piperidin-1-yl)-5-(2-(2-fluoro-6-methoxyphenyl)pyrimidine-4-carboxamido)-2-methyl-2H-indazole-7-carboxylic acid

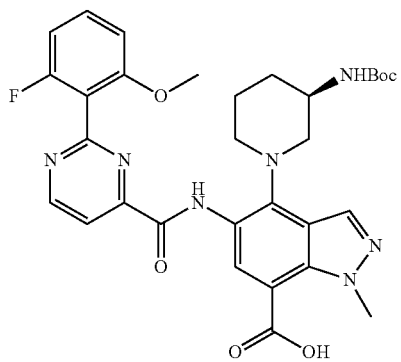

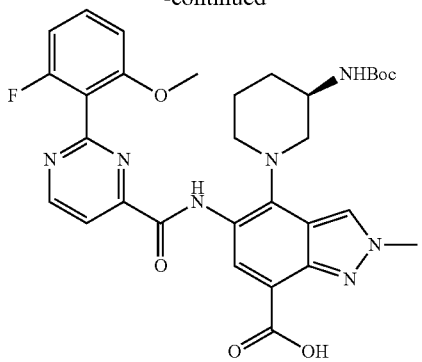

A mixture of (R)-tert-butyl 1-(5-(2-(2-fluoro-6-methoxyphenyl)pyrimidine-4-carboxamido)-7-iodo-1-methyl-1H-indazol-4-yl)piperidin-3-ylcarbamate and (R)-tert-butyl 1-(5-(2-(2-fluoro-6-methoxyphenyl)pyrimidine-4-carboxamido)-7-iodo-2-methyl-2H-indazol-4-yl)piperidin-3-ylcarbamate (Example 15, Step 4; 285 mg, 0.406 mmol), dppf-PdCl$_2$ (33.2 mg, 0.041 mmol) and triethylamine (170 µL, 1.219 mmol) were combined with DMF (2437 µL) and MeOH (1625 µl). The reaction flask was evacuated, back filled with carbon monoxide from a balloon, and then stirred at 80° C. for 2 h. After cooling, water and ethyl acetate were added and the phases were separated. The aqueous phase was extracted with ethyl acetate and the combined organic phases were washed with water and brine, dried over sodium sulfate and concentrated. The residue was purified by Biotage Isolera™ (flash purification system with ethyl acetate/hexane at a ratio from 0 to 100%) to provide the desired product.

To the residue was added a 1:1:1 (v/v/v) mixture of THF/MeOH/Water (1.5 mL) followed by lithium hydroxide (83 mg, 2.031 mmol). The reaction mixture was stirred at room temperature overnight, and then concentrated. The residue was acidified with 1 N HCl, and extracted with ethyl acetate. The combined organic phases were washed with brine, dried over sodium sulfate and concentrated. The crude solid was used in the next step without further purification. LCMS calculated for C$_{31}$H$_{35}$FN$_7$O$_6$(M+H)$^+$: m/z=620.2; Found: 620.2.

Step 2. (R)-4-(3-aminopiperidin-1-yl)-5-(2-(2-fluoro-6-methoxyphenyl)pyrimidine-4-carboxamido)-N,1-dimethyl-1H-indazole-7-carboxamide and (R)-4-(3-aminopiperidin-1-yl)-5-(2-(2-fluoro-6-methoxyphenyl)pyrimidine-4-carboxamido)-N,2-dimethyl-2H-indazole-7-carboxamide A solution of (R)-4-(3-((tert-butoxycarbonyl)amino)piperidin-1-yl)-5-(2-(2-fluoro-6-methoxyphenyl)pyrimidine-4-carboxamido)-1-methyl-1H-indazole-7-carboxylic acid and (R)-4-(3-((tert-butoxycarbonyl)amino)piperidin-1-yl)-5-(2-(2-fluoro-6-methoxyphenyl)pyrimidine-4-carboxamido)-2-methyl-2H-indazole-7-carboxylic acid (15 mg, 0.024 mmol) and HATU (11 mg, 0.029 mmol) in DMF (242 µl) was treated with methanamine (36.3 µL, 0.073 mmol) and Hunig's base (12.7 µL, 0.073 mmol). The reaction mixture was stirred at room temperature for 30 mins, then treated with water and extracted with ethyl acetate. The combined organic phases were washed with brine, dried over sodium sulfate and concentrated. TFA (1 mL) was added to the residue and the reaction mixture was stirred at room temperature for 30 min, diluted with methanol and purified with prep-LCMS (XBridge C18 column, eluting with a gradient of acetonitrile/water containing 0.1% TFA, at flow rate of 60 mL/min) to provide TFA salts of the title compounds. Peak 1: LCMS calculated for C$_{27}$H$_{30}$FN$_8$O$_3$(M+H)$^+$: m/z=533.2; Found: 533.2. Peak 2: LCMS calculated for C$_{27}$H$_{30}$FN$_8$O$_3$(M+H)$^+$: m/z=533.2; Found: 533.2.

Example 17. (R)—N-(4-(3-Aminopyrrolidin-1-yl)-7-fluoro-1-(2-hydroxyethyl)-1H-indazol-5-yl)-2-(2-fluoro-6-methoxyphenyl)pyrimidine-4-carboxamide

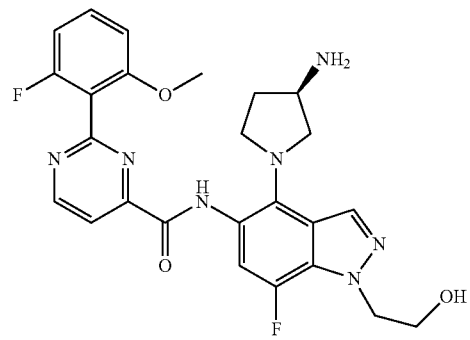 [SMILES: COc1cccc(F)c1-c1nccc(C(=O)Nc2cc(F)c3c(cnn3CCO)c2N2CC[C@@H](N)C2)n1]

Step 1. 4-Bromo-1-(2-(tert-butyldimethylsilyloxy)ethyl)-7-fluoro-5-nitro-1H-indazole

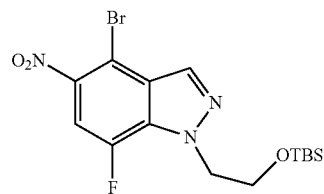 [SMILES: CC(C)(C)[Si](C)(C)OCCn1ncc2c(Br)c([N+](=O)[O-])cc(F)c21]

A solution of 4-bromo-7-fluoro-5-nitro-1H-indazole (from Example 1, Step 1; 375 mg, 1.44 mmol) in DMF (7200 µL) was treated with potassium carbonate (399 mg, 2.88 mmol) and (2-bromoethoxy)(tert-butyl)dimethylsilane (308 µl, 1.442 mmol). The reaction mixture was heated to 90° C. for 2 h. The mixture was then cooled to room temperature, treated with water and extracted with ethyl acetate. The combined organic phases were washed with water and brine, dried over sodium sulfate and concentrated. The residue was purified by Biotage Isolera™ (flash purification system with ethyl acetate/hexane at a ratio from 0 to 50%) to provide the desired product as a yellow solid (151 mg, 25%). LCMS calculated for C$_{15}$H$_{22}$BrFN$_3$O$_3$Si (M+H)$^+$: m/z=418.0/420.0; Found: 418.0/420.0.

Step 2. (R)-tert-butyl 1-(5-amino-1-(2-(tert-butyldimethylsilyloxy)ethyl)-7-fluoro-1H-indazol-4-yl)pyrrolidin-3-ylcarbamate

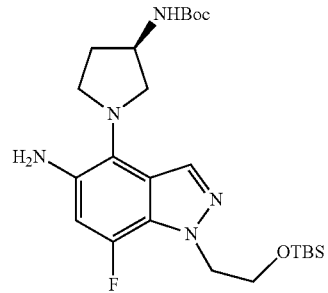 [SMILES: CC(C)(C)OC(=O)N[C@@H]1CCN(c2c(N)cc(F)c3c2cnn3CCO[Si](C)(C)C(C)(C)C)C1]

A mixture of 4-bromo-1-(2-((tert-butyldimethylsilyl)oxy)ethyl)-7-fluoro-5-nitro-1H-indazole (50 mg, 0.120 mmol), tert-butyl (R)-pyrrolidin-3-ylcarbamate (33.4 mg, 0.179 mmol), Ruphos Pd G2 (9.28 mg, 0.012 mmol) and cesium carbonate (78 mg, 0.239 mmol) was combined with 1,4-dioxane (400 µL) and the reaction flask was evacuated, back filled with nitrogen, then stirred at 60° C. for 1 h. The mixture was diluted with dichloromethane, filtered through a pad of Celite and concentrated.

The intermediate residue was dissolved in a 1:1:1 (v/v/v) mixture of MeOH/THF/water and treated with iron (26.7 mg, 0.478 mmol) and ammonium chloride (38.4 mg, 0.717 mmol). The reaction mixture was stirred at 80° C. for 1 h, diluted with ethyl acetate and filtered through a pad of Celite. The filtrate was washed with water and brine, dried over sodium sulfate and concentrated. The crude product was used in the next step without further purification. LCMS calculated for $C_{24}H_{41}FN_5O_3Si$ (M+H)$^+$: m/z=494.2; Found: 494.2.

Step 3. (R)—N-(4-(3-aminopyrrolidin-1-yl)-7-fluoro-1-(2-hydroxyethyl)-1H-indazol-5-yl)-2-(2-fluoro-6-methoxyphenyl)pyrimidine-4-carboxamide A mixture of 2-(2-fluoro-6-methoxyphenyl)pyrimidine-4-carboxylic acid (32.7 mg, 0.132 mmol), tert-butyl (R)-(1-(5-amino-1-(2-((tert-butyldimethylsilyl)oxy)ethyl)-7-fluoro-1H-indazol-4-yl)pyrrolidin-3-yl)carbamate (65 mg, 0.132 mmol) and HATU (60.1 mg, 0.158 mmol) in DMF (1317 µl) was treated with Hunig's base (46.0 µl, 0.263 mmol). The reaction mixture was stirred at room temperature for 30 min, treated with water and filtered. The resultant precipitate was washed with water and hexane, and air dried. The solid was then dissolved in a 1:1 mixture of MeOH/4N solution of HCl in dioxane (1 mL), stirred at room temperature for 30 min, and then diluted with methanol and purified with prep-LCMS (XBridge C18 column, eluting with a gradient of acetonitrile/water containing 0.1% TFA, at flow rate of 60 mL/min) to provide the TFA salt of the title compound. LCMS calculated for $C_{25}H_{26}F_2N_7O_3$(M+H)$^+$: m/z=510.2; Found: 510.2.

Example 18. N-(1,7-Dimethyl-4-(piperazin-1-yl)-1H-indazol-5-yl)-2-(2-fluoro-6-methoxyphenyl)pyrimidine-4-carboxamide and N-(2,7-dimethyl-4-(piperazin-1-yl)-2H-indazol-5-yl)-2-(2-fluoro-6-methoxyphenyl)pyrimidine-4-carboxamide

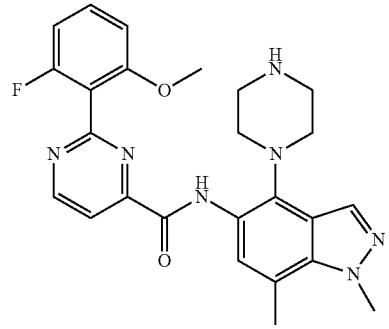

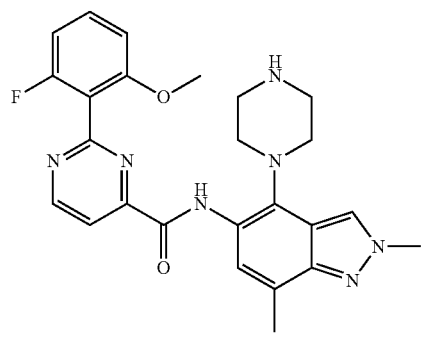

Step 1. tert-butyl 4-(5-nitro-1H-indazol-4-yl)piperazine-1-carboxylate

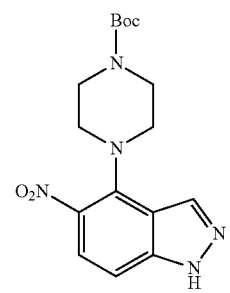 [SMILES: CC(C)(C)OC(=O)N1CCN(c2c([N+](=O)[O-])ccc3[nH]ncc23)CC1]

This compound was prepared in an analogous fashion to Example 15, Step 1, using N-Boc piperidine instead of (R)-3H-amino piperidine as the coupling partner. LCMS calculated for $C_{16}H_{22}N_5O_4$ (M+H)$^+$: m/z=348.2; Found: 348.2.

Step 2. A mixture of tert-butyl 4-(7-iodo-1-methyl-5-nitro-1H-indazol-4-yl)piperazine-1-carboxylate and tert-butyl 4-(7-iodo-2-methyl-5-nitro-2H-indazol-4-yl)piperazine-1-carboxylate

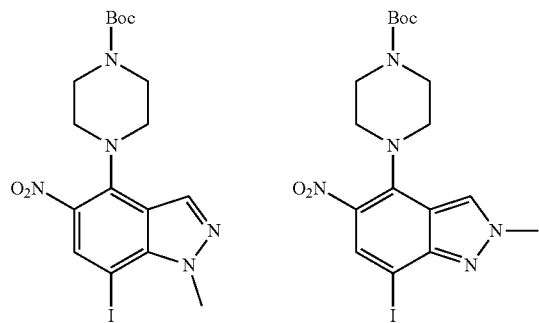 [SMILES: Cn1ncc2c(N3CCN(C(=O)OC(C)(C)C)CC3)c([N+](=O)[O-])cc(I)c21 ; Cn1cc2c(N3CCN(C(=O)OC(C)(C)C)CC3)c([N+](=O)[O-])cc(I)c2n1]

A solution of tert-butyl 4-(5-nitro-1H-indazol-4-yl)piperazine-1-carboxylate (373 mg, 1.074 mmol) in DMF (3579 μL) was treated with NIS (242 mg, 1.074 mmol) and the reaction mixture was stirred at room temperature overnight. Then, potassium carbonate (297 mg, 2.148 mmol) and methyl iodide (101 μL, 1.611 mmol) were added and the reaction mixture was heated to 80° C. for 1 h. The reaction mixture was then cooled to room temperature, treated with water, and then extracted with ethyl acetate. The combined organic phases were washed with water and brine, dried over sodium sulfate, and concentrated. The crude product was then purified by Biotage Isolera™ (flash purification system with ethyl acetate/hexane at a ratio from 0 to 100%) to provide the desired product (358 mg, 68%). Peak 1: LCMS calculated for $C_{17}H_{23}IN_5O_4$ (M+H)$^+$: m/z=488.2; Found: 488.2. Peak 2: LCMS calculated for $C_{17}H_{23}IN_5O_4$ (M+H)$^+$: m/z=488.2; Found: 488.2.

Step 3. A Mixture of tert-butyl 4-(5-(2-(2-fluoro-6-methoxyphenyl)pyrimidine-4-carboxamido)-7-iodo-1-methyl-1H-indazol-4-yl)piperazine-1-carboxylate and tert-butyl 4-(5-(2-(2-fluoro-6-methoxyphenyl)pyrimidine-4-carboxamido)-7-iodo-2-methyl-2H-indazol-4-yl)piperazine-1-carboxylate

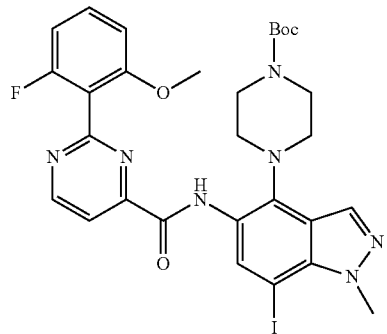

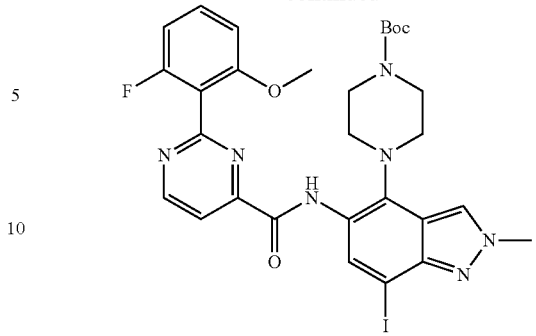

A solution of tert-butyl 4-(7-iodo-1-methyl-5-nitro-1H-indazol-4-yl)piperazine-1-carboxylate and tert-butyl 4-(7-iodo-2-methyl-5-nitro-2H-indazol-4-yl)piperazine-1-carboxylate (358 mg, 0.735 mmol) in a 1:1:1 (v/v/v) mixture of Water/THF/MeOH (3 mL) were treated with iron (164 mg, 2.94 mmol) and ammonium chloride (236 mg, 4.41 mmol). The mixture was heated to 80° C. for 1 h, then diluted with ethyl acetate and filtered through a pad of Celite. The filtrate was partitioned between ethyl acetate and water and the phases were separated. The organic phase was washed with water and brine, dried over sodium sulfate and concentrated.

The resultant residue was combined with 2-(2-fluoro-6-methoxyphenyl)pyrimidine-4-carboxylic acid (201 mg, 0.808 mmol), HATU (335 mg, 0.882 mmol) and DMF (3 mL), and treated with Hunig's base (385 μL, 2.2 mmol). After stirring at room temperature for 30 min, water was added and the resulting precipitate was collected by filtration, washed with water and hexane, and then air dried overnight. The crude solid was used in the next step without further purification. Peak 1: LCMS calculated for $C_{29}H_{32}FIN_7O_4$(M+H)$^+$: m/z=688.2; Found: 688.2. Peak 2: LCMS calculated for $C_{29}H_{32}FIN_7O_4$(M+H)$^+$: m/z=688.2; Found: 688.2.

Step 4. N-(1,7-dimethyl-4-(piperazin-1-yl)-1H-indazol-5-yl)-2-(2-fluoro-6-methoxyphenyl)pyrimidine-4-carboxamide and N-(2,7-dimethyl-4-(piperazin-1-yl)-2H-indazol-5-yl)-2-(2-fluoro-6-methoxyphenyl)pyrimidine-4-carboxamide A mixture of tert-butyl 4-(5-(2-(2-fluoro-6-methoxyphenyl)pyrimidine-4-carboxamido)-7-iodo-1-methyl-1H-indazol-4-yl)piperazine-1-carboxylate and tert-butyl 4-(5-(2-(2-fluoro-6-methoxyphenyl)pyrimidine-4-carboxamido)-7-iodo-2-methyl-2H-indazol-4-yl)piperazine-1-carboxylate (200 mg, 0.291 mmol), trimethylboroxine (81 μL, 0.582 mmol), dppf-PdCl$_2$ (23.76 mg, 0.029 mmol) and potassium phosphate, tribasic (123 mg, 0.582 mmol) were combined with 1,4-dioxane (2300 μL) and water (582 μL). The reaction flask was evacuated, back filled with nitrogen, and stirred at 80° C. overnight. The mixture was diluted with dichloromethane and filtered through a pad of Celite. The filtrate was concentrated, dissolved in TFA and stirred at room temperature for 30 min. The mixture was added dropwise to a solution of saturated aqueous sodium bicarbonate. After bubbling subsided, the mixture was extracted with dichloromethane. The combined organic phases were washed with saturated aqueous sodium bicarbonate and brine, dried over sodium sulfate, and concentrated. The residue was dissolved in methanol and purified with prep-LCMS (XBridge C18 column, eluting with a gradient of acetonitrile/water containing 0.1% TFA, at flow rate of 60 mL/min) to provide TFA salts of the title compounds. Peak 1: LCMS calculated for $C_{25}H_{27}FN_7O_2(M+H)^+$: m/z=476.2; Found: 476.2. Peak 2: LCMS calculated for $C_{25}H_{27}FN_7O_2$ $(M+H)^+$: m/z=476.2; Found: 476.2.

Example 19. (R)—N-(4-(3-aminopyrrolidin-1-yl)-1,7-dimethyl-1H-indazol-5-yl)-2-(2-fluoro-6-methoxyphenyl)pyrimidine-4-carboxamide

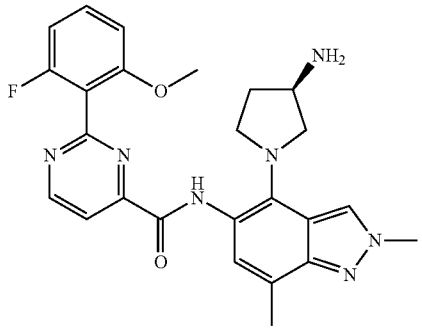 [SMILES: COc1cccc(F)c1-c1nccc(C(=O)Nc2cc(C)c3nn(C)cc3c2N2CC[C@@H](N)C2)n1]

The TFA salt of the title compound was prepared according to the procedures described in Example 18 (and detailed below), using (R)-tert-butyl pyrrolidin-3-ylcarbamate instead of N-Boc piperidine as starting material.

Step 1. tert-Butyl (R)-(1-(7-iodo-2-methyl-5-nitro-2H-indazol-4-yl)pyrrolidin-3-yl)carbamate

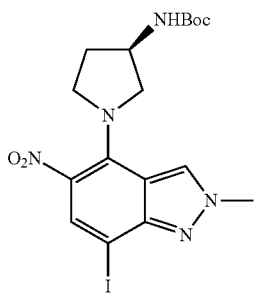 [SMILES: Cn1cc2c(N3CC[C@@H](NC(=O)OC(C)(C)C)C3)c([N+](=O)[O-])cc(I)c2n1]

A solution of 4-bromo-5-nitro-1H-indazole (1.0 g, 4.13 mmol) and tert-butyl (R)-pyrrolidin-3-ylcarbamate (0.770 g, 4.13 mmol) in DMSO (13.77 ml) was treated with Hunig's base (1.443 mL, 8.26 mmol) and the reaction mixture was heated to 90° C. for 1 hr. The reaction mixture was cooled, treated with water and extracted with ethyl acetate. The organic phase was washed with water and brine, dried over sodium sulfate and concentrated. The crude product was dissolved in DMF (12 mL) and NIS (0.930 g, 4.13 mmol) was added. The reaction mixture was stirred at r.t. overnight, then quenched with water and extracted with ethyl acetate. The organic phase was washed with water and brine, dried over sodium sulfate and concentrated. The crude product was dissolved in DMF (25 mL) and treated with potassium carbonate (0.857 g, 6.20 mmol) and methyl iodide (0.310 mL, 4.96 mmol). The reaction mixture was heated to 70° C. for 3 hr, then treated with water and extracted with ethyl acetate. The organic phase was washed with water and brine, dried over sodium sulfate and concentrated. The crude product was purified by Biotage Isolera™ (20-100% ethyl acetate in hexanes) to provide the desired 2H isomer as a red solid (840 mg, 42%). LCMS calculated for $C_{17}H_{23}IN_5O_4$ $(M+H)^+$: m/z=488.2; Found: 488.2.

Step 2. tert-Butyl (R)-(1-(2,7-dimethyl-5-nitro-2H-indazol-4-yl)pyrrolidin-3-yl)carbamate

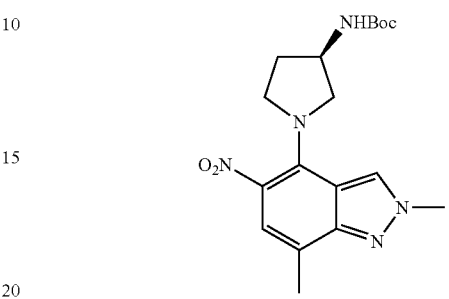

A mixture of tert-butyl (R)-(1-(7-iodo-2-methyl-5-nitro-2H-indazol-4-yl)pyrrolidin-3-yl)carbamate (839 mg, 1.72 mmol), DPPF-PdCl$_2$ (141 mg, 0.172 mmol), potassium carbonate (476 mg, 3.44 mmol) and trimethylboroxine (361 μl, 2.58 mmol) in 1,4-dioxane (5 ml) and water (1 ml) was degassed by evacuation and back filling with nitrogen. The mixture was heated to 100° C. overnight. The mixture was diluted with DCM and filtered through a plug of Celite. The filtrate was concentrated and the residue purified by Biotage Isolera™ (40-100% ethyl acetate in hexanes) to provide the desired product as a red solid (384 mg, 59%). LCMS calculated for $C_{18}H_{26}N_5O_4$ $(M+H)^+$: m/z=376.2; Found: 376.2.

Step 3. tert-Butyl (R)-(1-(5-(2-(2-fluoro-6-methoxyphenyl)pyrimidine-4-carboxamido)-2,7-dimethyl-2H-indazol-4-yl)pyrrolidin-3-yl)carbamate

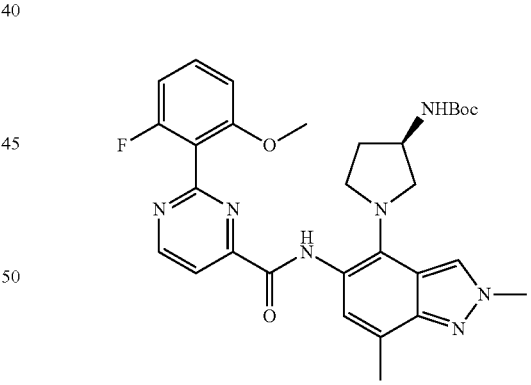

A solution of tert-butyl (R)-(1-(2,7-dimethyl-5-nitro-2H-indazol-4-yl)pyrrolidin-3-yl)carbamate (384 mg, 1.023 mmol) in a 1:1:1 mixture of THF/MeOH/water (6 mL) was treated with iron (228 mg, 4.09 mmol) and ammonium chloride (328 mg, 6.14 mmol). The reaction mixture was heated to 60° C. for 1 hr, then diluted with ethyl acetate and filtered through a plug of Celite. The filtrate was washed with water and brine, dried over sodium sulfate and concentrated. The crude product was dissolved in DMF (5114 μl) and 2-(2-fluoro-6-methoxyphenyl)pyrimidine-4-carboxylic acid (254 mg, 1.023 mmol) (from Example 1, Step 3), HATU (428 mg, 1.125 mmol) and Hunig's base (357 μL, 2.05 mmol) were added. The reaction mixture was stirred at r.t. for 30 mins, then quenched with water and extracted with ethyl acetate. The organic phase was washed with water and brine, dried over sodium sulfate and concentrated. The crude product was purified by Biotage Isolera™ (50-100% ethyl acetate in hexanes) to provide the desired product (416 mg, 71%). LCMS calculated for $C_{30}H_{35}FN_7O_4(M+H)^+$: m/z=576.2; Found: 576.2.

Step 4. (R)—N-(4-(3-Aminopyrrolidin-1-yl)-1,7-dimethyl-2H-indazol-5-yl)-2-(2-fluoro-6-methoxyphenyl)pyrimidine-4-carboxamide Tert-butyl (R)-(1-(5-(2-(2-fluoro-6-methoxyphenyl)pyrimidine-4-carboxamido)-2,7-dimethyl-2H-indazol-4-yl)pyrrolidin-3-yl)carbamate (416 mg, 1.02 mmol) was treated with TFA (3 mL) and the reaction mixture was stirred at r.t. for 30 mins. The reaction mixture was diluted with methanol and purified with prep-LCMS (XBridge C18 column, eluting with a gradient of acetonitrile/water containing 0.1% TFA, at flow rate of 60 mL/min) to provide TFA salt of the title compound. LCMS calculated for $C_{25}H_{27}FN_7O_2(M+H)^+$: m/z=476.2; Found: 476.2. $^1$H NMR (500 MHz, DMSO) δ 10.79 (s, 1H), 9.26 (d, J=5.0 Hz, 1H), 8.50 (s, 1H), 8.13 (d, J=5.0 Hz, 1H), 8.04 (s, 2H), 7.86 (s, 1H), 7.57 (q, J=8.3 Hz, 1H), 7.08 (d, J=8.4 Hz, 1H), 7.02 (t, J=8.7 Hz, 1H), 4.18 (s, 3H), 3.79 (s, 4H), 3.64 (s, 1H), 3.58-3.54 (m, 1H), 3.51 (q, J=8.3 Hz, 1H), 3.20 (ddd, J=18.0, 9.1, 5.2 Hz, 2H), 2.49 (s, 3H), 2.13-2.01 (m, 1H), 1.90 (ddt, J=11.3, 6.9, 3.4 Hz, 1H).

Example 20. N-(7-Fluoro-1-methyl-4-(pyridin-3-yl)-1H-indazol-5-yl)-2-(2-fluoro-6-methoxyphenyl)pyrimidine-4-carboxamide

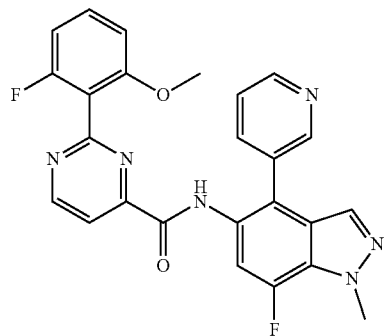 [SMILES: COc1cccc(F)c1-c1nccc(C(=O)Nc2cc(F)c3c(cnn3C)c2-c2cccnc2)n1]

The TFA salt of the title compound was prepared according to the procedures described in Example 14, using pyridin-3-ylboronic acid instead of o-tolylboronic acid as starting material. LCMS calculated for $C_{25}H_{19}F_2N_6O_2(M+H)^+$: m/z=473.2; Found: 473.2.

Example 21. N-(7-Fluoro-1-methyl-4-(1-methyl-1H-pyrazol-4-yl)-1H-indazol-5-yl)-2-(2-fluoro-6-methoxyphenyl)pyrimidine-4-carboxamide

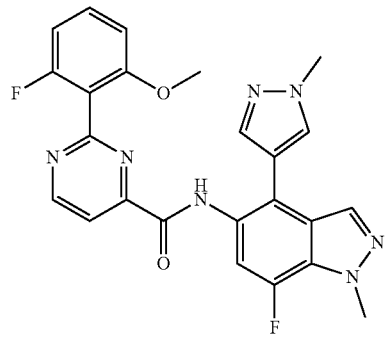 [SMILES: COc1cccc(F)c1-c1nccc(C(=O)Nc2cc(F)c3c(cnn3C)c2-c2cnn(C)c2)n1]

The TFA salt of the title compound was prepared according to the procedures described in Example 14, using 1-methyl-4-(4,4,5,5-tetramethyl-1,3,2-dioxaborolan-2-yl)-1H-pyrazole instead of o-tolylboronic acid as starting material. LCMS calculated for $C_{24}H_{20}F_2N_7O_2$ $(M+H)^+$: m/z=476.2; Found: 476.2.

Example 22. N-(7-Fluoro-4-(3-(hydroxymethyl)phenyl)-1-methyl-1H-indazol-5-yl)-2-(2-fluoro-6-methoxyphenyl)pyrimidine-4-carboxamide

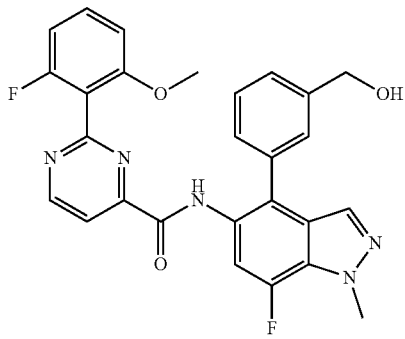 [SMILES: COc1cccc(F)c1-c1nccc(C(=O)Nc2cc(F)c3c(cnn3C)c2-c2cccc(CO)c2)n1]

The TFA salt of the title compound was prepared according to the procedures described in Example 14, using 3-(hydroxymethyl)phenylboronic acid instead of o-tolylboronic acid as starting material. LCMS calculated for $C_{27}H_{22}F_2N_5O_3$ $(M+H)^+$: m/z=502.2; Found: 502.2.

Example 23. N-(7-Fluoro-4-(2-(hydroxymethyl)phenyl)-1-methyl-1H-indazol-5-yl)-2-(2-fluoro-6-methoxyphenyl)pyrimidine-4-carboxamide

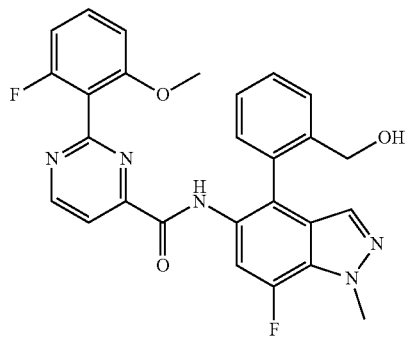 [SMILES: COc1cccc(F)c1-c1nccc(C(=O)Nc2cc(F)c3c(cnn3C)c2-c2ccccc2CO)n1]

The TFA salt of the title compound was prepared according to the procedures described in Example 14, using 2-(hydroxymethyl)phenylboronic acid instead of o-tolylboronic acid as starting material. LCMS calculated for $C_{27}H_{22}F_2N_5O_3$ (M+H)$^+$: m/z=502.2; Found: 502.2.

Example 24. N-(4-(3-((Dimethylamino)methyl)phenyl)-7-fluoro-1-methyl-1H-indazol-5-yl)-2-(2-fluoro-6-methoxyphenyl)pyrimidine-4-carboxamide

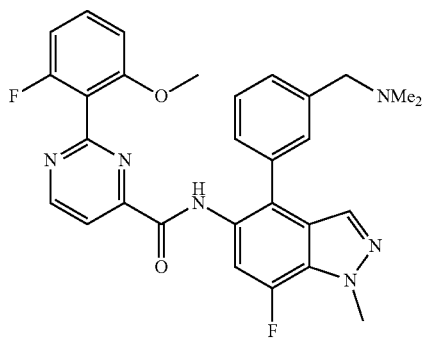 [SMILES: COc1cccc(F)c1-c1nccc(C(=O)Nc2cc(F)c3c(cnn3C)c2-c2cccc(CN(C)C)c2)n1]

The TFA salt of the title compound was prepared according to the procedures described in Example 14, using N,N-dimethyl-1-(3-(4,4,5,5-tetramethyl-1,3,2-dioxaborolan-2-yl)phenyl)methanamine instead of o-tolylboronic acid as starting material. LCMS calculated for $C_{29}H_{27}F_2N_6O_2$ (M+H)$^+$: m/z=529.2; Found: 529.2.

Example 25. N-(4-((1S,4S)-2,5-diazabicyclo[2.2.1]heptan-2-yl)-7-fluoro-1-(2-hydroxyethyl)-1H-indazol-5-yl)-2-(2-fluoro-6-methoxyphenyl)pyrimidine-4-carboxamide

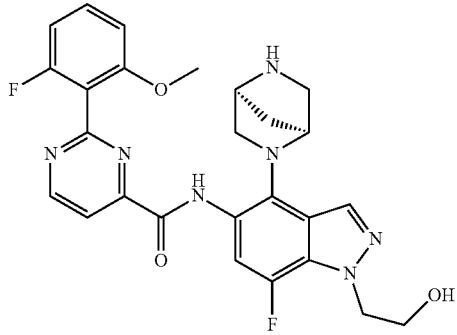 [SMILES: COc1cccc(F)c1-c1nccc(C(=O)Nc2cc(F)c3c(cnn3CCO)c2N2C[C@@H]3C[C@H]2CN3)n1]

The TFA salt of the title compound was prepared according to the procedures described in Example 17, using (1S,4S)-2,5-diazabicyclo[2.2.1]heptane instead of tert-butyl (R)-pyrrolidin-3-ylcarbamate as starting material. LCMS calculated for $C_{26}H_{26}F_2N_7O_3$(M+H)$^+$: m/z=522.2; Found: 522.2.

Example 26. N-(4-((1S,4S)-2,5-diazabicyclo[2.2.1]heptan-2-yl)-7-fluoro-1-(2-methoxyethyl)-1H-indazol-5-yl)-2-(2-fluoro-6-methoxyphenyl)pyrimidine-4-carboxamide

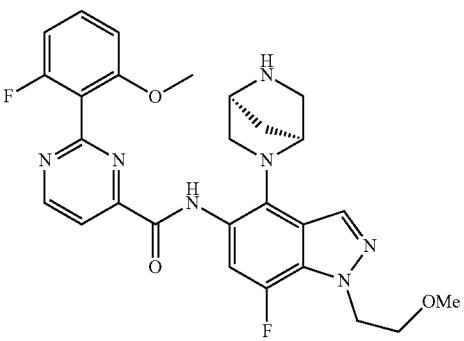 [SMILES: COCCn1ncc2c(N3C[C@@H]4C[C@H]3CN4)c(NC(=O)c3ccnc(-c4c(F)cccc4OC)n3)cc(F)c21]

The TFA salt of the title compound was prepared according to the procedures described in Examples 17 and 25, using 1-bromo-2-methoxyethane instead of (2-bromoethoxy)(tert-butyl)dimethylsilane as starting material. LCMS calculated for $C_{27}H_{28}F_2N_7O_3$ (M+H)$^+$: m/z=536.2; Found: 536.3. 1H NMR (500 MHz, DMSO-d6) δ 10.45 (s, 1H), 9.27 (d, J=5.0 Hz, 1H), 8.39 (d, J=1.9 Hz, 1H), 8.15 (d, J=5.0 Hz, 1H), 7.67 (d, J=12.8 Hz, 1H), 7.56 (q, J=8.4 Hz, 1H), 7.08 (d, J=8.5 Hz, 1H), 7.00 (t, J=8.8 Hz, 1H), 4.63 (t, J=5.2 Hz, 2H), 4.56-4.49 (m, 1H), 4.45-4.37 (m, 1H), 3.83-3.79 (m, 2H), 3.78 (s, 3H), 3.75 (t, J=5.2 Hz, 2H), 3.51 (d, J=10.8 Hz, 2H), 3.38-3.31 (m, 1H), 3.27-3.22 (m, 1H), 3.20 (s, 3H), 2.06 (d, J=10.3 Hz, 1H), 1.79 (d, J=10.4 Hz, 1H) ppm.

Example 27. N-(4-(4-(Dimethylamino)piperidin-1-yl)-3-iodo-1-methyl-1H-indazol-5-yl)-2-(2-fluoro-6-methoxyphenyl)pyrimidine-4-carboxamide

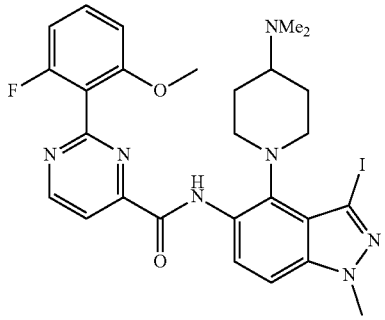 [SMILES: COc1cccc(F)c1-c1nccc(C(=O)Nc2ccc3c(c(I)nn3C)c2N2CCC(N(C)C)CC2)n1]

Step 1. 4-Bromo-3-iodo-5-nitro-1H-indazole

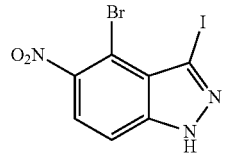 [SMILES: O=[N+]([O-])c1ccc2[nH]nc(I)c2c1Br]

NIS (1.4 g, 6.32 mmol) was added to a solution of 4-bromo-5-nitro-1H-indazole (1.5 g, 6.20 mmol) in DMF (15 mL). The reaction mixture was stirred at 70° C. for 2 h, cooled to room temperature, treated with water, and the product was collected by filtration. The solid was washed with water and air dried. LCMS calculated for $C_7H_4BrIN_3O_2(M+H)^+$: m/z=367.9; Found: 367.8.

Step 2. 4-Bromo-3-iodo-1-methyl-5-nitro-1H-indazole

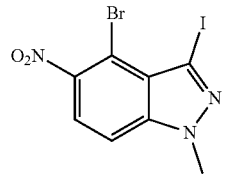

NaH (0.288 g, 7.20 mmol, 60% in mineral oil) was added to a solution of 4-bromo-3-iodo-5-nitro-1H-indazole (2.12 g, 5.76 mmol) and iodomethane (0.721 mL, 11.52 mmol) in DMF (14 mL). The reaction mixture was stirred at room temperature for 1 h, treated with water and the precipitated product was collected by filtration. The solid was washed with water and air dried. LCMS calculated for $C_8H_6BrIN_3O_2(M+H)^+$: m/z=381.9; Found: 381.9.

Step 3. 1-(3-Iodo-1-methyl-5-nitro-1H-indazol-4-yl)-N,N-dimethylpiperidin-4-amine

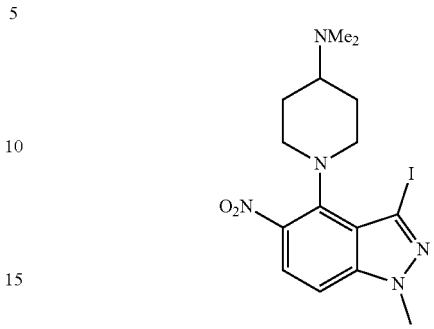

A solution of 4-bromo-3-iodo-1-methyl-5-nitro-1H-indazole (2.1 g, 5.50 mmol) and N,N-dimethylpiperidin-4-amine (1.057 g, 8.25 mmol) in DMSO (18 mL) was treated with triethylamine (1.150 mL, 8.25 mmol). The reaction mixture was heated to 80° C. for 1 h. After cooling to room temperature, the reaction mixture was diluted with dichloromethane, washed with brine, dried over sodium sulfate, and concentrated. The crude product was used in the next step without further purification. LCMS calculated for $C_{15}H_{21}IN_5O_2(M+H)^+$: m/z=430.1; Found: 430.2.

Step 4. 4-(4-(Dimethylamino)piperidin-1-yl)-3-iodo-1-methyl-1H-indazol-5-amine

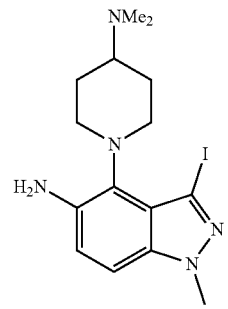 [SMILES: CN(C)C1CCN(c2c(N)ccc3c2c(I)nn3C)CC1]

A mixture of 1-(3-iodo-1-methyl-5-nitro-1H-indazol-4-yl)-N,N-dimethylpiperidin-4-amine (2.36 g, 5.50 mmol), iron (1.53 g, 27.5 mmol) and ammonium chloride (1.76 g, 33.0 mmol) in THF (5 mL), water (5 mL) and methanol (5 mL) was stirred at 60° C. for 3 h. After cooling to room temperature, the mixture was filtered through a pad of Celite and diluted with dichloromethane. The organic phase was separated, washed with brine, dried over sodium sulfate, and concentrated. The crude product was used in the next step without further purification. LCMS calculated for $C_{15}H_{23}IN_5 (M+H)^+$: m/z=400.1; Found: 400.2.

Step 5. N-(4-(4-(Dimethylamino)piperidin-1-yl)-3-iodo-1-methyl-1H-indazol-5-yl)-2-(2-fluoro-6-methoxyphenyl)pyrimidine-4-carboxamide HATU (486 mg, 1.28 mmol) was added to a solution of 4-(4-(dimethylamino)piperidin-1-yl)-3-iodo-1-methyl-1H-indazol-5-amine (340 mg, 0.852 mmol), 2-(2-fluoro-6-methoxyphenyl)pyrimidine-4-carboxylic acid (211 mg, 0.852 mmol) and DIPEA (297 μL, 1.7 mmol) in DMF (5 mL). The reaction mixture was stirred at room temperature for 30 min, then water was added, and the precipitated product was collected by filtration. The solid was washed with water, air dried, and then re-dissolved in a mixture of acetonitrile and TFA and purified with prep-LCMS (XBridge C18 column, eluting with a gradient of acetonitrile/water containing 0.1% TFA, at flow rate of 60 mL/min) to provide the TFA salt of the title compound. LCMS calculated for $C_{27}H_{30}FIN_7O_2(M+H)^+$: m/z=630.1; Found: 630.2.

Example 28. N-(4-(4-(Dimethylamino)piperidin-1-yl)-1,3-dimethyl-1H-indazol-5-yl)-2-(2-fluoro-6-methoxyphenyl)pyrimidine-4-carboxamide

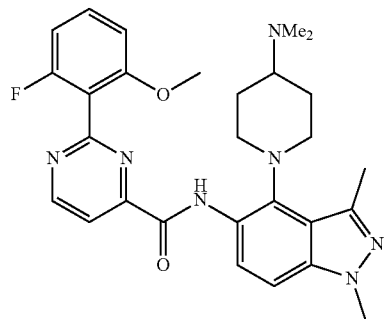

A mixture of N-(4-(4-(dimethylamino)piperidin-1-yl)-3-iodo-1-methyl-1H-indazol-5-yl)-2-(2-fluoro-6-methoxyphenyl)pyrimidine-4-carboxamide (Example 26, 10 mg, 0.016 mmol), trimethylboroxine (3.6 μl, 0.032 mmol), chloro(2-dicyclohexylphosphino-2',4',6'-triisopropyl-1,1'-biphenyl)[2-(2'-amino-1,1'-biphenyl)]palladium(II) (1.3 mg, 1.6 μmol) and potassium phosphate, tribasic (6.7 mg, 0.032 mmol) was combined with 1,4-dioxane (1000 μl) and water (100 μl). The reaction flask was evacuated, back filled with nitrogen, and then stirred at 80° C. overnight. The reaction mixture was cooled to room temperature, filtered, diluted with CH$_3$CN and purified with prep-LCMS (XBridge C18 column, eluting with a gradient of acetonitrile/water containing 0.1% TFA, at flow rate of 60 mL/min) to provide the TFA salt of the title compound. LCMS calculated for $C_{28}H_{33}FN_7O_2(M+H)^+$: m/z=518.2; Found: 518.2.

Example 29. N-(4-(4-(Dimethylamino)piperidin-1-yl)-1-methyl-3-phenyl-1H-indazol-5-yl)-2-(2-fluoro-6-methoxyphenyl)pyrimidine-4-carboxamide

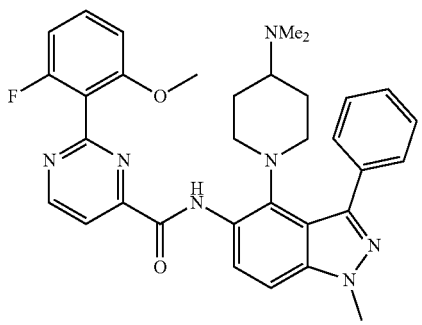 [SMILES: COc1cccc(F)c1-c1nccc(C(=O)Nc2ccc3c(c(-c4ccccc4)nn3C)c2N2CCC(N(C)C)CC2)n1]

The TFA salt of the title compound was prepared according to the procedures described in Example 27, using phenylboronic acid instead of trimethylboroxine as starting material. LCMS calculated for $C_{33}H_{35}FN_7O_2(M+H)^+$: m/z=580.3; Found: 580.3.

Example 30. N-(4-(4-(Dimethylamino)piperidin-1-yl)-1-methyl-3-(1-methyl-1H-pyrazol-4-yl)-1H-indazol-5-yl)-2-(2-fluoro-6-methoxyphenyl)pyrimidine-4-carboxamide

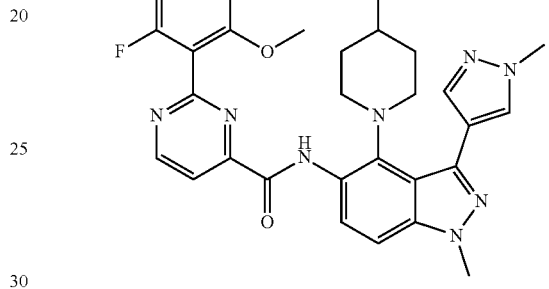

The TFA salt of the title compound was prepared according to the procedures described in Example 27, using 1-methyl-4-(4,4,5,5-tetramethyl-1,3,2-dioxaborolan-2-yl)-1H-pyrazole instead of trimethylboroxine as starting material. LCMS calculated for $C_{31}H_{35}FN_9O_2(M+H)^+$: m/z=584.3; Found: 584.4.

Example 31. N-(4-((2S,4S)-4-Amino-2-(hydroxymethyl)pyrrolidin-1-yl)-7-fluoro-1-(2-methoxyethyl)-1H-indazol-5-yl)-2-(2-fluoro-6-m ethoxyphenyl)pyrimidine-4-carboxamide

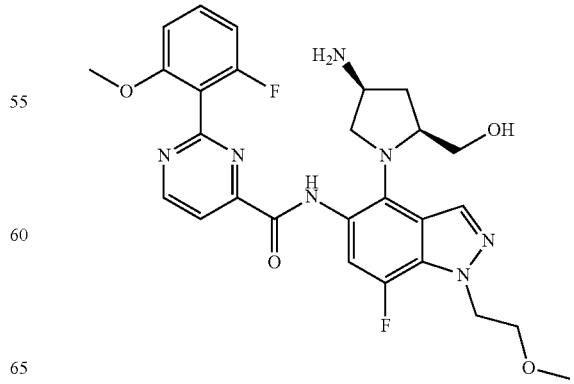

Step 1. 4-Bromo-7-fluoro-1-(2-methoxyethyl)-5-nitro-1H-indazole

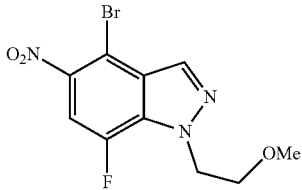 [SMILES: COCCn1ncc2c(Br)c([N+](=O)[O-])cc(F)c21]

A mixture of 4-bromo-7-fluoro-5-nitro-1H-indazole (400 mg, 1.54 mmol) and cesium carbonate (1 g, 3.08 mmol) in DMF (8 ml) was treated with 1-bromo-2-methoxyethane (217 µl, 2.31 mmol) and the reaction mixture was heated to 80° C. for 1 h. The mixture was then treated with water and the product was extracted with ethyl acetate. The separated organic phase was washed with water and brine, dried over sodium sulfate and concentrated. The crude product was purified by Biotage Isolera™ (flash purification system with ethyl acetate/hexane at a ratio from 0 to 100%) to provide the desired product (110 mg, 23%). LCMS calculated for $C_{10}H_{10}BrFN_3O_3$ $(M+H)^+$: m/z=318.0/320.0; found 318.0/320.0.

Step 2. tert-Butyl (3S,5S)-1-(5-amino-7-fluoro-1-(2-methoxyethyl)-1H-indazol-4-yl)-5-(hydroxymethyl)pyrrolidin-3-ylcarbamate

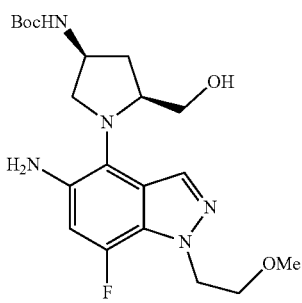 [SMILES: COCCn1ncc2c(N3C[C@@H](NC(=O)OC(C)(C)C)C[C@H]3CO)c(N)cc(F)c21]

A solution of 4-bromo-7-fluoro-1-(2-methoxyethyl)-5-nitro-1H-indazole (36 mg, 0.113 mmol) and tert-butyl ((3S,5S)-5-(hydroxymethyl)pyrrolidin-3-yl)carbamate (29.4 mg, 0.136 mmol) in DMSO (566 µl) was treated with triethylamine (31.5 µl, 0.226 mmol) and the reaction mixture was heated to 90° C. for 1 h. The mixture was then treated with water and the product was extracted with ethyl acetate. The separated organic phase was washed with water and brine, dried over sodium sulfate and concentrated. The residue was dissolved in a 1:1:1 mixture of THF/MeOH/Water (1.5 mL) and treated with iron (25.3 mg, 0.453 mmol) and ammonium chloride (36.3 mg, 0.679 mmol). The mixture was heated to 60° C. for 1 h, then diluted with ethyl acetate and filtered through a plug of Celite. The filtrate was washed with water and brine, dried over sodium sulfate and concentrated. The crude product was used in the next step without further purification. LCMS calculated for $C_{20}H_{31}FN_5O_4(M+H)^+$: m/z=424.2; found 424.2.

Step 3. N-(4-((2S,4S)-4-Amino-2-(hydroxymethyl)pyrrolidin-1-yl)-7-fluoro-1-(2-methoxyethyl)-1H-indazol-5-yl)-2-(2-fluoro-6-methoxyphenyl)pyrimidine-4-carboxamide A mixture of 2-(2-fluoro-6-methoxyphenyl)pyrimidine-4-carboxylic acid (11.72 mg, 0.047 mmol), HATU (21.55 mg, 0.057 mmol) and tert-butyl ((3S,5S)-1-(5-amino-7-fluoro-1-(2-methoxyethyl)-1H-indazol-4-yl)-5-(hydroxymethyl)pyrrolidin-3-yl)carbamate (Step 2, 20 mg, 0.047 mmol) was treated with DMF (236 µl) and Hunig's base (16.50 µl, 0.094 mmol) and the reaction mixture stirred at room temperature for 30 mins. The mixture was then diluted with water and the resulting precipitate was collected by filtration and washed with water and hexanes. The precipitate was dissolved in TFA (1.5 mL) and allowed to stand for 30 mins at room temperature. The solution was diluted with methanol and purified with prep-LCMS (XBridge C18 column, eluting with a gradient of acetonitrile/water containing 0.1% TFA, at flow rate of 60 mL/min). LCMS calculated for $C_{27}H_{30}F_2N_7O_4(M+H)^+$: m/z=554.2; found 554.2. $^1$H NMR (500 MHz, DMSO) δ 10.72 (s, 1H), 9.26 (d, J=5.0 Hz, 1H), 8.38 (s, 1H), 8.24 (d, J=13.6 Hz, 1H), 8.18 (d, J=5.0 Hz, 1H), 7.86 (s, 2H), 7.63-7.48 (m, 1H), 7.05 (s, 1H), 7.00 (t, J=8.7 Hz, 1H), 5.33 (s, 1H), 4.65 (t, J=5.2 Hz, 2H), 3.78 (d, J=7.5 Hz, 7H), 3.56 (dd, J=10.0, 4.8 Hz, 1H), 3.36 (d, J=10.2 Hz, 1H), 3.22 (s, 3H), 3.18 (d, J=11.1 Hz, 2H), 2.70-2.60 (m, 1H), 1.83 (d, J=16.4 Hz, 1H).

Example 32. N-(4-((2S,4S)-4-Amino-2-(hydroxymethyl)pyrrolidin-1-yl)-7-fluoro-1-((R)-tetrahydrofuran-3-yl)-1H-indazol-5-yl)-2-(2-fluoro-6-methoxyphenyl)pyrimidine-4-carboxamide

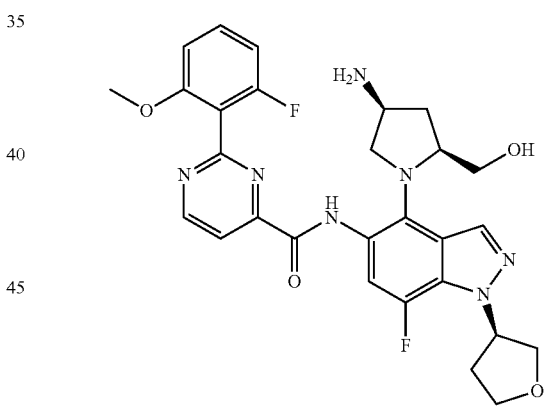

Step 1. (R)-4-Bromo-7-fluoro-5-nitro-1-(tetrahydrofuran-3-yl)-1H-indazole

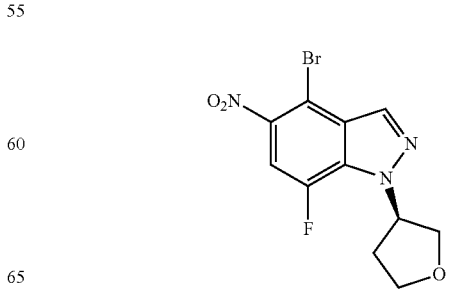

A solution of 4-bromo-7-fluoro-5-nitro-1H-indazole (300 mg, 1.15 mmol), (S)-tetrahydrofuran-3-ol (117 μl, 1.73 mmol) and triphenylphosphine (454 mg, 1.731 mmol) in THF (5769 μl) was treated with DIAD (336 μl, 1.731 mmol) dropwise and the reaction mixture was stirred at room temperature overnight. The mixture was then concentrated and purified by Biotage Isolera™ (flash purification system with ethyl acetate/hexane at a ratio from 0 to 60%) to provide the desired product as a yellow solid (190 mg, 50%). LCMS calculated for $C_{11}H_{10}BrFN_3O_3(M+H)^+$: m/z=330.0; Found: 330.0.

Step 2. N-(4-((2S,4S)-4-Amino-2-(hydroxymethyl) pyrrolidin-1-yl)-7-fluoro-1-((R)-tetrahydrofuran-3-yl)-1H-indazol-5-yl)-2-(2-fluoro-6-methoxyphenyl) pyrimidine-4-carboxamide This compound was prepared according to the procedures described in Example 31, steps 2 and 3 using (R)-4-bromo-7-fluoro-5-nitro-1-(tetrahydrofuran-3-yl)-1H-indazole instead of 4-bromo-7-fluoro-1-(2-methoxyethyl)-5-nitro-1H-indazole as starting material. LCMS calculated for $C_{28}H_{30}F_2N_7O_4(M+H)^+$: m/z=566.2; Found: 566.2. $^1$H NMR (500 MHz, DMSO) δ 10.74 (s, 1H), 9.27 (d, J=5.0 Hz, 1H), 8.39 (d, J=1.9 Hz, 1H), 8.28 (d, J=13.7 Hz, 1H), 8.18 (d, J=5.0 Hz, 1H), 7.85 (s, 3H), 7.63-7.47 (m, 1H), 7.06 (d, J=8.5 Hz, 1H), 6.99 (t, J=8.7 Hz, 1H), 5.54 (s, 1H), 4.11 (dd, J=9.3, 6.3 Hz, 1H), 4.04 (q, J=7.6 Hz, 1H), 3.99 (dd, J=9.2, 3.5 Hz, 1H), 3.94-3.87 (m, 1H), 3.77 (s, 5H), 3.56 (dd, J=10.0, 4.8 Hz, 1H), 3.35 (d, J=11.1 Hz, 1H), 3.18 (qd, J=10.9, 2.6 Hz, 2H), 2.67 (ddd, J=13.9, 9.5, 6.6 Hz, 1H), 2.46 (q, J=7.4 Hz, 2H), 1.83 (d, J=13.6 Hz, 1H).

Example 33. (R)—N-(7-Fluoro-4-(3-(hydroxymethyl)piperazin-1-yl)-2-methyl-2H-indazol-5-yl)-2-(2-fluoro-6-methoxyphenyl)pyrimidine-4-carboxamide

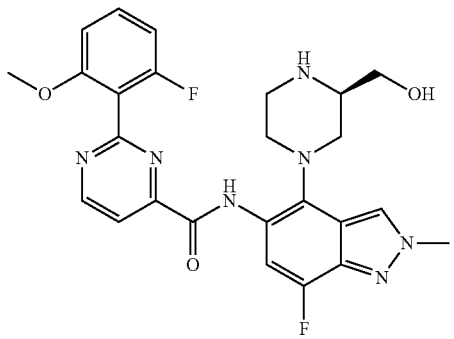

This compound was prepared according to the procedures described in Example 1, using (R)-tert-butyl 2-(hydroxymethyl)piperazine-1-carboxylate instead of tert-butyl (1S,4S)-2,5-diazabicyclo[2.2.1]heptane-2-carboxylate as starting material. LCMS calculated for $C_{25}H_{26}F_2N_7O_3(M+H)^+$: m/z=510.2; Found: 510.2. $^1$H NMR (600 MHz, DMSO) δ 11.07 (s, 1H), 9.47 (d, J=9.9 Hz, 1H), 9.30 (d, J=4.9 Hz, 2H), 8.66 (s, 1H), 8.24 (s, 1H), 8.17 (d, J=4.9 Hz, 1H), 7.57 (t, J=8.5 Hz, 1H), 7.09 (dd, J=8.4, 4.2 Hz, 2H), 5.43 (s, 1H), 4.23 (s, 3H), 3.79 (s, 3H), 3.61 (dd, J=11.2, 4.2 Hz, 1H), 3.58-3.48 (m, 3H), 3.47-3.38 (m, 1H), 3.33 (d, J=12.0 Hz, 1H), 3.13 (d, J=11.6 Hz, 1H), 3.08-2.98 (m, 2H), 2.78 (d, J=10.2 Hz, 1H).

Example 34. N-(4-((2S,4S)-4-Amino-2-(hydroxymethyl)pyrrolidin-1-yl)-1-(3-cyanopyridin-4-yl)-7-fluoro-1H-indazol-5-yl)-2-(2-fluoro-6-methoxyphenyl)pyrimidine-4-carboxamide

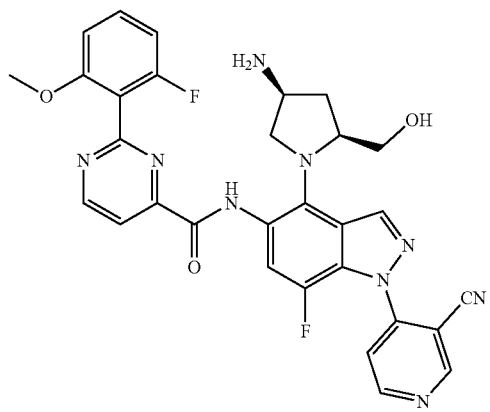 [SMILES: COc1cccc(F)c1-c1nccc(C(=O)Nc2cc(F)c3c(cnn3-c3ccncc3C#N)c2N2C[C@@H](N)C[C@H]2CO)n1]

Step 1. tert-Butyl (3S,5S)-5-((tert-butyldimethylsilyloxy)methyl)pyrrolidin-3-ylcarbamate

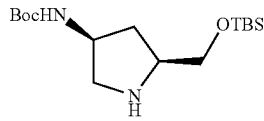

A solution of tert-butyl ((3S,5S)-5-(hydroxymethyl)pyrrolidin-3-yl)carbamate (1. g, 4.62 mmol) and tert-butyldimethylsilyl chloride (0.767 g, 5.09 mmol) in DCM (23 ml) was treated with triethylamine (0.967 ml, 6.94 mmol) and the reaction mixture was stirred at room temperature overnight. The reaction was then treated with saturated sodium bicarbonate solution. The phases were separated and the aqueous phase was extracted with DCM. The combined organic phases were dried over sodium sulfate and concentrated. The resulting yellow oil was used in the next step without further purification (1.47 g, 96%). LCMS calculated for $C_{16}H_{35}N_2O_3Si (M+H)^+$: m/z=331.2; Found: 331.2.

Step 2. tert-Butyl (3S,5S)-5-((tert-butyldimethylsilyloxy)methyl)-1-(7-fluoro-5-nitro-1H-indazol-4-yl) pyrrolidin-3-ylcarbamate

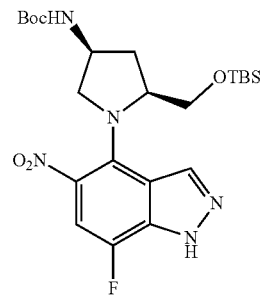 [SMILES: CC(C)(C)OC(=O)N[C@H]1C[C@@H](CO[Si](C)(C)C(C)(C)C)N(c2c([N+](=O)[O-])cc(F)c3[nH]ncc23)C1]

A solution of 4-bromo-7-fluoro-5-nitro-1H-indazole (330 mg, 1.269 mmol) and tert-butyl ((3S,5S)-5-(((tert-butyldimethylsilyl)oxy)methyl)pyrrolidin-3-yl)carbamate (503 mg, 1.523 mmol) in DMSO (5 ml) was treated with triethylamine (531 µl, 3.81 mmol) and the reaction mixture was heated to 90° C. for 1 hr. The mixture was cooled, treated with water and the product was extracted with ethyl acetate. The separated organic phase was washed with water and brine, dried over sodium sulfate and concentrated. The crude product was purified by Biotage Isolera™ (flash purification system with ethyl acetate/hexane at a ratio from 0 to 100%) to provide the desired product as a solid (457 mg, 71%). LCMS calculated for $C_{23}H_{37}FN_5O_5Si$ (M+H)$^+$: m/z=510.2; Found: 510.2.

Step 3. tert-Butyl (3S,5S)-1-(5-amino-1-(3-cyanopyridin-4-yl)-7-fluoro-1H-indazol-4-yl)-5-((tert-butyldimethylsilyloxy)methyl)pyrrolidin-3-ylcarbamate

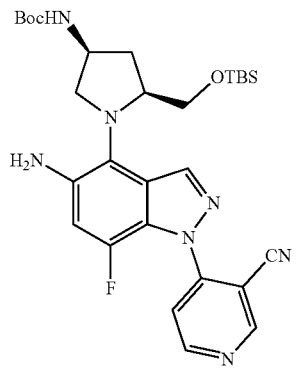 [SMILES: CC(C)(C)OC(=O)N[C@H]1C[C@@H](CO[Si](C)(C)C(C)(C)C)N(c2c(N)cc(F)c3c2cnn3-c2ccncc2C#N)C1]

A suspension of tert-butyl ((3S,5S)-5-(((tert-butyldimethylsilyl)oxy)methyl)-1-(7-fluoro-5-nitro-1H-indazol-4-yl)pyrrolidin-3-yl)carbamate (50 mg, 0.098 mmol), 4-chloronicotinonitrile (27.2 mg, 0.196 mmol) in DMF (1 ml) was treated with sodium hydride (9.81 mg, 0.245 mmol) and the reaction mixture was stirred at room temperature for 2 h. The reaction mixture was then treated with water and the product extracted with ethyl acetate. The separated organic phase was washed with water and brine, dried over sodium sulfate and concentrated. The crude product was purified by Biotage Isolera™ (flash purification system with ethyl acetate/hexane at a ratio from 0 to 100%) to provide the desired intermediate as an orange oil. To this intermediate was added a 1:1:1 mixture of THF/MeOH/water (1.5 mL), followed by iron (21.91 mg, 0.392 mmol) and ammonium chloride (31.5 mg, 0.59 mmol). The mixture was heated to 60° C. for 1 h, then diluted with ethyl acetate and filtered through a plug of Celite. The filtrate was washed with water and brine, dried over sodium sulfate and concentrated. The crude product was used in the next step without further purification. LCMS calculated for $C_{29}H_{41}FN_7O_3Si$ (M+H)$^+$: m/z=582.2; Found: 582.2.

Step 4. N-(4-((2S,4S)-4-Amino-2-(hydroxymethyl)pyrrolidin-1-yl)-1-(3-cyanopyridin-4-yl)-7-fluoro-1H-indazol-5-yl)-2-(2-fluoro-6-methoxyphenyl)pyrimidine-4-carboxamide A solution of 2-(2-fluoro-6-methoxyphenyl)pyrimidine-4-carboxylic acid (15.90 mg, 0.064 mmol), HATU (29.8 mg, 0.078 mmol), tert-butyl (3S,5S)-1-(5-amino-1-(3-cyanopyridin-4-yl)-7-fluoro-1H-indazol-4-yl)-5-((tert-butyldimethylsilyloxy)methyl)pyrrolidin-3-ylcarbamate (41 mg, 0.071 mmol) in DMF (356 µl) was treated with Hunig's base (24.87 µl, 0.142 mmol) and the reaction mixture was stirred at room temperature for 30 mins. The reaction mixture was then treated with water and the product was extracted with ethyl acetate. The separated organic phase was washed with water and brine, dried over sodium sulfate and concentrated. The crude residue was dissolved in MeOH (0.5 mL) and treated with 4N HCl in dioxane (0.5 mL). The mixture was stirred at room temperature for 30 mins, then diluted with MeOH and purified with prep-LCMS (XBridge C18 column, eluting with a gradient of acetonitrile/water containing 0.1% TFA, at flow rate of 60 mL/min). LCMS calculated for $C_{30}H_{26}F_2N_9O_3$(M+H)$^+$: m/z=598.2; Found: 598.2.

Example 35. N-(4-((2S,4S)-2-(Aminomethyl)-4-hydroxypyrrolidin-1-yl)-7-fluoro-1-methyl-1H-indazol-5-yl)-2-(2-fluoro-6-methoxyphenyl)pyrimidine-4-carboxamide

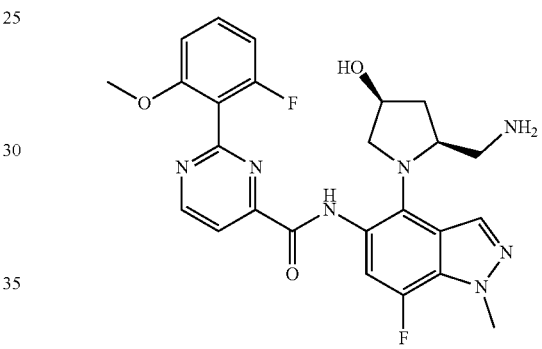

Step 1. (2S,4S)-tert-Butyl 4-(tert-butyldimethylsilyloxy)-2-(hydroxymethyl)pyrrolidine-1-carboxylate

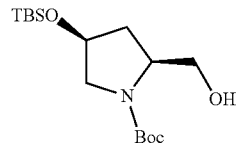 [SMILES: CC(C)(C)OC(=O)N1C[C@@H](O[Si](C)(C)C(C)(C)C)C[C@H]1CO]

A solution of (2S,4S)-1-tert-butyl 2-methyl 4-hydroxypyrrolidine-1,2-dicarboxylate (974 mg, 3.97 mmol) in DMF (20 ml) was treated with imidazole (406 mg, 5.96 mmol), DMAP (48.5 mg, 0.397 mmol) and TBS-Cl (718 mg, 4.77 mmol) and the reaction mixture was stirred at room temperature for 3 h. The reaction mixture was then treated with water and the product was extracted with ethyl acetate. The separated organic phase was washed with water and brine, dried over sodium sulfate and concentrated. The residue was dissolved in THF (40 mL) and treated with lithium borohydride (2M in THF, 2.98 ml, 5.96 mmol) dropwise at 0° C. The reaction mixture was allowed to warm up to room temperature and was stirred overnight. The reaction mixture was treated with 1 N HCl solution, diluted with water and the product was extracted with ethyl acetate. The separated organic phase was washed with water and brine, dried over sodium sulfate and concentrated. The residue was purified by CombiFlash™ (flash purification system with ethyl acetate/hexane at a ratio from 0 to 50%) to provide the desired product as a pale yellow oil (700 mg, 52%). LCMS calculated for $C_{16}H_{34}NO_4Si$ (M+H)$^+$: m/z=332.2; Found: 332.2.

Step 2. (2S,4S)-tert-Butyl 4-(tert-butyldimethylsilyloxy)-2-((1,3-dioxoisoindolin-2-yl)methyl)pyrrolidine-1-carboxylate

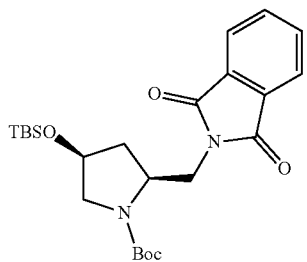 [SMILES: CC(C)(C)OC(=O)N1C[C@@H](O[Si](C)(C)C(C)(C)C)C[C@H]1CN1C(=O)c2ccccc2C1=O]

A solution of tert-butyl (2S,4S)-4-((tert-butyldimethylsilyl)oxy)-2-(hydroxymethyl)pyrrolidine-1-carboxylate (700 mg, 2.111 mmol), triphenylphosphine (831 mg, 3.17 mmol) and phthalimide (466 mg, 3.17 mmol) in THF (11 mL) was treated with DEAD (501 µL, 3.17 mmol) dropwise and the reaction mixture was stirred at room temperature overnight. The reaction mixture was concentrated and purified by CombiFlash™ (flash purification system with ethyl acetate/hexane at a ratio from 0 to 100%) to provide the desired product as a pale yellow oil (500 mg, 51%). LCMS calculated for $C_{24}H_{37}N_2O_5Si$ (M+H)$^+$: m/z=461.2; Found: 461.2.

Step 3. (2S,4S)-tert-Butyl 2-((benzyloxycarbonylamino)methyl)-4-(tert-butyldimethylsilyloxy)pyrrolidine-1-carboxylate

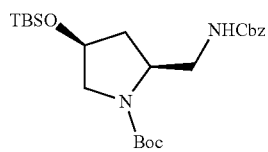 [SMILES: CC(C)(C)OC(=O)N1C[C@@H](O[Si](C)(C)C(C)(C)C)C[C@H]1CNC(=O)OCc1ccccc1]

A solution of tert-butyl (2S,4S)-4-((tert-butyldimethylsilyl)oxy)-2-((1,3-dioxoisoindolin-2-yl)methyl)pyrrolidine-1-carboxylate (497 mg, 1.079 mmol) in EtOH (11 mL) was treated with hydrazine hydrate (339 µl, 10.79 mmol) and the reaction mixture stirred at room temperature for 10 minutes, then at reflux for 30 mins. The mixture was then filtered through a plug of Celite and washed with ethanol. The filtrate was concentrated. The resultant residue was treated with DCM (3 mL), Hunig's base (283 µl, 1.618 mmol) and benzyl chloroformate (185 µl, 1.3 mmol). After stirring at room temperature for 30 mins, the mixture was concentrated and purified by CombiFlash™ (flash purification system with ethyl acetate/hexane at a ratio from 0 to 100%) to provide the desired product as a pale yellow oil (411 mg, 82%). LCMS calculated for $C_{24}H_{41}N_2O_5Si$ (M+H)$^+$: m/z=465.2; Found: 465.2.

Step 4. Benzyl ((2S,4S)-1-(5-amino-7-fluoro-1-methyl-1H-indazol-4-yl)-4-(tert-butyldimethylsilyloxy)pyrrolidin-2-yl)methylcarbamate

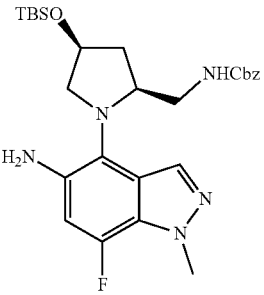 [SMILES: Cn1ncc2c(N3C[C@@H](O[Si](C)(C)C(C)(C)C)C[C@H]3CNC(=O)OCc3ccccc3)c(N)cc(F)c21]

A solution of tert-butyl (2S,4S)-2-((((benzyloxy)carbonyl)amino)methyl)-4-((tert-butyldimethylsilyl)oxy)pyrrolidine-1-carboxylate (102 mg, 0.219 mmol) in MeOH (1 mL) was treated with 4N HCl in dioxane (1 mL) and the reaction mixture was stirred at room temperature for 2 h, then concentrated. The resultant residue was treated with DMSO (608 µl) and triethylamine (76 µl, 0.547 mmol) followed by 4-bromo-7-fluoro-1-methyl-5-nitro-1H-indazole (50 mg, 0.182 mmol). The mixture was heated to 90° C. for 1 h. After cooling, the reaction was treated with water and extracted with ethyl acetate. The separated organic phase was washed with water and brine, dried over sodium sulfate and concentrated. The residue was dissolved in a 1:1:1 mixture of MeOH/THF/water (1.5 mL) and treated with iron (40.8 mg, 0.730 mmol) and ammonium chloride (58.6 mg, 1.095 mmol). The mixture was heated to 60° C. for 1 h, then diluted with ethyl acetate and filtered through a plug of Celite. The filtrate was washed with water and brine, dried over sodium sulfate and concentrated. The crude product was used in the next step without further purification. LCMS calculated for $C_{27}H_{39}FN_5O_3Si$ (M+H)$^+$: m/z=528.2; Found: 528.2.

Step 5. N-(4-((2S,4S)-2-(aminomethyl)-4-hydroxypyrrolidin-1-yl)-7-fluoro-1-methyl-1H-indazol-5-yl)-2-(2-fluoro-6-methoxyphenyl)pyrimidine-4-carboxamide A mixture of 2-(2-fluoro-6-methoxyphenyl)pyrimidine-4-carboxylic acid (36.0 mg, 0.145 mmol), HATU (66.2 mg, 0.174 mmol) and benzyl ((2S,4S)-1-(5-amino-7-fluoro-1-methyl-1H-indazol-4-yl)-4-(tert-butyldimethylsilyloxy)pyrrolidin-2-yl)methylcarbamate (60 mg, 0.145 mmol) was treated with DMF (726 µl) and Hunig's base (50.7 µl, 0.290 mmol) and the reaction mixture stirred at room temperature for 30 mins. The reaction mixture was diluted with water and the resulting precipitate was collected by filtration and washed with water and hexanes. The precipitate was treated with palladium on carbon (15 mg, 0.03 mmol) and MeOH (1 mL). The reaction mixture was evacuated, back filled with hydrogen gas from a balloon, then stirred at 60° C. overnight. The mixture was filtered through a plug of Celite and concentrated. 4N HCl in dioxane (1 mL) was then added to the resultant residue. After standing for 30 mins, the solution was diluted with methanol and purified with prep-LCMS (XBridge C18 column, eluting with a gradient of acetonitrile/water containing 0.1% TFA, at flow rate of 60 mL/min)

Example 36. N-(4-((1S,4S)-2,5-Diazabicyclo[2.2.1]heptan-2-yl)-7-fluoro-1-(2-fluoroethyl)-1H-indazol-5-yl)-2-(2-fluoro-6-methoxyphenyl)pyrimidine-4-carboxamide

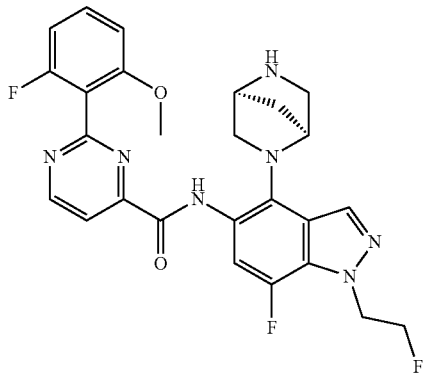 [SMILES: COc1cccc(F)c1-c1nccc(C(=O)Nc2cc(F)c3c(cnn3CCF)c2N2C[C@@H]3C[C@H]2CN3)n1]

The TFA salt of the title compound was prepared according to the procedures described in Examples 17 and 25, using 1-bromo-2-fluoroethane instead of (2-bromoethoxy)(tert-butyl)dimethylsilane as starting material. LCMS calculated for $C_{26}H_{25}F_3N_7O_2(M+H)^+$: m/z=524.2; Found: 524.3. $^1H$ NMR (500 MHz, DMSO-d6) δ 10.53-10.37 (s, 1H), 9.30-9.13 (d, J=5.0 Hz, 1H), 9.13-9.00 (br, 1H), 8.48-8.34 (d, J=2.1 Hz, 1H), 8.20-8.10 (d, J=5.0 Hz, 1H), 7.77-7.65 (d, J=12.8 Hz, 1H), 7.61-7.45 (td, J=8.5, 6.9 Hz, 1H), 7.10-7.04 (d, J=8.5 Hz, 1H), 7.04-6.94 (m, 1H), 4.90-4.84 (m, 1H), 4.84-4.81 (m, 1H), 4.79-4.72 (s, 2H), 4.56-4.49 (s, 1H), 4.47-4.35 (s, 1H), 3.86-3.80 (s, 1H), 3.80-3.75 (s, 3H), 3.56-3.49 (d, J=10.7 Hz, 1H), 3.41-3.31 (s, 1H), 3.29-3.16 (d, J=9.4 Hz, 1H), 2.10-2.02 (d, J=10.7 Hz, 1H), 1.87-1.66 (d, J=10.6 Hz, 1H) ppm.

Example 37. N-(4-((2S,4S)-4-Amino-2-(hydroxymethyl)pyrrolidin-1-yl)-7-fluoro-1-(2-methoxyethyl)-1H-indazol-5-yl)-2-(2-fluoro-6-(methoxy-d₃)-3-methylphenyl)pyrimidine-4-carboxamide

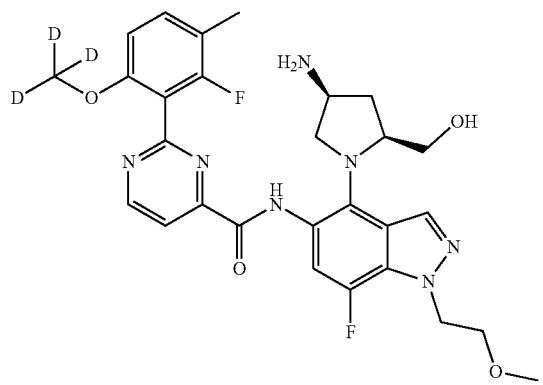 [SMILES: [2H]C([2H])([2H])Oc1ccc(C)c(F)c1-c1nccc(C(=O)Nc2cc(F)c3c(cnn3CCOC)c2N2C[C@@H](N)C[C@H]2CO)n1]

Step 1. 2-Fluoro-4-(methoxy-d₃)-1-methylbenzene

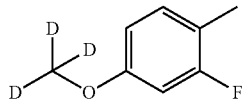

A solution of 3-fluoro-4-methylphenol (1.0 g, 7.93 mmol) in DMF (26.4 ml) was treated with potassium carbonate (1.644 g, 11.89 mmol) and iodomethane-d₃ (0.592 ml, 9.51 mmol) and the reaction mixture heated to 80° C. for 1 hr. The reaction Mixture was treated with water and extracted with diethyl ether. The organic phase was washed with water and brine, dried over sodium sulfate and concentrated. The crude product was used in the next step without further purification. LCMS calculated for $C_8H_7D_3FO$ $(M+H)^+$: m/z=144.2; Found: 144.2.

Step 2. 2-(2-Fluoro-6-(methoxy-d₃)-3-methylphenyl)-4,4,5,5-tetramethyl-1,3,2-dioxaborolane

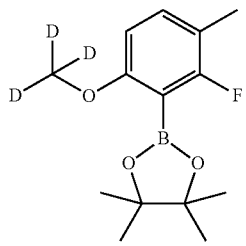 [SMILES: [2H]C([2H])([2H])Oc1ccc(C)c(F)c1B1OC(C)(C)C(C)(C)O1]

A solution of 2-fluoro-4-(methoxy-d₃)-1-methylbenzene (1.0 g, 6.98 mmol) and HMPA (1.823 ml, 10.48 mmol) in THF (35 ml) at −78° C. was treated with n-BuLi (2.5 M in hexanes, 3.35 ml, 8.38 mmol) dropwise and the reaction mixture was stirred at −78° C. for 1 hr. The mixture was then treated with 2-isopropoxy-4,4,5,5-tetramethyl-1,3,2-dioxaborolane (2.166 ml, 10.48 mmol) and the reaction mixture was stirred at −78° C. for 10 mins, then warmed up to r.t. by removing the cooling bath. The reaction was treated with aqueous 1N HCl and extracted with ethyl acetate. The organic phase was washed with water and brine, dried over sodium sulfate and concentrated. The crude product was used in the next step without further purification.

Step 3. Methyl 2-(2-fluoro-6-(methoxy-d₃)-3-methylphenyl)pyrimidine-4-carboxylic acid

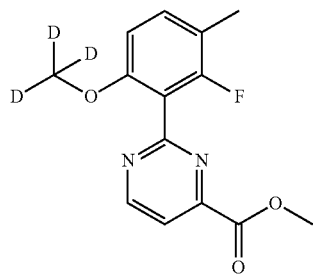 [SMILES: [2H]C([2H])([2H])Oc1ccc(C)c(F)c1-c1nccc(C(=O)OC)n1]

A solution of 2-(2-fluoro-6-(methoxy-d₃)-3-methylphenyl)-4,4,5,5-tetramethyl-1,3,2-dioxaborolane (1560 mg, 5.79 mmol) and Hunig's base (1012 µl, 5.79 mmol) in water (1.5 ml) and 1,4-dioxane (12 mL) was treated with methyl 2-chloropyrimidine-4-carboxylate (500 mg, 2.90 mmol) and ((t-Bu)₃P)₂Pd (74.0 mg, 0.145 mmol). The reaction flask was evacuated, back filled with nitrogen, then stirred at 80° C. overnight. The reaction mixture was then diluted with DCM and filtered through a plug of Celite. The filtrate was concentrated and the residue purified by Biotage Isolera™ (0-100% ethyl acetate in hexanes) to provide the desired product. LCMS calculated for $C_{14}H_{11}D_3FN_2O_3$ $(M+H)^+$: m/z=280.2; Found: 280.2.

Step 4. 2-(2-Fluoro-6-(methoxy-d₃)-3-methylphenyl)pyrimidine-4-carboxylic acid

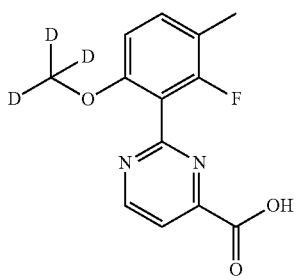 [SMILES: [2H]C([2H])([2H])Oc1ccc(C)c(F)c1-c1nccc(C(=O)O)n1]

The crude product from the previous step was dissolved in a 1:1 mixture of THF/water (4 mL). Lithium hydroxide (238 mg, 5.79 mmol) was added and the reaction mixture was heated to 60° C. for 1 hr, then acidified to pH 1 with 1 N HCl and extracted with ethyl acetate. The organic phase was washed with brine, dried over sodium sulfate and concentrated. The crude product was used in the next step without further purification. LCMS calculated for $C_{13}H_9D_3FN_2O_3$ $(M+H)^+$: m/z=266.2; Found: 266.2.

Step 5. N-(4-((2S,4S)-4-Amino-2-(hydroxymethyl)pyrrolidin-1-yl)-7-fluoro-1-(2-methoxyethyl)-1H-indazol-5-yl)-2-(2-fluoro-6-(methoxy-d₃)-3-methylphenyl)pyrimidine-4-carboxamide A solution of 2-(2-fluoro-6-(methoxy-d₃)-3-methylphenyl)pyrimidine-4-carboxylic acid (9.4 mg, 0.035 mmol), HATU (16 mg, 0.043 mmol) and tert-butyl ((3S,5S)-1-(5-amino-7-fluoro-1-(2-methoxyethyl)-1H-indazol-4-yl)-5-(hydroxymethyl)pyrrolidin-3-yl)carbamate (Example 31, step 2, 15 mg, 0.035 mmol) in DMF (3504 µl) was treated with Hunig's base (12 µl, 0.071 mmol) and the reaction mixture allowed to stir at r.t. for 30 mins. The reaction mixture was treated with water and extracted with ethyl acetate. The organic phase was washed with water and brine, dried over sodium sulfate and concentrated. The crude product was dissolved in TFA (1 mL) and allowed to stand at r.t. for 30 mins, then diluted with MeOH and purified with prep-LCMS (XBridge C18 column, eluting with a gradient of acetonitrile/water containing 0.1% TFA, at flow rate of 60 mL/min). LCMS calculated for $C_{28}H_{29}D_3F_2N_7O_4$ $(M+H)^+$: m/z=571.2; Found: 571.2.

Example 38. N-(4-((2S,4S)-4-Amino-2-(hydroxymethyl)pyrrolidin-1-yl)-7-fluoro-1-(2-methoxyethyl)-1H-indazol-5-yl)-2-(4-amino-2-fluoro-6-methoxyphenyl)pyrimidine-4-carboxamide

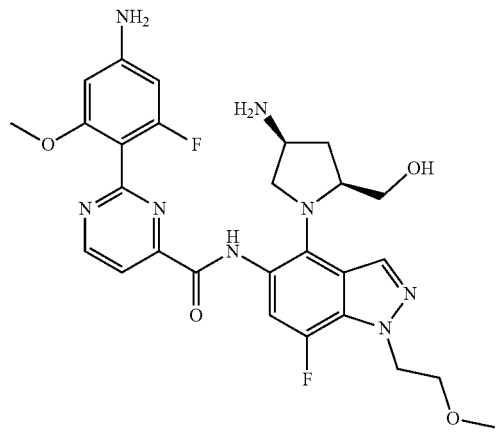

Step 1. 4-Bromo-3-fluoro-5-methoxyaniline

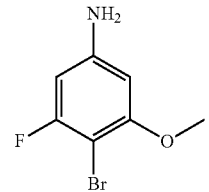

A solution of 3-fluoro-5-methoxyaniline (800 mg, 5.67 mmol) in DMF (20 ml) was treated with NBS (1 g, 5.67 mmol) and the reaction mixture stirred at r.t. for 1 hr. The reaction mixture was treated with water and ethyl acetate. The phases were separated and the aqueous phase extracted with additional ethyl acetate. The combined organic phases were washed with water and brine, dried over sodium sulfate and concentrated. The residue was purified by Biotage Isolera™ (10-50% ethyl acetate in hexanes) to provide the desired product as an off white solid (1.05 g, 84%). LCMS calculated for $C_7H_8BrFNO$ $(M+H)^+$: m/z=220.0/222.0; Found: 220.0/222.0.

Step 2. 3-Fluoro-5-methoxy-4-(4,4,5,5-tetramethyl-1,3,2-dioxaborolan-2-yl)aniline

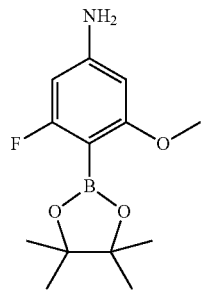 [SMILES: COc1cc(N)cc(F)c1B1OC(C)(C)C(C)(C)O1]

A mixture of 4-bromo-3-fluoro-5-methoxyaniline (1.05 g, 4.77 mmol), bis-pin (1.82 g, 7.16 mmol), dppf-PdCl₂ (0.390 g, 0.477 mmol) and potassium acetate (0.937 g, 9.54 mmol) in 1,4-dioxane (12 ml) was degassed by evacuation and back filling with nitrogen. The reaction mixture was stirred at 110° C. overnight. The reaction mixture was diluted with DCM and filtered through a plug of Celite. The filtrate was concentrated, then purified by Biotage Isolera™ (20-80% ethyl acetate in hexanes) to provide the desired product as a red oil. LCMS calculated for $C_{13}H_{20}BFNO_3$ (M+H)⁺: m/z=268.2; Found: 268.2.

Step 3. tert-Butyl ((3S,5S)-1-(5-(2-chloropyrimidine-4-carboxamido)-7-fluoro-1-(2-methoxyethyl)-1H-indazol-4-yl)-5-(hydroxymethyl)pyrrolidin-3-yl) carbamate

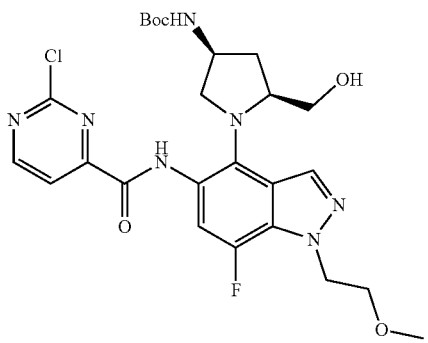 [SMILES: COCCn1ncc2c(N3C[C@@H](NC(=O)OC(C)(C)C)C[C@H]3CO)c(NC(=O)c3ccnc(Cl)n3)cc(F)c21]

A solution of 2-chloropyrimidine-4-carboxylic acid (70.4 mg, 0.444 mmol), HATU (186 mg, 0.488 mmol) and tert-butyl ((3S,5S)-1-(5-amino-7-fluoro-1-(2-methoxyethyl)-1H-indazol-4-yl)-5-(hydroxymethyl)pyrrolidin-3-yl)carbamate (188 mg, 0.444 mmol) in DMF (2 ml) was treated with Hunig's base (155 µl, 0.888 mmol) and the reaction mixture allowed to stir at r.t. for 30 mins. The reaction mixture was treated with water and extracted with ethyl acetate. The organic phase was washed with water and brine, dried over sodium sulfate and concentrated. The crude product was purified by Biotage Isolera™ (40-100% ethyl acetate in hexanes) to provide the desired product as an orange solid (207 mg, 83%). LCMS calculated for $C_{25}H_{32}ClFN_7O_5$ (M+H)⁺: m/z=564.2; Found: 564.2.

Step 4. N-(4-((2S,4S)-4-amino-2-(hydroxymethyl)pyrrolidin-1-yl)-7-fluoro-1-(2-methoxyethyl)-1H-indazol-5-yl)-2-(4-amino-2-fluoro-6-methoxyphenyl)pyrimidine-4-carboxamide A mixture of tert-butyl ((3S,5S)-5-(((tert-butyldimethylsilyl)oxy)methyl)-1-(5-(2-chloropyrimidine-4-carboxamido)-7-fluoro-1-(2-methoxyethyl)-1H-indazol-4-yl)pyrrolidin-3-yl)carbamate (100 mg, 0.147 mmol), 3-fluoro-5-methoxy-4-(4,4,5,5-tetramethyl-1,3,2-dioxaborolan-2-yl) aniline (59.1 mg, 0.221 mmol), XPhos Pd G2 (11.6 mg, 0.015 mmol) and Hunig's base (51.5 µl, 0.295 mmol) in water (300 µl) and 1,4-dioxane (1.2 ml) was evacuated, back filled with nitrogen and stirred at 90° C. overnight. The mixture was diluted with DCM and filtered through a plug of Celite. The filtrate was concentrated and the residue purified by Biotage (30-100% ethyl acetate in hexanes) to provide the desired product as a brown powder. The residue was dissolved in a 1:1 mixture of MeOH/4 N HCl in dioxane (1 mL) and heated to 80 degrees for 1 hr, then diluted with MeOH and purified with prep-LCMS (XBridge C18 column, eluting with a gradient of acetonitrile/water containing 0.1% TFA, at flow rate of 60 mL/min). LCMS calculated for $C_{27}H_{31}F_2N_8O_4$(M+H)⁺: m/z=569.2; Found: 569.2.

Example 39. N-(4-((2S,4S)-4-amino-2-(hydroxymethyl)pyrrolidin-1-yl)-7-fluoro-1-(2-methoxyethyl)-1H-indazol-5-yl)-2-(2-fluoro-6-m ethoxy-3-(methylcarbamoyl)phenyl)pyrimidine-4-carboxamide

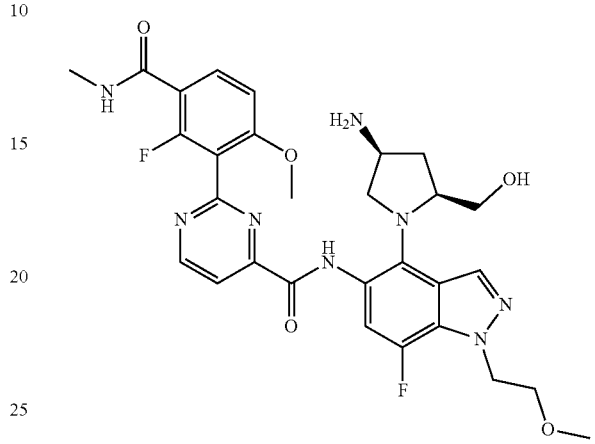

Step 1. Methyl 3-(4-((4-((2S,4S)-4-((tert-butoxycarbonyl)amino)-2-(hydroxymethyl)pyrrolidin-1-yl)-7-fluoro-1-(2-methoxyethyl)-1H-indazol-5-yl)carbamoyl)pyrimidin-2-yl)-2-fluoro-4-methoxybenzoate

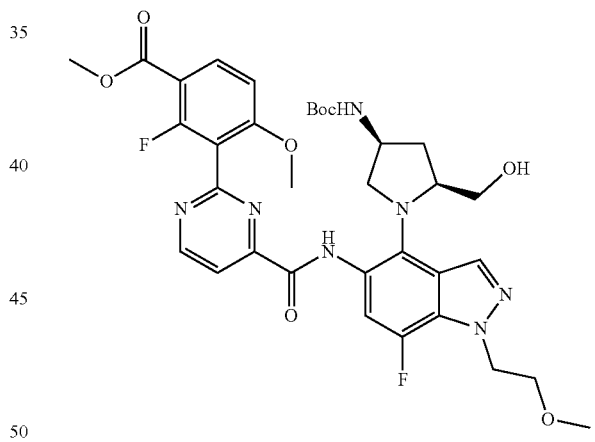

This compound was prepared similar to Example 37, using methyl 2-fluoro-4-methoxy-3-(4,4,5,5-tetramethyl-1,3,2-oxazaborolidin-2-yl)benzoate as the coupling partner. LCMS calculated for $C_{34}H_{40}F_2N_7O_8$ (M+H)⁺: m/z=712.2; Found: 712.2.

Step 2. N-(4-((2S,4S)-4-Amino-2-(hydroxymethyl) pyrrolidin-1-yl)-7-fluoro-1-(2-methoxyethyl)-1H-indazol-5-yl)-2-(2-fluoro-6-methoxy-3-(methylcarbamoyl)phenyl)pyrimidine-4-carboxamide Methyl 3-(4-((4-((2S,4S)-4-amino-2-(hydroxymethyl) pyrrolidin-1-yl)-7-fluoro-1-(2-methoxyethyl)-1H-indazol-5-yl)carbamoyl)pyrimidin-2-yl)-2-fluoro-4-methoxybenzoate (24 mg, 0.039 mmol) was dissolved in 1:1 THF/water (1 mL) and treated with LiOH (20 mg). After 30 mins at 60° C., the reaction mixture was treated with 1N HCl and extracted with ethyl acetate. The organic phase was dried and concentrated, then dissolved in DMF (0.5 mL) and treated with HATU (17.80 mg, 0.047 mmol), methanamine (39.0 µl, 0.078 mmol) and Hunig's base (14 µl, 0.078 mmol). The reaction mixture was stirred at r.t. for 30 mins, treated with water and extracted with ethyl acetate. The organic phase was washed with water and brine, dried over sodium sulfate and concentrated. The material was dissolved in a 1:1 mixture of MeOH/4N HCl in dioxane (1 mL) and allowed to stir at 80° C. for 30 mins, then diluted with MeOH and purified with prep-LCMS (XBridge C18 column, eluting with a gradient of acetonitrile/water containing 0.1% TFA, at flow rate of 60 mL/min). LCMS calculated for $C_{29}H_{33}F_2N_8O_5(M+H)^+$: m/z=611.2; Found: 611.2.

Example 40. N-(4-((2S,4S)-4-Amino-2-(hydroxymethyl)pyrrolidin-1-yl)-7-fluoro-1-(2-methoxyethyl)-1H-indazol-5-yl)-2-(2-fluoro-6-m ethoxy-3-(1-methyl-1H-pyrazol-4-yl)phenyl)pyrimidine-4-carboxamide

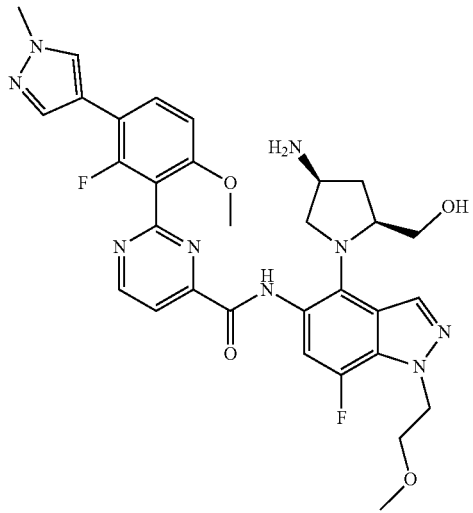 [SMILES: COCCn1ncc2c(N3C[C@@H](N)C[C@H]3CO)c(NC(=O)c3ccnc(-c4c(OC)ccc(-c5cnn(C)c5)c4F)n3)cc(F)c21]

Step 1. tert-Butyl ((3S,5S)-1-(5-(2-(3-chloro-2-fluoro-6-methoxyphenyl)pyrimidine-4-carboxamido)-7-fluoro-1-(2-methoxyethyl)-1H-indazol-4-yl)-5-(hydroxymethyl)pyrrolidin-3-yl)carbamate

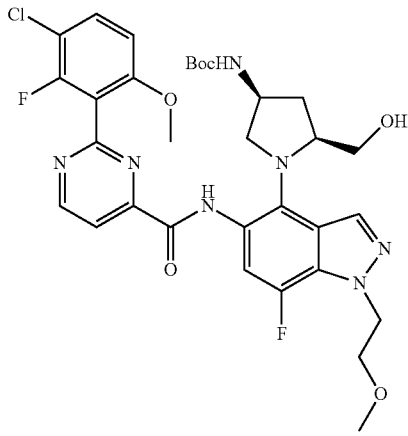 [SMILES: COCCn1ncc2c(N3C[C@@H](NC(=O)OC(C)(C)C)C[C@H]3CO)c(NC(=O)c3ccnc(-c4c(OC)ccc(Cl)c4F)n3)cc(F)c21]

This compound was prepared according to Example 37, using 2-(3-chloro-2-fluoro-6-methoxyphenyl)-4,4,5,5-tetramethyl-1,3,2-dioxaborolane as the coupling partner. LCMS calculated for $C_{32}H_{37}ClF_2N_7O_6$ (M+H)$^+$: m/z=688.2; Found: 688.2.

Step 2. N-(4-((2S,4S)-4-Amino-2-(hydroxymethyl)pyrrolidin-1-yl)-7-fluoro-1-(2-methoxyethyl)-1H-indazol-5-yl)-2-(2-fluoro-6-methoxy-3-(1-methyl-1H-pyrazol-4-yl)phenyl)pyrimidine-4-carboxamide A solution of tert-butyl ((3S,5S)-1-(5-(2-(3-chloro-2-fluoro-6-methoxyphenyl)pyrimidine-4-carboxamido)-7-fluoro-1-(2-methoxyethyl)-1H-indazol-4-yl)-5-(hydroxymethyl)pyrrolidin-3-yl)carbamate (20 mg, 0.029 mmol), XPhos Pd G2 (2 mg, 2.91 µmol), potassium phosphate (12 mg, 0.058 mmol) and 1-methyl-4-(4,4,5,5-tetramethyl-1,3,2-dioxaborolan-2-yl)-1H-pyrazole (12 mg, 0.058 mmol) in dioxane (200 µl) and water (48 µl) was evacuated, back filled with nitrogen, and then stirred at 90° C. for 1 hr. The reaction mixture was diluted with DCM/water and the phases separated. The organic phase was concentrated, then redissolved in TFA (1 mL) and allowed to stand at r.t. for 30 mins. The mixture was then diluted with MeOH and purified with prep-LCMS (XBridge C18 column, eluting with a gradient of acetonitrile/water containing 0. 1% TFA, at flow rate of 60 mL/min). LCMS calculated for $C_{31}H_{34}F_2N_9O_4(M+H)^+$: m/z=634.2; Found: 634.2.

Example 41. (R)—N-(7-Fluoro-1-methyl-4-(methyl(piperidin-3-yl)amino)-1H-indazol-5-yl)-2-(2-fluoro-6-methoxyphenyl)pyrimidine-4-carboxamide

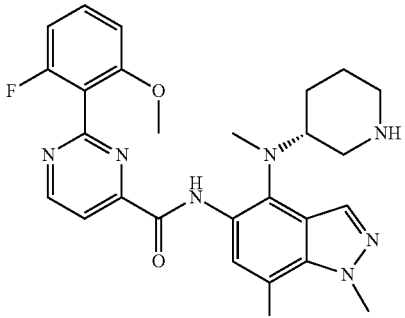

This compound was prepared according to the procedures described in Example 1, using tert-butyl (R)-3-(methylamino)piperidine-1-carboxylate instead of tert-butyl (1S, 4S)-2,5-diazabicyclo[2.2. 1]heptane-2-carboxylate as starting material. LCMS calculated for $C_{26}H_{28}F_2N_7O_2(M+H)^+$: m/z=508.2; Found: 508.2.

Example 42. N-(4-((2S,4S)-4-Amino-2-(hydroxymethyl)pyrrolidin-1-yl)-7-fluoro-1-(2-methoxyethyl)-1H-indazol-5-yl)-6-(2-fluoro-6-methoxyphenyl)picolinamide

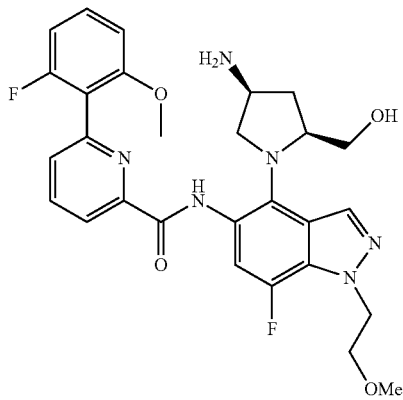 [SMILES: COCCn1ncc2c(N3C[C@@H](N)C[C@H]3CO)c(NC(=O)c3cccc(-c4c(F)cccc4OC)n3)cc(F)c21]

Step 1. tert-Butyl ((3S,5S)-1-(5-amino-7-fluoro-1-(2-methoxyethyl)-1H-indazol-4-yl)-5-(((tert-butyldimethylsilyl)oxy)methyl)pyrrolidin-3-yl)carbamate

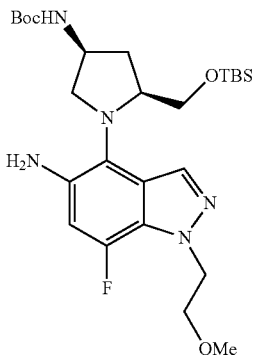 [SMILES: COCCn1ncc2c(N3C[C@@H](NC(=O)OC(C)(C)C)C[C@H]3CO[Si](C)(C)C(C)(C)C)c(N)cc(F)c21]

This compound was prepared in an analogous fashion to Example 31, steps 1-2, using tert-butyl ((3S,5S)-5-(((tert-butyldimethylsilyl)oxy)methyl)pyrrolidin-3-yl)carbamate (Example 34, Step 1) as starting material. LCMS calculated for $C_{26}H_{45}FN_5O_4Si$ $(M+H)^+$: m/z=538.2; Found: 538.2.

Step 2. tert-Butyl ((3S,5S)-5-(((tert-butyldimethylsilyl)oxy)methyl)-1-(5-(6-chloropicolinamido)-7-fluoro-1-(2-methoxyethyl)-1H-indazol-4-yl)pyrrolidin-3-yl)carbamate

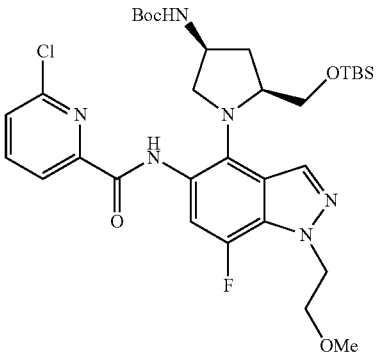 [SMILES: COCCn1ncc2c(N3C[C@@H](NC(=O)OC(C)(C)C)C[C@H]3CO[Si](C)(C)C(C)(C)C)c(NC(=O)c3cccc(Cl)n3)cc(F)c21]

This compound was prepared in an analogous fashion to Example 38, Step 3, with 6-chloropicolinic acid used as the coupling partner. LCMS calculated for $C_{32}H_{47}ClFN_6O_5Si$ $(M+H)^+$: m/z=677.2; Found: 677.2.

Step 3. N-(4-((2S,4S)-4-Amino-2-(hydroxymethyl)pyrrolidin-1-yl)-7-fluoro-1-(2-methoxyethyl)-1H-indazol-5-yl)-6-(2-fluoro-6-methoxyphenyl)picolinamide A solution of benzyl ((3S,5S)-5-(((tert-butyldimethylsilyl)oxy)methyl)-1-(5-(6-chloropicolinamido)-7-fluoro-1-(2-methoxyethyl)-1H-indazol-4-yl)pyrrolidin-3-yl)carbamate (24 mg, 0.034 mmol), (2-fluoro-6-methoxyphenyl)boronic acid (8.6 mg, 0.051 mmol), XPhos Pd G2 (2 mg, 3.37 µmol) and potassium phosphate, tribasic (14 mg, 0.067 mmol) in dioxane (200 µl) and water (56 µl) was evacuated, back filled with nitrogen and then stirred at 80° C. for 1 hr. The mixture was diluted with water and ethyl acetate. The phases were separated and the organic phase washed with water and brine, dried over sodium sulfate and concentrated. The crude residue was then dissolved in a 1:1 mixture of 4N HCl in dionxane/MeOH (1 mL), stirred for 30 mins at r.t., then diluted with MeOH purified with prep-LCMS (XBridge C18 column, eluting with a gradient of acetonitrile/water containing 0.1% TFA, at flow rate of 60 mL/min). LCMS calculated for $C_{28}H_{31}F_2N_6O_4(M+H)^+$: m/z=553.2; Found: 553.2.

Example A. HPK1 Kinase Binding Assay

A stock solution of 1 mM test compound was prepared in DMSO. The compound plate was prepared by 3-fold and 11-point serial dilutions. 0.1 µL of the compound in DMSO was transferred from the compound plate to the white 384 well polystyrene plates. The assay buffer contained 50 mM HEPES, pH 7.5, 0.01% Tween-20, 5 mM $MgCl_2$, 0.01% BSA, and 5 mM DTT. 5 µL of 4 nM active HPK1 (Signal-Chem M23-11G) prepared in the buffer was added to the plate. The enzyme concentration given was based on the given stock concentration reported by the vender. 5 µl of 18 nM tracer 222 (ThermoFisher PV6121) and 4 nM LanthaScreen Eu-Anti GST antibody (ThermoFisher PV5595) were added. After one hour incubation at 25° C., the plates were read on a PHERAstar FS plate reader (BMG Labtech). Ki values were determined.

Compounds of the present disclosure, as exemplified in Examples, showed the $K_i$ values in the following ranges: $+=K_i \leq 100$ nM; $++=100$ nM$<K_i \leq 500$ nM; $+++=500$ nM$<K_i \leq 5000$ nM.

TABLE 1

| Example | Ki, nM |
|---|---|
| 1, Peak 1 | + |
| 1, Peak 2 | + |
| 2 | + |
| 3, Peak 1 | + |
| 3, Peak 2 | + |
| 4, Peak 1 | + |
| 4, Peak 2 | + |
| 5, Peak 1 | + |
| 5, Peak 2 | + |
| 6, Peak 1 | + |
| 6, Peak 2 | + |
| 7, Peak 1 | + |
| 7, Peak 2 | + |
| 8, Peak 1 | + |
| 8, Peak 2 | + |
| 9 | + |
| 10, Peak 1 | + |
| 10, Peak 2 | + |
| 11 | + |
| 12 | + |
| 13 | + |
| 14, Peak 1 | + |
| 14, Peak 2 | + |
| 15, Peak 1 | + |
| 15, Peak 2 | + |
| 16, Peak 1 | +++ |
| 16, Peak 2 | + |
| 17 | + |
| 18, Peak 1 | + |
| 18, Peak 2 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | ++ |
| 30 | + |
| 31 | + |
| 32 | + |
| 33 | + |
| 34 | + |
| 35 | + |
| 36 | + |
| 37 | + |
| 38 | + |
| 39 | + |
| 40 | + |
| 41 | + |
| 42 | + |

Example B. p-SLP76S376 HTRF Assay

One or more compounds of the invention can be tested using the p-SLP76S376 HTRF assay described as follows. Jurkat cells (cultured in RPMI1640 media with 10% FBS) are collected and centrifuged, followed by resuspension in appropriate media at $3 \times 10^6$ cells/mL. The Jurkat cells (35 µL) are dispensed into each well in a 384 well plate. Test compounds are diluted with cell culture media for 40-fold dilution (adding 39 µL cell culture media into 1 µL compound). The Jurkat cells in the well plate are treated with the test compounds at various concentrations (adding 5 ul diluted compound into 35 µL Jurkat cells and starting from 3 uM with 1:3 dilution) for 1 hour at 37° C., 5% $CO_2$), followed by treatment with anti-CD3 (5 µg/mL, OKT3 clone) for 30 min. A 1:25 dilution of 100× blocking reagent (from p-SLP76 ser376HTRF kit) with 4× Lysis Buffer (LB) is prepared and 15 µL of the 4×LB buffer with blocking reagent is added into each well and incubated at room temperature for 45 mins with gentle shaking. The cell lysate (16 µL) is added into a Greiner white plate, treated with p-SLP76 ser376HTRF reagents (2 µL donor, 2 ul acceptor) and incubated at 4° C. for overnight. The homogeneous time resolved fluorescence (HTRF) is measured on a PHERAstar plate reader the next day. $IC_{50}$ determination is performed by fitting the curve of percent inhibition versus the log of the inhibitor concentration using the GraphPad Prism 5.0 software.

Example C. Isolation of CD4+ or CD8+ T Cells and Cytokine Measurement

Blood samples are collected from healthy donors. CD4+ or CD8+ T cells are isolated by negative selection using CD4+ or CD8+ enrichment kits (lifetech, USA). The purity of the isolated CD4+ or CD8+ T cells is determined by flow cytometry and is routinely >80%. Cells are cultured in RPMI 1640 supplemented with 10% FCS, glutamine and antibiotics (Invitrogen Life Technologies, USA). For cytokine measurement, Jurkat cells or primary CD4+ or CD8+ T cells are plated at 200 k cells/well and are stimulated for 24 h with anti-CD3/anti-CD28 beads in the presence or absence of testing compounds at various concentrations. 16 µL of supernatants are then transferred to a white detection plate and analyzed using the human IL2 or IFNγ assay kits (Cisbio).

Example D. Treg Assay

One or more compounds can be tested using the Regulatory T-cell proliferation assay described as following. Primary CD4+/CD25− T-cells and CD4+/CD25+ regulatory T-cells are isolated from human donated Peripheral Blood Mononuclear Cells, using an isolated kit from Thermo Fisher Scientific (11363D). CD4+/CD25− T-cells are labeled with CFSE (Thermo Fisher Scientific, C34554) following the protocol provided by the vendor. CFSE labeled T-cells and CD4+/CD25+ regulatory T-cells are re-suspended at the concentration of 1×106 cells/mL in RPMI-1640 medium. 100 µL of CFSE-labeled T-cells are mixed with or without 50 µL of CD4+/CD25+ regulatory T-cells, treated with 5 µl of anti-CD3/CD28 beads (Thermo Fisher Scientific, 11132D) and various concentrations of compounds diluted in 50 µl of RPMI-1640 medium. Mixed populations of cells are cultured for 5 days (37° C., 5% $CO_2$) and proliferation of CFSE-labeled T-cells is analyzed by BD LSRFortessa X-20 using FITC channel on the 5th day.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A compound of Formula (T)(II) or Formula (III):

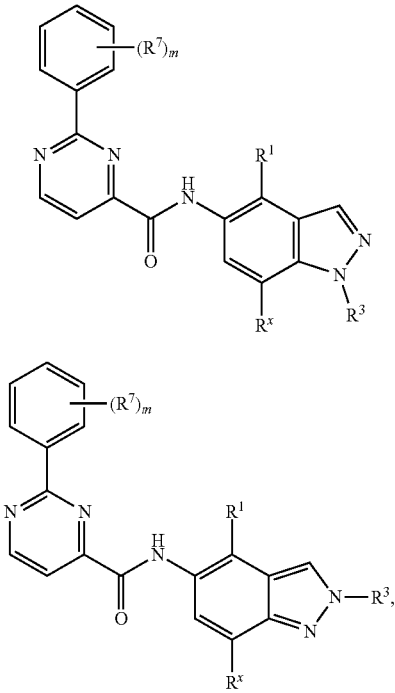

or a pharmaceutically acceptable salt thereof, wherein:

$R^1$ is selected from $Cy^1$, $C_{2-6}$ alkenyl, $C_{2-6}$ alkynyl, $C_{1-6}$ haloalkyl, CN, $NO_2$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NOR^a)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, $S(O)_2NR^cR^d$ and $BR^hR^i$; wherein said $C_{2-6}$ alkenyl and $C_{2-6}$ alkynyl are each optionally substituted with 1, 2, 3, or 4 substituents independently selected from $R^{10}$;

$Cy^1$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

$R^3$ is selected from $Cy^3$, $C_{1-6}$ alkyl, $C_{2-6}$ alkenyl, $C_{2-6}$ alkynyl, $C_{1-6}$ haloalkyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NOR^{a3})R^{b3}$, $C(=NR^{e3})NR^{c3}R^{d3}$ $NR^{c3}C(=NR^{e3})NR^{c3}R^{d3}$ $NR^{c3}S(O)R^{b3}$ $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$ and $BR^{h3}R^{i3}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$;

$R^X$ is selected from $Cy^4$, $C_{1-6}$ alkyl, $C_{2-6}$ alkenyl, $C_{2-6}$ alkynyl, $C_{1-6}$ haloalkyl, halo, CN, $NO_2$, $OR^{v1}$, $SR^{v1}$, $C(O)R^{w1}$, $C(O)NR^{x1}R^{y1}$, $C(O)OR^{v1}$, $OC(O)R^{w1}$, $OC(O)NR^{x1}R^{y1}$, $NR^{x1}R^{y1}$, $NR^{x1}C(O)R^{w1}$, $NR^{x1}C(O)OR^{v1}$, $NR^{x1}C(O)NR^{x1}R^{y1}$, $C(=NR^{z1})R^{w1}$, $C(=NOR^{v1})R^{w1}$, $C(=NR^{z1})NR^{x1}R^{y1}$, $NR^{x1}C(=NR^{z1})NR^{x1}R^{y1}$, $NR^{x1}S(O)R^{w1}$, $NR^{x1}S(O)_2R^{w1}$, $NR^{x1}S(O)_2NR^{x1}R^{y1}$, $S(O)R^{w1}$, $S(O)NR^{x1}R^{y1}$, $S(O)_2R^{w1}$, $S(O)_2NR^{x1}R^{y1}$ and $BR^{t1}R^{u1}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$;

$Cy^3$ and $Cy^4$ are each independently selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of the 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^7$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_1$-3 alkylene, halo, D, CN, $NO_2$, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$ $NR^{c7}C(O)NR^{c7}R^{d7}$, $C(=NR^{e7})R^{b7}$, $C(=NOR^{a7})R^{b7}$, $C(=NR^{e7})NR^{c7}R^{d7}$, $NR^{c7}C(=NR^{e7})NR^{c7}R^{d7}$ $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d}7$ and $BR^{h7}R^{i7}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_1$-3 alkylene are each optionally substituted with 1, 2, 3, or 4 substituents independently selected from $R^8$;

each $R^8$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a8}$, $SR^{a8}$, $C(O)R^{b8}$, $C(O)NR^{c8}R^{d8}$, $C(O)OR^{a8}$, $NR^{c8}R^{d8}$, $NR^{c8}C(O)R^{b8}$, $NR^{c8}C(O)OR^{a8}$, $NR^{c8}$ $S(O)R^{b8}$, $NR^{c8}S(O)_2R^{b8}$, $NR^{c8}S(O)_2NR^{c8}R^{d8}$, $S(O)R^{b8}$, $S(O)NR^{c8}R^{d8}$, $S(O)_2R^{b8}$, $S(O)_2NR^{c8}R^{d8}$ and $BR^{h8}R^{i8}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_1$-3 alkylene are each optionally substituted with 1, 2, 3, or 4 substituents independently selected from $R^9$;

each $R^9$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a9}$, $SR^{a9}$, $C(O)R^{b9}$, $C(O)NR^{c9}R^{d9}$, $C(O)OR^{a9}$, $NR^{c9}R^{d9}$, $NR^{c9}C(O)R^{b9}$, $NR^{c9}C(O)OR^{a9}$ $NR^{c9}S(O)R^{b9}$, $NR^{c9}S(O)_2R^{b9}$ $NR^{c9}S(O)_2NR^{c9}R^{d9}$, $S(O)R^{b9}$, $S(O)NR^{c9}R^{d9}$, $S(O)_2R^{b9}$, and $S(O)_2NR^{c9}R^{d9}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$ $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$ $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$ and $BR^{h1}R^{i1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a11}$, $SR^{a11}$, $C(O)R^{b11}$, $C(O)NR^{c11}R^{d11}$, $C(O)OR^{a11}$, $NR^{c11}R^{d11}$, $NR^{c11}C(O)R^{b11}$, $NR^{c11}C(O)OR^{a11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$ and $BR^{h11}R^{i11}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, $C_{6-10}$ aryl, 5-10 membered heteroaryl, 4-7 membered heterocycloalkyl, halo, D, CN, $OR^{a12}$, $SR^{a12}$, $C(O)R^{b12}$, $C(O)NR^{c12}R^{d12}$, $C(O)OR^{a12}$, $NR^{c12}R^{d12}$, $NR^{c12}C(O)R^{b12}$, $NR^{c12}C(O)OR^{a12}$ $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$ and $BR^{h12}R^{i12}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl are each optionally substituted with 1, 2, 3, or 4 substituents independently selected from $R^g$;

each $R^{13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a13}$, $SR^{a13}$, $C(O)R^{b13}$, $C(O)NR^{c13}R^{d13}$, $C(O)OR^{a13}$, $OC(O)R^{b13}$, $OC(O)NR^{c13}R^{d13}$, $NR^{c13}R^{d13}$ $NR^{c13}C(O)R^{b13}$, $NR^{c13}C(O)OR^{a13}$ $NR^{c13}C(O)NR^{c13}R^{d13}$, $C(=NR^{e13})R^{b13}$, $C(=NOR^{a13})R^{b13}$, $C(=NR^{e13})NR^{c13}R^{d13}$, $NR^{c13}C(=NR^{e13})NR^{c13}R^{d13}$ $NR^{c13}S(O)R^{b13}$, $NR^{c13}S(O)_2R^{b13}$ $NR^{c13}S(O)_2NR^{c13}R^{d13}$, $S(O)R^{b13}$, $S(O)NR^{c13}R^{d13}$, $S(O)_2R^{b13}$, $S(O)_2NR^{c13}R^{d13}$ and $BR^{h13}R^{i13}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{14}$;

each $R^{14}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a14}$, $SR^{a14}$, $C(O)R^{b14}$, $C(O)NR^{c14}R^{d14}$, $C(O)OR^{a14}$, $NR^{c14}R^{d14}$ $NR^{c14}C(O)R^{b14}$ $NR^{c14}C(O)OR^{a14}$ $NR^{c14}S(O)R^{b14}$, $NR^{c14}S(O)_2R^{b14}$, $NR^{c14}S(O)_2NR^{c14}R^{d14}$, $S(O)R^{b14}$, $S(O)NR^{c14}R^{d14}$, $S(O)_2R^{b14}$, $S(O)_2NR^{c14}R^{d14}$ and $BR^{h14}R^{i14}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{15}$;

each $R^{15}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a15}$, $SR^{a15}$, $C(O)R^{b15}$, $C(O)NR^{c15}R^{d15}$, $C(O)OR^{a5}$, $NR^{c15}R^{d15}$, $NR^{c15}C(O)R^{b15}$, $NR^{c15}C(O)OR^{a15}$ $NR^{c15}S(O)R^{b15}$, $NR^{c15}S(O)_2R^{b15}$ $NR^{c15}S(O)_2NR^{c15}R^{d15}$, $S(O)R^{b15}$, $S(O)NR^{c15}R^{d15}$, $S(O)_2R^{b15}$, and $S(O)_2NR^{c15}R^{d15}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^a$, $R^c$, and $R^d$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

or any $R^c$ and $R^d$ attached to the same N atom, together with the N atom to which they are attached, form a 4-10 membered heterocycloalkyl group optionally substituted with 1, 2, 3, or 4 substituents independently selected from $R^{10}$;

each $R^b$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^h$ and $R^i$ is independently selected from OH and $C_{1-6}$ alkoxy;

or any $R^h$ and $R^i$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, 6- or 7-membered heterocycloalkyl group optionally substituted with 1, 2, 3, or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{hi}$ and $R^{i1}$ is independently selected from OH and $C_{1-6}$ alkoxy;

or any $R^{hi}$ and $R^{i1}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

or any $R^{c3}$ and $R^{d3}$ attached to the same N atom, together with the N atom to which they are attached, form a 4-, 5-, 6- or 7-membered heterocycloalkyl group optionally substituted with 1, 2, 3, or 4 substituents independently selected from $R^{13}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^{e3}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h3}$ and $R^{i3}$ is independently selected from OH and $C_{1-6}$ alkoxy;

or any $R^{h3}$ and $R^{i3}$ attached to the same B atom are $C_2$-3 dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a7}$, $R^{c7}$ and $R^{d7}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

or any $R^{c7}$ and $R^{d7}$ attached to the same N atom, together with the N atom to which they are attached, form a 4-, 5-, 6- or 7-membered heterocycloalkyl group optionally substituted with 1, 2, 3, or 4 substituents independently selected from $R^8$;

each $R^{b7}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

each $R^{e7}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h7}$ and $R^{i7}$ is independently selected from OH and $C_{1-6}$ alkoxy;

or any $R^{h7}$ and $R^{i7}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a8}$, $R^{c8}$ and $R^{d8}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^9$;

or any $R^{c8}$ and $R^{d8}$ attached to the same N atom, together with the N atom to which they are attached, form a 4-, 5-, 6- or 7-membered heterocycloalkyl group optionally substituted with 1, 2, 3, or 4 substituents independently selected from $R^9$;

each $R^{b8}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^9$;

each $R^{h8}$ and $R^{i8}$ is independently selected from OH and $C_{1-6}$ alkoxy;

or any $R^{h8}$ and $R^{i8}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a9}$, $R^{c9}$ and $R^{d9}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b9}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a11}$, $R^{c11}$ and $R^{d11}$ is independently selected from H, $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

or any $R^{c11}$ and $R^{d11}$ attached to the same N atom, together with the N atom to which they are attached, form a 4-, 5-, 6- or 7-membered heterocycloalkyl group optionally substituted with 1, 2 or 3 substituents independently selected from $R^{12}$;

each $R^{b11}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl and 4-7 membered heterocycloalkyl; wherein said $C_{1-6}$ alkyl $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^{12}$;

each $R^{h11}$ and $R^{i1}$ is independently selected from OH and $C_{1-6}$ alkoxy;

or any $R^{h11}$ and $R^{i11}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a12}$, $R^{c12}$ and $R^{d12}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b12}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl $C_{2-6}$ alkenyl and $C_{2-6}$ alkynyl are each optionally substituted with 1, 2, 3, or 4 substituents independently selected from $R^g$;

each $R^{h12}$ and $R^{i12}$ is independently selected from OH and $C_{1-6}$ alkoxy;

or any $R^{h12}$ and $R^{i12}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a13}$, $R^{c13}$ and $R^{d13}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{14}$;

or any $R^{c13}$ and $R^{d13}$ attached to the same N atom, together with the N atom to which they are attached, form a 4-, 5-, 6- or 7-membered heterocycloalkyl group optionally substituted with 1, 2, 3, or 4 substituents independently selected from $R^{14}$;

each $R^{b13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{14}$;

each $R^{e13}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h13}$ and $R^{13}$ is independently selected from OH and $C_{1-6}$ alkoxy;

or any $R^{h13}$ and $R^{13}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a14}$, $R^{c14}$ and $R^{d14}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{15}$;

or any $R^{c14}$ and $R^{d14}$ attached to the same N atom, together with the N atom to which they are attached, form a 4-, 5-, 6- or 7-membered heterocycloalkyl group optionally substituted with 1, 2, 3, or 4 substituents independently selected from $R^{15}$;

each $R^{b14}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{15}$;

each $R^{h14}$ and $R^{i14}$ is independently selected from OH and $C_{1-6}$ alkoxy;

or any $R^{h14}$ and $R^{i14}$ attached to the same B atom are $C_{2-3}$ dialkoxy and together with the B atom to which they are attached, form a 5- or 6-membered heterocycloalkyl group optionally substituted with 1, 2, 3, or 4 substituents independently selected from $C_{1-6}$ alkyl;

each $R^{a15}$, $R^{c15}$ and $R^{d15}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b15}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{v1}$, $R^{x1}$, and $R^{y1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

or any $R^{x1}$ and $R^{y1}$ attached to the same N atom, together with the N atom to which they are attached, form a 4-10 membered heterocycloalkyl group optionally substituted with 1, 2, 3, or 4 substituents independently selected from $R^{13}$;

each $R^{w1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^{z1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{t1}$ and $R^{u1}$ is independently selected from OH and $C_{1-6}$ alkoxy;

or any $R^{t1}$ and $R^{u1}$ attached to the same B atom are $C_2$-3 dialkoxy and together with the B atom to which they are attached, form a 5- or 6-membered heterocycloalkyl group optionally substituted with 1, 2, 3, or 4 substituents independently selected from $C_{1-6}$ alkyl;

each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_1$_6 alkyl)aminosulfonylamino, aminocarbonylamino, $C_{1-6}$ alkylaminocarbonylamino, and di($C_{1-6}$ alkyl)aminocarbonylamino; and m is 1, 2, 3, or 4.

2. A compound of Formula (4)(II) or Formula (III):

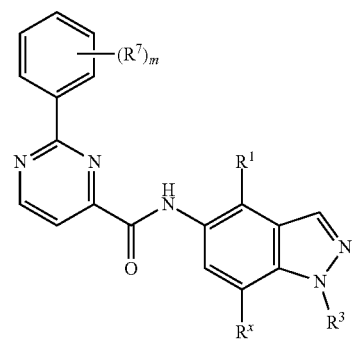

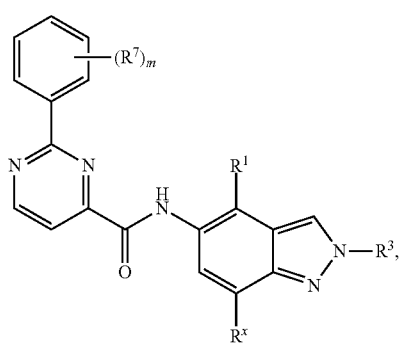

or a pharmaceutically acceptable salt thereof, wherein:

$R^1$ is selected from $Cy^1$ and $NR^cR^d$;

$Cy^1$ is selected from 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of the 5-10 membered heteroaryl and 4-10 membered heterocycloalkyl is optionally substituted by oxo to form a carbonyl group; and wherein the 4-10 membered heterocycloalkyl, $C_{6-10}$ aryl and 5-10 membered heteroaryl are each optionally substituted with 1, 2, 3, or 4 substituents independently selected from $R^{10}$;

$R^3$ is selected from $Cy^3$, $C_{1-6}$ alkyl, $C_{2-6}$ alkenyl, $C_{2-6}$ alkynyl, $C_{1-6}$ haloalkyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$ $NR^{c3}$ $S(O)R^{b3}$, $NR^{c3}$ $S(O)_2 R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$;

$R^X$ is selected from $C_{1-6}$ alkyl, CN, halo, $C(O)NR^{x1}R^{y1}$, and $Cy^4$; wherein said $C_{1-6}$ alkyl is optionally substituted with 1, 2, 3, or 4 substituents independently selected from $R^{13}$;

Cy$^3$ and Cy$^4$ are each independently is selected from C$_{3-10}$ cycloalkyl, 4-10 membered heterocycloalkyl, C$_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of the 5-10 membered heteroaryl and 4-10 membered heterocycloalkyl is optionally substituted by oxo to form a carbonyl group; and wherein the C$_{3-10}$ cycloalkyl, 4-10 membered heterocycloalkyl, C$_{6-10}$ aryl and 5-10 membered heteroaryl are each optionally substituted with 1, 2, 3, or 4 substituents independently selected from R$^{13}$;

each R$^7$ is independently selected from C$_{1-6}$ alkyl, C$_{2-6}$ alkenyl, C$_{2-6}$ alkynyl, C$_{1-6}$ haloalkyl, 5-10 membered heteroaryl, halo, D, CN, NO$_2$, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, NR$^{c7}$R$^{d7}$, NR$^{c7}$C(O)R$^{b7}$, NR$^{c7}$C(O)OR$^{a7}$, NR$^{c7}$C(O)NR$^{c7}$R$^{d7}$, NR$^{c7}$S(O)R$^{b7}$, NR$^{c7}$S(O)$_2$R$^{b7}$ NR$^{c7}$S(O)$_2$NR$^{c7}$R$^{d7}$, S(O)R$^{b7}$, S(O)NR$^{c7}$R$^{d7}$ S(O)$_2$R$^{b7}$ and S(O)$_2$NR$^{c7}$R$^{d7}$; wherein said C$_{1-6}$ alkyl, C$_{2-6}$ alkenyl, C$_{2-6}$ alkynyl, are each optionally substituted with 1, 2, 3, or 4 substituents independently selected from R$^8$;

each R$^8$ is independently selected from C$_{1-6}$ alkyl, C$_{1-6}$ haloalkyl, halo, D, CN, OR$^a$, SR$^{a8}$, C(O)R$^{b8}$, C(O)NR$^{c8}$R$^{d8}$, C(O)OR$^{a8}$, NR$^{c8}$R$^{d8}$ NR$^{c8}$C(O)R$^{b8}$, S(O)$_2$R$^{b8}$ and S(O)$_2$NR$^{c8}$R$^{d8}$;

each R$^{10}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, halo, D, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$OC(O) NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$ and S(O)$_2$NR$^{c1}$R$^{d1}$; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl, 5-10 membered heteroaryl, are each optionally substituted with 1, 2, 3, or 4 substituents independently selected from R$^{11}$;

each R$^{11}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, halo, D, CN, OR$^{a11}$, SR$^{a11}$, C(O)R$^{b11}$, C(O)NR$^{c11}$R$^{d11}$, C(O)OR$^{a11}$, NR$^{c11}$R$^{d11}$, NR$^{c11}$C(O)R$^{b11}$, NR$^{c11}$C(O)OR$^{a11}$, NR$^{c11}$S(O)R$^{b11}$ NR$^{c11}$S(O)$_2$R$^{b11}$ NR$^{c11}$S(O)$_2$NR$^{c11}$R$^{d11}$ S(O)R$^{b11}$, S(O)NR$^{c11}$R$^{d11}$, S(O)$_2$R$^{b11}$ and S(O)$_2$NR$^{c11}$R$^{d11}$;

each R$^{13}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl, 5-10 membered heteroaryl, halo, D, CN, NO$_2$, OR$^{a13}$, SR$^{a13}$, C(O)R$^{b13}$, C(O)NR$^{c13}$R$^{d13}$, C(O)OR$^{a13}$, OC(O) R$^{b13}$ OC(O)NR$^{c13}$R$^{d13}$ NR$^{c13}$R$^{d13}$ NR$^{c13}$C(O)R$^{b13}$ NR$^{c13}$C(O)OR$^{a13}$, NR$^{c13}$C(O)NR$^{c13}$R$^{d13}$ NR$^{c13}$S(O) R$^{b13}$, NR$^{c13}$S(O)$_2$R$^{b13}$, NR$^{c13}$S(O)$_2$NR$^{c13}$R$^{d13}$, S(O) R$^{b13}$, S(O)NR$^{c13}$R$^{d13}$, S(O)$_2$R$^{b13}$ and S(O)$_2$NR$^{c13}$R$^{d13}$;

each R$^c$, and R$^d$ is independently selected from H, C$_{1-6}$ alkyl, C$_{3-10}$ cycloalkyl, 4-10 membered heterocycloalkyl, C$_{6-10}$ aryl and 5-10 membered heteroaryl; wherein said C$_{1-6}$ alkyl, C$_{3-10}$ cycloalkyl, 4-10 membered heterocycloalkyl, C$_{6-10}$ aryl and 5-10 membered heteroaryl are each optionally substituted with 1, 2, 3, or 4 substituents independently selected from R$^{10}$;

each R$^{a1}$, R$^{c1}$ and R$^{d1}$ is independently selected from H, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl and 5-10 membered heteroaryl;

each R$^{b1}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl and 5-10 membered heteroaryl;

each R$^{a3}$, R$^{c3}$ and R$^{d3}$ is independently selected from H, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl and 5-10 membered heteroaryl; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl and 5-10 membered heteroaryl are each optionally substituted with 1, 2, 3, or 4 substituents independently selected from R$^{13}$;

each R$^{b3}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl and 5-10 membered heteroaryl; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl and 5-10 membered heteroaryl are each optionally substituted with 1, 2, 3, or 4 substituents independently selected from R$^{13}$;

each R$^{a7}$, R$^{c7}$ and R$^{d7}$ is independently selected from H, C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl and 5-10 membered heteroaryl; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl and 5-10 membered heteroaryl are each optionally substituted with 1, 2, 3, or 4 substituents independently selected from R$^8$;

or any R$^{c7}$ and R$^{d7}$ attached to the same N atom, together with the N atom to which they are attached, form a 4-, 5-, 6- or 7-membered heterocycloalkyl group optionally substituted with 1, 2, 3, or 4 substituents independently selected from R$^8$;

each R$^{b7}$ is independently selected from C$_{1-6}$ alkyl, C$_{2-6}$ alkenyl, C$_{2-6}$ alkynyl, C$_{1-6}$ haloalkyl, C$_{3-10}$ cycloalkyl, 4-10 membered heterocycloalkyl, C$_{6-10}$ aryl and 5-10 membered heteroaryl; wherein said C$_{1-6}$ alkyl, C$_{2-6}$ alkenyl, C$_{2-6}$ alkynyl, C$_{3-10}$ cycloalkyl, 4-10 membered heterocycloalkyl, C$_{6-10}$ aryl and 5-10 membered heteroaryl are each optionally substituted with 1, 2, 3, or 4 substituents independently selected from R$^8$;

each R$^{a8}$, R$^{c8}$ and R$^{d8}$ is independently selected from H, C$_{1-6}$ alkyl and C$_{1-6}$ haloalkyl;

each R$^{b8}$ is independently selected from C$_{1-6}$ alkyl and C$_{1-6}$ haloalkyl;

each R$^{a11}$, R$^{c11}$ and R$^{d11}$ is independently selected from H, C$_{1-6}$ alkyl and C$_{1-6}$ haloalkyl;

each R$^{b11}$ is independently selected from C$_{1-6}$ alkyl and C$_{1-6}$ haloalkyl;

each R$^{a13}$, R$^{c13}$ and R$^{d13}$ is independently selected from H, C$_{1-6}$ alkyl and C$_{1-6}$ haloalkyl;

each R$^{b13}$ is independently selected from C$_{1-6}$ alkyl and C$_{1-6}$ haloalkyl;

each R$^{x1}$ and R$^{y1}$ is independently selected from H and C$_{1-6}$ alkyl; and m is 1, 2, 3, or 4.

3. A compound of Formula (II) or Formula (III):

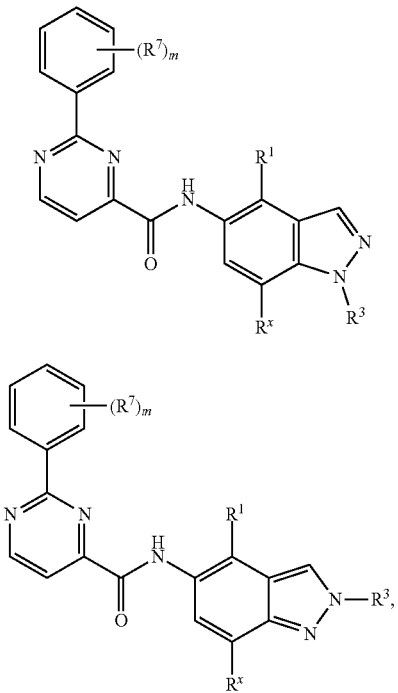

or a pharmaceutically acceptable salt thereof, wherein:
$R^1$ is $Cy^1$;
$Cy^1$ is selected from 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of the 5-10 membered heteroaryl and 4-10 membered heterocycloalkyl is optionally substituted by oxo to form a carbonyl group; and wherein the 4-10 membered heterocycloalkyl, $C_{6-10}$ aryl and 5-10 membered heteroaryl are each optionally substituted with 1, 2, 3, or 4 substituents independently selected from $R^{10}$;
$R^3$ is selected from $Cy^3$, $C_{1-6}$ alkyl, $C_{2-6}$ alkenyl, $C_{2-6}$ alkynyl, $C_{1-6}$ haloalkyl, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$ $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$;
$R^X$ is selected from 4 $C_{1-6}$ alkyl, CN, halo, $C(O)NR^{x1}R^{y1}$, and $Cy^4$; wherein said $C_{1-6}$ alkyl is optionally substituted with 1, 2, 3, or 4 substituents independently selected from $R^{13}$;
$Cy^3$ and $Cy^4$ are each independently is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of the 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;
each $R^7$ is independently selected from $C_{1-6}$ alkyl, $C_{2-6}$ alkenyl, $C_{2-6}$ alkynyl, $C_{1-6}$ haloalkyl, halo, D, CN, $NO_2$, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$ and $S(O)_2NR^{c7}R^{d7}$; wherein said $C_{1-6}$ alkyl, $C_{2-6}$ alkenyl, $C_{2-6}$ alkynyl, are each optionally substituted with 1, 2, 3, or 4 substituents independently selected from $R^8$;
each $R^8$ is independently selected from $C_{1-6}$ alkyl, $C_{1-6}$ haloalkyl, halo, D, CN, $OR^{a8}$, $SR^{a8}$, $C(O)R^{b8}$, $C(O)NR^{c8}R^{d8}$, $C(O)OR^{a88}$, $NR^{c8}R^{d8}$, $NR^{c8}C(O)R^{b8}$, $S(O)_2R^{b8}$ and $S(O)_2NR^{c8}R^{d8}$;
each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}OC(O)NR^{c1}R^{d1}$, $NR^{c1}R^{d1}$ $NR^{c1}C(O)R^{b1}$ $NR^{c1}C(O)OR^{a1}$ $NR^{c1}C(O)NR^{c1}R^{d1}$ $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, are each optionally substituted with 1, 2, 3, or 4 substituents independently selected from $R^{11}$;
each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $OR^{a11}$, $SR^{a11}$, $C(O)R^{b11}$, $C(O)NR^{c11}R^{d11}$, $C(O)OR^{a11}$, $NR^{c11}R^{d11}$, $NR^{c11}C(O)R^{b11}$, $NR^{c11}C(O)OR^{a11}$, $NR^{c11}S(O)R^{b11}$, $NR^{c11}S(O)_2R^{b11}$, $NR^{c11}S(O)_2NR^{c11}R^{d1111}$, $S(O)R^{b11}$, $S(O)NR^{c11}R^{d11}$, $S(O)_2R^{b11}$ and $S(O)_2NR^{c11}R^{d11}$;
each $R^{13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a13}$, $SR^{a13}$, $C(O)R^{b13}$, $C(O)NR^{c13}R^{d13}$, $C(O)OR^{a13}$, $OC(O)R^{b13}$ $OC(O)NR^{c13}R^{d13}$, $NR^{c13}R^{d13}$, $NR^{c13}C(O)R^{b13}$, $NR^{c13}C(O)OR^{a13}$, $NR^{c13}C(O)NR^{c13}R^{d13}$ $NR^{c13}S(O)R^{b13}$, $NR^{c13}S(O)_2R^{b13}$, $NR^{c13}S(O)_2NR^{c13}R^{d13}$, $S(O)R^{b13}$, $S(O)NR^{c13}R^{d13}$, $S(O)_2R^{b13}$ and $S(O)_2NR^{c13}R^{d13}$;
each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;
each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl;
each $R^{a3}$, $R^{c3}$ and $R^{d3}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^{b3}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^{a7}$, $R^{c7}$ and $R^{d7}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

or any $R^{c7}$ and $R^{d7}$ attached to the same N atom, together with the N atom to which they are attached, form a 4-, 5-, 6- or 7-membered heterocycloalkyl group optionally substituted with 1, 2, 3, or 4 substituents independently selected from $R^8$;

each $R^{b7}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

each $R^{a8}$, $R^{c8}$ and $R^{d8}$ is independently selected from H, $C_{1-6}$ alkyl and $C_{1-6}$ haloalkyl;

each $R^{b8}$ is independently selected from $C_{1-6}$ alkyl and $C_{1-6}$ haloalkyl;

each $R^{a11}$, $R^{c11}$ and $R^{d11}$ is independently selected from H, $C_{1-6}$ alkyl and $C_{1-6}$ haloalkyl;

each $R^{b11}$ is independently selected from $C_{1-6}$ alkyl and $C_{1-6}$ haloalkyl;

each $R^{a13}$, $R^{c13}$ and $R^{d13}$ is independently selected from H, $C_{1-6}$ alkyl and $C_{1-6}$ haloalkyl;

each $R^{b13}$ is independently selected from $C_{1-6}$ alkyl and $C_{1-6}$ haloalkyl;

each $R^{x1}$ and $R^{y1}$, is independently selected from H and $C_{1-6}$ alkyl; and m is 1, 2, 3, or 4.

4. The compound of claim 1, or a pharmaceutically acceptable salt thereof, wherein:

$R^1$ is $Cy^1$;

$Cy^1$ is selected from 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl and 4-10 membered heterocycloalkyl is optionally substituted by oxo to form a carbonyl group; and wherein the 4-10 membered heterocycloalkyl, $C_{6-10}$ aryl and 5-10 membered heteroaryl are each optionally substituted with 1, 2, 3, or 4 substituents independently selected from $R^{10}$;

$R^3$ is selected from $Cy^3$, $C_{1-6}$ alkyl, $C_{1-6}$ haloalkyl, halo, CN, and $C(O)NR^{c3}R^{d3}$; wherein said $C_{1-6}$ alkyl is optionally substituted with 1, 2, 3, or 4 substituents independently selected from $R^{13}$;

$R^X$ is selected from 4 $C_{1-6}$ alkyl, CN, halo, and $C(O)NR^{x1}R^{y1}$;

$Cy^3$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^7$ is independently selected from halo and $OR^{a7}$;

each $R^{10}$ is independently selected from $C_{1-6}$ alkyl, $OR^{a1}$, $C(O)NR^{c1}R^{d1}$, $NR^{c1}R^{d1}$, and $NR^{c1}C(O)OR^{a1}$; wherein said $C_{1-6}$ alkyl is optionally substituted with 1, 2, 3, or 4 substituents independently selected from $R^{11}$;

each $R^{11}$ is independently selected from $OR^{a11}$ and $NR^{c11}R^{d11}$;

each $R^{13}$ is independently selected from $C_{1-6}$ alkyl, halo, D, CN, and $OR^{a13}$;

each $R^{a1}$, $R^{c1}$ and $R^{d1}$ is independently selected from H and $C_{16}$ alkyl;

each $R^{a7}$ is independently selected from H and $C_{1-6}$ alkyl;

each $R^{a11}$, $R^{c11}$ and $R^{d11}$ is independently selected from H, and $C_{1-6}$ alkyl;

each $R^{a13}$ is independently selected from H, and $C_{1-6}$ alkyl;

each $R^{x1}$ and $R^{y1}$ is independently selected from H and $C_{1-6}$ alkyl; and m is 1, 2, 3, or 4.

5. The compound of claim 1, or a pharmaceutically acceptable salt thereof, wherein $R^1$ is $Cy^1$.

6. The compound of claim 1, or a pharmaceutically acceptable salt thereof, wherein $Cy^1$ is selected from 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the 5-10 membered heteroaryl and 4-10 membered heterocycloalkyl is optionally substituted by oxo; and wherein the 4-10 membered heterocycloalkyl, $C_{6-10}$ aryl, and 5-10 membered heteroaryl are each optionally substituted with 1, 2, 3, or 4 substituents independently selected from $R^{10}$.

7. The compound of claim 1, or a pharmaceutically acceptable salt thereof, wherein $Cy^1$ is selected from 4-10 membered heterocycloalkyl and 5-10 membered heteroaryl; wherein a ring-forming carbon atom of the 5-10 membered heteroaryl and 4-10 membered heterocycloalkyl is optionally substituted by oxo; and wherein the 4-10 membered heterocycloalkyl and 5-10 membered heteroaryl are each optionally substituted with 1, 2, 3, or 4 substituents independently selected from $R^{10}$.

8. The compound of claim 1, or a pharmaceutically acceptable salt thereof, wherein $Cy^1$ is $C_{6-10}$ aryl optionally substituted with 1, 2, 3, or 4 substituents independently selected from $R^{10}$.

9. The compound of claim 1, or a pharmaceutically acceptable salt thereof, wherein $Cy^1$ is phenyl optionally substituted with 1, 2, 3, or 4 substituents independently selected from $R^{10}$.

10. The compound of claim 1, or a pharmaceutically acceptable salt thereof, wherein $R^1$ is $NR^cR^d$.

11. The compound of claim 1, or a pharmaceutically acceptable salt thereof, wherein each $R^c$ and $R^d$ is independently selected from H, $C_{1-6}$ alkyl, and 4-7 membered heterocycloalkyl, wherein said $C_{1-6}$ alkyl and 4-7 membered heterocycloalkyl are each optionally substituted with 1, 2, or 3 substituents independently selected from $R^{10}$.

12. The compound of claim 1, or a pharmaceutically acceptable salt thereof, wherein each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, and 5-10 membered heteroaryl are each optionally substituted with 1, 2, 3, or 4 substituents independently selected from $R^{11}$.

13. The compound of claim 1, or a pharmaceutically acceptable salt thereof, wherein each $R^{10}$ is independently selected from $C_{1-6}$ alkyl, $C_{2-6}$ alkenyl, $C_{2-6}$ alkynyl, $C_{1-6}$ haloalkyl, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, and $NR^{c1}C(O)OR^{a1}$; wherein said $C_{1-6}$ alkyl, $C_{2-6}$ alkenyl, and $C_{2-6}$ alkynyl are each optionally substituted with 1, 2, 3, or 4 substituents independently selected from $R^{11}$.

14. The compound of claim 1, or a pharmaceutically acceptable salt thereof, wherein each $R^{10}$ is independently selected from $C_{1-6}$ alkyl, $OR^{a1}$, $C(O)NR^{c1}R^{d1}$ and $NR^{c1}R^{d1}$.

15. The compound of claim 1, or a pharmaceutically acceptable salt thereof, wherein each $R^{10}$ is independently selected from $C(O)NR^{c1}R^{d1}$, $NR^{c1}R^{d1}$, and $C_{1-6}$ alkyl; each optionally substituted with 1, 2, 3, or 4 substituents independently selected from $R^{11}$.

16. The compound of claim 1, or a pharmaceutically acceptable salt thereof, wherein $R^{c1}$ is selected from H and $C_{1-6}$ alkyl.

17. The compound of claim 1, or a pharmaceutically acceptable salt thereof, wherein $R^{d1}$ is selected from H and $C_{1-6}$ alkyl.

18. The compound of claim 1, or a pharmaceutically acceptable salt thereof, wherein each $R^{11}$ is independently selected from $OR^{a11}$ and $NR^{c11}R^{d11}$.

19. The compound of claim 1, or a pharmaceutically acceptable salt thereof, wherein each $R^{a11}$, $R^{c11}$ and $R^{d11}$ is independently selected from H and $C_{1-6}$ alkyl.

20. The compound of claim 1, or a pharmaceutically acceptable salt thereof, wherein $R^{a11}$ is H.

21. The compound of claim 1, or a pharmaceutically acceptable salt thereof, wherein $R^{c11}$ is selected from H and $C_{1-6}$ alkyl.

22. The compound of claim 1, or a pharmaceutically acceptable salt thereof, wherein $R^{d11}$ is H.

23. The compound of claim 1, or a pharmaceutically acceptable salt thereof, wherein $Cy^1$ is selected from 2,5-diazabicyclo[2.2.1]heptan-2-yl; 5-(ethylcarbamoyl)-2,5-diazabicyclo[2.2.1]heptan-2-yl; 4-amino-2-(hydroxymethyl)pyrrolidin-1-yl; 3-aminopyrrolidin-1-yl; 2,5-diazabicyclo[2.2.1]octan-2-yl; 2-(hydroxymethyl)pyrrolidin-1-yl; morpholino; 6-oxo-2,7-diazaspiro[4.4]nonan-2-yl; 3-aminoazetidin-1-yl; 2-(aminomethyl)pyrrolidin-1-yl; pyrrolidin-3-yl; 2-oxopyrrolidin-1-yl; 1H-pyrazol-1-yl; o-tolyl; 3-aminopiperidin-1-yl; piperazin-1-yl; pyridin-3-yl; 1-methyl-1H-pyrazol-4-yl; 3-(hydroxymethyl)phenyl; 2-(hydroxymethyl)phenyl; 3-((dimethylamino)methyl)phenyl; 4-(dimethylamino)piperidin-1-yl; 4-hydroxy-2-(aminomethyl)pyrrolidin-1-yl and 3-(hydroxymethyl)piperazin-1-yl.

24. The compound of claim 1, or a pharmaceutically acceptable salt thereof, wherein $Cy^1$ is selected from 2,5-diazabicyclo[2.2.1]heptan-2-yl; 5-(ethylcarbamoyl)-2,5-diazabicyclo[2.2.1]heptan-2-yl; 4-amino-2-(hydroxymethyl)pyrrolidin-1-yl; 3-aminopyrrolidin-1-yl; 2,5-diazabicyclo[2.2.1]octan-2-yl; 2-(hydroxymethyl)pyrrolidin-1-yl; morpholino; 6-oxo-2,7-diazaspiro[4.4]nonan-2-yl; 3-aminoazetidin-1-yl; 2-(aminomethyl)pyrrolidin-1-yl; pyrrolidin-3-yl; 2-oxopyrrolidin-1-yl; 1H-pyrazol-1-yl; o-tolyl; 3-aminopiperidin-1-yl; piperazin-1-yl; pyridin-3-yl; 1-methyl-1H-pyrazol-4-yl; 3-(hydroxymethyl)phenyl; 2-(hydroxymethyl)phenyl; 3-((dimethylamino)methyl)phenyl; and 4-(dimethylamino)piperidin-1-yl.

25. The compound of claim 1, or a pharmaceutically acceptable salt thereof, wherein $Cy^1$ is selected from 4-hydroxy-2-(aminomethyl)pyrrolidin-1-yl and 3-(hydroxymethyl)piperazin-1-yl.

26. The compound of claim 1, wherein $R^3$ is selected from $Cy^3$, $C_{1-6}$ alkyl, $C_{2-6}$ alkenyl, $C_{2-6}$ alkynyl, $C_{1-6}$ haloalkyl, halo, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, and $NR^{c3}C(O)NR^{c3}R^{d3}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$.

27. The compound of claim 1, wherein $R^3$ is selected from $Cy^3$, $C_{1-6}$ alkyl, and $C_{1-6}$ haloalkyl; wherein said $C_{1-6}$ alkyl is optionally substituted with 1, 2, 3, or 4 substituents independently selected from $R^{13}$.

28. The compound of claim 1, or a pharmaceutically acceptable salt thereof, wherein $R^3$ is optionally substituted $C_{1-6}$ alkyl.

29. The compound of claim 1, or a pharmaceutically acceptable salt thereof, wherein $R^3$ is methyl.

30. The compound of claim 1, or a pharmaceutically acceptable salt thereof, wherein $R^3$ is 2-hydroxyethyl.

31. The compound of claim 1, or a pharmaceutically acceptable salt thereof, wherein $R^3$ is 2-methoxyethyl.

32. The compound of claim 1, or a pharmaceutically acceptable salt thereof, wherein $R^3$ is 2-fluoroethyl.

33. The compound of claim 1, or a pharmaceutically acceptable salt thereof, wherein $R^3$ is $Cy^3$.

34. The compound of claim 1, or a pharmaceutically acceptable salt thereof, wherein $Cy^3$ is 4-10 membered heterocycloalkyl or 5-10 membered heteroaryl, each of which is optionally substituted with 1, 2, 3, or 4 substituents independently selected from $R^{13}$.

35. The compound of claim 1, or a pharmaceutically acceptable salt thereof, wherein $Cy^3$ is 4-10 membered heterocycloalkyl, which is optionally substituted with 1, 2, 3, or 4 substituents independently selected from $R^{13}$.

36. The compound of claim 1, or a pharmaceutically acceptable salt thereof, wherein $Cy^3$ is tetrahydrofuranyl.

37. The compound of claim 1, or a pharmaceutically acceptable salt thereof, wherein $Cy^3$ is 5-10 membered heteroaryl, which is optionally substituted with 1, 2, 3, or 4 substituents independently selected from $R^{13}$.

38. The compound of claim 1, or a pharmaceutically acceptable salt thereof, wherein each $R^{13}$ is independently selected from $C_{1-6}$ alkyl, halo, CN and $OR^{a13}$.

39. The compound of claim 1, or a pharmaceutically acceptable salt thereof, wherein $R^{13}$ is CN.

40. The compound of claim 1, or a pharmaceutically acceptable salt thereof, wherein $Cy^3$ is 3-cyanopyridinyl.

41. The compound of claim 1, or a pharmaceutically acceptable salt thereof, wherein $R^X$ is selected from H, D, $Cy^4$, $C_{1-6}$ alkyl, $C_{2-6}$ alkenyl, $C_{2-6}$ alkynyl, $C_{1-6}$ haloalkyl, halo, CN, $OR^{v1}$, $SR^{v1}$, $C(O)R^{w1}$, $C(O)NR^{x1}R^{y1}$, $C(O)OR^{x1}$, $OC(O)R^{w1}$, $OC(O)NR^{x1}R^{y1}$, $NR^{x1}R^{y1}$, $NR^{x1}C(O)R^{w1}$, $NR^{x1}C(O)OR^{v1}$, and $NR^{x1}C(O)NR^{x1}R^{y1}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$.

42. The compound of claim 1, or a pharmaceutically acceptable salt thereof, wherein $R^X$ is selected from H, D, $C_{1-6}$ alkyl, CN, halo, and $C(O)NR^{x1}R^{y1}$; wherein said $C_{1-6}$ alkyl is optionally substituted with 1, 2, 3, or 4 substituents independently selected from $R^{13}$.

43. T The compound of claim 1, or a pharmaceutically acceptable salt thereof, wherein $R^X$ is halo.

44. The compound of claim 1, or a pharmaceutically acceptable salt thereof, wherein $R^X$ is F.

45. The compound of claim 1, or a pharmaceutically acceptable salt thereof, wherein $R^X$ is CN.

46. The compound of claim 1, or a pharmaceutically acceptable salt thereof, wherein $R^X$ is $C_{1-6}$ alkyl optionally substituted with 1, 2, 3, or 4 substituents independently selected from $R^{13}$.

47. The compound of claim 1, or a pharmaceutically acceptable salt thereof, wherein $R^X$ is methyl.

48. The compound of claim 1, or a pharmaceutically acceptable salt thereof, wherein $R^X$ is $C(O)NR^{x1}R^{y1}$.

49. The compound of claim 1, or a pharmaceutically acceptable salt thereof, wherein $R^{x1}$ is selected from $C_{1-6}$ alkyl and H.

50. The compound of claim 1, or a pharmaceutically acceptable salt thereof, wherein $R^{y1}$ is selected from $C_{1-6}$ alkyl and H.

51. The compound of claim 1, or a pharmaceutically acceptable salt thereof, wherein each $R^7$ is independently selected from $C_{1-6}$ alkyl, $C_{2-6}$ alkenyl, $C_{2-6}$ alkynyl, $C_{1-6}$ haloalkyl, halo, D, CN, $NO_2$, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$ and $S(O)_2NR^{c7}R^{d7}$; wherein said $C_{1-6}$ alkyl, $C_{2-6}$ alkenyl, $C_{2-6}$ alkynyl, are each optionally substituted with 1, 2, 3, or 4 substituents independently selected from $R^8$.

52. The compound of claim 1, or a pharmaceutically acceptable salt thereof, wherein each $R^7$ is independently selected from $C_{1-6}$ alkyl, $C_{2-6}$ alkenyl, $C_{2-6}$ alkynyl, $C_{1-6}$ haloalkyl, halo, D, CN, $OR^{a7}$, $SR^{a7}$, $C(O)R^{b7}$, $C(O)NR^{c7}R^{d7}$, $C(O)OR^{a7}$, $NR^{c7}R^{d7}$, $NR^{c7}C(O)R^{b7}$, $NR^{c7}C(O)OR^{a7}$, and $NR^{c7}C(O)NR^{c7}R^{d7}$; wherein said $C_{1-6}$ alkyl, $C_{2-6}$ alkenyl, $C_{2-6}$ alkynyl, are each optionally substituted with 1, 2, 3, or 4 substituents independently selected from $R^8$.

53. The compound of claim 1, or a pharmaceutically acceptable salt thereof, wherein each $R^7$ is independently selected from $C_{1-6}$ alkyl, 5-10 membered heteroaryl, halo, $OR^{a7}$, $C(O)NR^{c7}R^{d7}$, $NR^{c7}R^{d7}$, wherein said $C_{1-6}$ alkyl and 5-10 membered heteroaryl are each optionally substituted with 1, 2, or 3 substituents independently selected from $R^8$.

54. The compound of claim 1, or a pharmaceutically acceptable salt thereof, wherein each $R^7$ is independently selected from halo and $OR^{a7}$.

55. The compound of claim 1, or a pharmaceutically acceptable salt thereof, wherein $R^{a7}$ is $C_{1-6}$ alkyl.

56. The compound of claim 1, or a pharmaceutically acceptable salt thereof, wherein $R^{a7}$ is methyl.

57. The compound of claim 1, or a pharmaceutically acceptable salt thereof, wherein each $R^{13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, halo, D, CN, $NO_2$, $OR^{a13}$, $SR^{a13}$, $C(O)R^{b13}$, $C(O)NR^{c13}R^{d13}$, $C(O)OR^{a13}$, $OC(O)R^{b13}$, $OC(O)NR^{c13}R^{d13}$, $NR^{c13}R^{d13}$, $NR^{c13}C(O)R^{b13}$, $NR^{c13}C(O)OR^{a13}$, $NR^{c13}C(O)NR^{c13}R^{d13}$, $NR^{c13}S(O)R^{b13}$, $NR^{c13}S(O)_2R^{b13}$, $NR^{c13}S(O)_2NR^{c13}R^{d13}$, $S(O)R^{b13}$, $S(O)NR^{c13}R^{d13}$, $S(O)_2R^{b3}$ and $S(O)_2NR^{c13}R^{d13}$.

58. The compound of claim 1, or a pharmaceutically acceptable salt thereof, wherein each $R^{13}$ is independently selected from $C_{1-6}$ alkyl, $C_{2-6}$ alkenyl, $C_{2-6}$ alkynyl, $C_{1-6}$ haloalkyl, halo, D, CN, $OR^{a13}$, $SR^{a13}$, $C(O)R^{b13}$, $C(O)NR^{c13}R^{d13}$, $C(O)OR^{a13}$, $NR^{c13}R^{d13}$, $NR^{c13}C(O)R^{b3}$, $NR^{c13}C(O)OR^{a13}$, and $NR^{c13}C(O)NR^{c13}R^{d13}$.

59. The compound of claim 1, or a pharmaceutically acceptable salt thereof, wherein each $R^{13}$ is independently selected from $C_{1-6}$ alkyl, CN, and $OR^{a13}$.

60. The compound of claim 1, having Formula II:

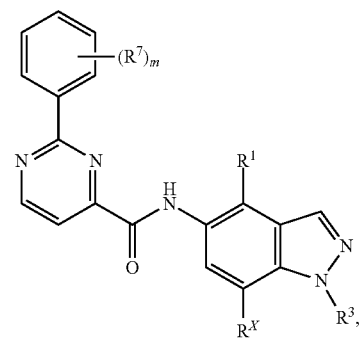

or a pharmaceutically acceptable salt thereof, wherein m is 1, 2, 3, or 4.

61. The compound of claim 1, having Formula III:

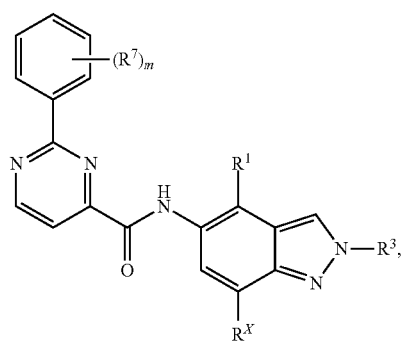

or a pharmaceutically acceptable salt thereof, wherein m is 1, 2, 3, or 4.

62. The compound of claim 1 selected from:
N-(4-((1S,4S)-2,5-Diazabicyclo[2.2.1]heptan-2-yl)-7-fluoro-1-methyl-1H-indazol-5-yl)-2-(2-fluoro-6-methoxyphenyl)pyrimidine-4-carboxamide;
N-(4-((1S,4S)-2,5-diazabicyclo[2.2.1]heptan-2-yl)-7-fluoro-2-methyl-2H-indazol-5-yl)-2-(2-fluoro-6-methoxyphenyl)pyrimidine-4-carboxamide;

(1S,4S)—N-Ethyl-5-(7-fluoro-5-(2-(2-fluoro-6-methoxyphenyl)pyrimidine-4-carboxamido)-1-methyl-1H-indazol-4-yl)-2, 5-diazabicyclo[2.2.1]heptane-2-carboxamide;

N-(4-((2S,4S)-4-Amino-2-(hydroxymethyl)pyrrolidin-1-yl)-7-fluoro-1-methyl-1H-indazol-5-yl)-2-(2-fluoro-6-methoxyphenyl)pyrimidine-4-carboxamide;

N-(4-((2S,4S)-4-amino-2-(hydroxymethyl)pyrrolidin-1-yl)-7-fluoro-2-methyl-2H-indazol-5-yl)-2-(2-fluoro-6-methoxyphenyl)pyrimidine-4-carboxamide;

(R)—N-(4-(3-Aminopyrrolidin-1-yl)-7-fluoro-1-methyl-1H-indazol-5-yl)-2-(2-fluoro-6-methoxyphenyl)pyrimidine-4-carboxamide;

(R)—N-(4-(3-aminopyrrolidin-1-yl)-7-fluoro-2-methyl-2H-indazol-5-yl)-2-(2-fluoro-6-methoxyphenyl)pyrimidine-4-carboxamide;

N-(4-((1S,4S)-2, 5-Diazabicyclo[2.2.2]octan-2-yl)-7-fluoro-1-methyl-1H-indazol-5-yl)-2-(2-fluoro-6-methoxyphenyl)pyrimidine-4-carboxamide;

N-(4-((1S,4S)-2, 5-diazabicyclo[2.2.2]octan-2-yl)-7-fluoro-2-methyl-2H-indazol-5-yl)-2-(2-fluoro-6-methoxyphenyl)pyrimidine-4-carboxamide;

(R)—N-(7-Fluoro-4-(2-(hydroxymethyl)pyrrolidin-1-yl)-1-methyl-1H-indazol-5-yl)-2-(2-fluoro-6-methoxyphenyl)pyrimidine-4-carboxamide;

(R)—N-(7-fluoro-4-(2-(hydroxymethyl)pyrrolidin-1-yl)-2-methyl-2H-indazol-5-yl)-2-(2-fluoro-6-methoxyphenyl)pyrimidine-4-carboxamide;

N-(7-Fluoro-1-methyl-4-morpholino-1H-indazol-5-yl)-2-(2-fluoro-6-methoxyphenyl)pyrimidine-4-carboxamide;

N-(7-fluoro-2-methyl-4-morpholino-2H-indazol-5-yl)-2-(2-fluoro-6-methoxyphenyl)pyrimidine-4-carboxamide;

N-(7-Fluoro-1-methyl-4-(6-oxo-2,7-diazaspiro[4.4]nonan-2-yl)-1H-indazol-5-yl)-2-(2-fluoro-6-methoxyphenyl)pyrimidine-4-carboxamide;

N-(7-fluoro-2-methyl-4-(6-oxo-2, 7-diazaspiro[4.4]nonan-2-yl)-2H-indazol-5-yl)-2-(2-fluoro-6-methoxyphenyl)pyrimidine-4-carboxamide;

N-(4-(3-Aminoazetidin-1-yl)-7-fluoro-1-methyl-1H-indazol-5-yl)-2-(2-fluoro-6-methoxyphenyl)pyrimidine-4-carboxamide;

(R)—N-(4-(2-(Aminomethyl)pyrrolidin-1-yl)-7-fluoro-1-methyl-1H-indazol-5-yl)-2-(2-fluoro-6-methoxyphenyl)pyrimidine-4-carboxamide;

(R)—N-(4-(2-(Aminomethyl)pyrrolidin-1-yl)-7-fluoro-2-methyl-2H-indazol-5-yl)-2-(2-fluoro-6-methoxyphenyl)pyrimidine-4-carboxamide;

N-(7-Fluoro-1-methyl-4-(pyrrolidin-3-yl)-1H-indazol-5-yl)-2-(2-fluoro-6-methoxyphenyl)pyrimidine-4-carboxamide;

N-(7-Fluoro-1-methyl-4-(2-oxopyrrolidin-1-yl)-1H-indazol-5-yl)-2-(2-fluoro-6-methoxyphenyl)pyrimidine-4-carboxamide;

N-(7-Fluoro-1-methyl-4-(1H-pyrazol-1-yl)-1H-indazol-5-yl)-2-(2-fluoro-6-methoxyphenyl)pyrimidine-4-carboxamide;

N-(7-Fluoro-1-methyl-4-o-tolyl-1H-indazol-5-yl)-2-(2-fluoro-6-methoxyphenyl)pyrimidine-4-carboxamide;

N-(7-Fluoro-2-methyl-4-o-tolyl-2H-indazol-5-yl)-2-(2-fluoro-6-methoxyphenyl)pyrimidine-4-carboxamide;

(R)—N-(4-(3-aminopiperidin-1-yl)-7-cyano-1-methyl-1H-indazol-5-yl)-2-(2-fluoro-6-methoxyphenyl)pyrimidine-4-carboxamide;

(R)—N-(4-(3-aminopiperidin-1-yl)-7-cyano-2-methyl-2H-indazol-5-yl)-2-(2-fluoro-6-methoxyphenyl)pyrimidine-4-carboxamide;

(R)-4-(3-aminopiperidin-1-yl)-5-(2-(2-fluoro-6-methoxyphenyl)pyrimidine-4-carboxamido)-N, 1-dimethyl-1H-indazole-7-carboxamide;

(R)-4-(3-aminopiperidin-1-yl)-5-(2-(2-fluoro-6-methoxyphenyl)pyrimidine-4-carboxamido)-N, 2-dimethyl-2H-indazole-7-carboxamide;

(R)—N-(4-(3-Aminopyrrolidin-1-yl)-7-fluoro-1-(2-hydroxyethyl)-1H-indazol-5-yl)-2-(2-fluoro-6-methoxyphenyl)pyrimidine-4-carboxamide;

N-(1, 7-Dimethyl-4-(piperazin-1-yl)-1H-indazol-5-yl)-2-(2-fluoro-6-methoxyphenyl)pyrimidine-4-carboxamide;

N-(2,7-dimethyl-4-(piperazin-1-yl)-2H-indazol-5-yl)-2-(2-fluoro-6-methoxyphenyl)pyrimidine-4-carboxamide;

(R)—N-(4-(3-aminopyrrolidin-1-yl)-1,7-dimethyl-1H-indazol-5-yl)-2-(2-fluoro-6-methoxyphenyl)pyrimidine-4-carboxamide;

N-(7-Fluoro-1-methyl-4-(pyridin-3-yl)-1H-indazol-5-yl)-2-(2-fluoro-6-methoxyphenyl)pyrimidine-4-carboxamide;

N-(7-Fluoro-1-methyl-4-(1-methyl-1H-pyrazol-4-yl)-1H-indazol-5-yl)-2-(2-fluoro-6-methoxyphenyl)pyrimidine-4-carboxamide;

N-(7-Fluoro-4-(3-(hydroxymethyl)phenyl)-1-methyl-1H-indazol-5-yl)-2-(2-fluoro-6-methoxyphenyl)pyrimidine-4-carboxamide;

N-(7-Fluoro-4-(2-(hydroxymethyl)phenyl)-1-methyl-1H-indazol-5-yl)-2-(2-fluoro-6-methoxyphenyl)pyrimidine-4-carboxamide;

N-(4-(3-((Dimethylamino)methyl)phenyl)-7-fluoro-1-methyl-1H-indazol-5-yl)-2-(2-fluoro-6-methoxyphenyl)pyrimidine-4-carboxamide;

N-(4-((1S,4S)-2, 5-diazabicyclo[2.2.1]heptan-2-yl)-7-fluoro-1-(2-hydroxyethyl)-1H-indazol-5-yl)-2-(2-fluoro-6-methoxyphenyl)pyrimidine-4-carboxamide; and N-(4-((1S,4S)-2, 5-diazabicyclo[2.2.1]heptan-2-yl)-7-fluoro-1-(2-methoxyethyl)-1H-indazol-5-yl)-2-(2-fluoro-6-methoxyphenyl)pyrimidine-4-carboxamide;

or a pharmaceutically acceptable salt thereof.

63. The compound of claim 1, selected from:

N-(4-((2S,4S)-4-Amino-2-(hydroxymethyl)pyrrolidin-1-yl)-7-fluoro-1-(2-methoxyethyl)-1H-indazol-5-yl)-2-(2-fluoro-6-methoxyphenyl)pyrimidine-4-carboxamide;

N-(4-((2S,4S)-4-Amino-2-(hydroxymethyl)pyrrolidin-1-yl)-7-fluoro-1-((R)-tetrahydrofuran-3-yl)-1H-indazol-5-yl)-2-(2-fluoro-6-methoxyphenyl)pyrimidine-4-carboxamide;

(R)—N-(7-Fluoro-4-(3-(hydroxymethyl)piperazin-1-yl)-2-methyl-2H-indazol-5-yl)-2-(2-fluoro-6-methoxyphenyl)pyrimidine-4-carboxamide;

N-(4-((2S,4S)-4-Amino-2-(hydroxymethyl)pyrrolidin-1-yl)-1-(3-cyanopyridin-4-yl)-7-fluoro-1H-indazol-5-yl)-2-(2-fluoro-6-methoxyphenyl)pyrimidine-4-carboxamide;

N-(4-((2S,4S)-2-(Aminomethyl)-4-hydroxypyrrolidin-1-yl)-7-fluoro-1-methyl-1H-indazol-5-yl)-2-(2-fluoro-6-methoxyphenyl)pyrimidine-4-carboxamide; and N-(4-((1S,4S)-2, 5-Diazabicyclo[2.2.1]heptan-2-yl)-7-fluoro-1-(2-fluoroethyl)-1H-indazol-5-yl)-2-(2-fluoro-6-methoxyphenyl)pyrimidine-4-carboxamide;

or a pharmaceutically acceptable salt thereof.

64. The compound of claim 1, selected from:
N-(4-((2S,4S)-4-Amino-2-(hydroxymethyl)pyrrolidin-1-yl)-7-fluoro-1-(2-methoxyethyl)-1H-indazol-5-yl)-2-(2-fluoro-6-(methoxy-d₃)-3-methylphenyl)pyrimidine-4-carboxamide;
N-(4-((2S,4S)-4-Amino-2-(hydroxymethyl)pyrrolidin-1-yl)-7-fluoro-1-(2-methoxyethyl)-1H-indazol-5-yl)-2-(4-amino-2-fluoro-6-methoxyphenyl)pyrimidine-4-carboxamide;
N-(4-((2S,4S)-4-amino-2-(hydroxymethyl)pyrrolidin-1-yl)-7-fluoro-1-(2-methoxyethyl)-1H-indazol-5-yl)-2-(2-fluoro-6-methoxy-3-(methylcarbamoyl)phenyl)pyrimidine-4-carboxamide;
N-(4-((2S,4S)-4-Amino-2-(hydroxymethyl)pyrrolidin-1-yl)-7-fluoro-1-(2-methoxyethyl)-1H-indazol-5-yl)-2-(2-fluoro-6-methoxy-3-(1-methyl-1H-pyrazol-4-yl)phenyl)pyrimidine-4-carboxamide; and
(R)—N-(7-Fluoro-1-methyl-4-(methyl(piperidin-3-yl)amino)-1H-indazol-5-yl)-2-(2-fluoro-6-methoxyphenyl)pyrimidine-4-carboxamide; and
or a pharmaceutically acceptable salt thereof.

65. A pharmaceutical composition comprising a compound of claim 1, or a pharmaceutically acceptable salt thereof, and at least one pharmaceutically acceptable carrier or excipient.

66. The compound of claim 1, which is (R)—N-(4-(3-aminopyrrolidin-1-yl)-1,7-dimethyl-1H-indazol-5-yl)-2-(2-fluoro-6-methoxyphenyl)pyrimidine-4-carboxamide, or a pharmaceutically acceptable salt thereof.

67. The compound of claim 1, which is (R)—N-(4-(3-aminopyrrolidin-1-yl)-1,7-dimethyl-1H-indazol-5-yl)-2-(2-fluoro-6-methoxyphenyl)pyrimidine-4-carboxamide.

\* \* \* \* \*